United States Patent [19]

Woodward et al.

[11] 4,256,739
[45] Mar. 17, 1981

[54] 7β-AMINO-3-THIO-3-CEPHEM-4-CARBOXYLIC ACID COMPOUNDS, AND ANTIBACTERIAL COMPOSITIONS AND METHODS USING THEM

[75] Inventors: Robert B. Woodward, Cambridge, Mass.; Hans Bickel, Binningen, Switzerland

[73] Assignee: Ciba-Geigy Corporation, Ardsley, N.Y.

[21] Appl. No.: 607,983

[22] Filed: Aug. 26, 1975

[30] Foreign Application Priority Data

Aug. 30, 1974 [CH] Switzerland ............... 11836/74

[51] Int. Cl.³ ............... A61K 31/545; C07D 501/59
[52] U.S. Cl. ............... 424/200; 424/246; 544/17; 544/26; 544/27; 544/29
[58] Field of Search ............... 260/243 C; 544/27, 29, 544/26, 17; 424/246, 200

[56] References Cited

U.S. PATENT DOCUMENTS

| | | | |
|---|---|---|---|
| 3,278,531 | 10/1966 | Cox et al. | 260/243 C |
| 3,766,177 | 10/1973 | Webber et al. | 260/243 C |
| 3,917,587 | 11/1975 | Chauvette | 260/243 C |
| 3,917,588 | 11/1975 | Chauvette | 260/243 C |
| 3,925,372 | 12/1975 | Chauvette | 260/243 C |
| 3,992,377 | 11/1976 | Chauvette et al. | 260/243 C |
| 4,066,641 | 1/1978 | Hamashima et al. | 544/17 |
| 4,123,528 | 10/1978 | Cama et al. | 424/248.52 |
| 4,150,156 | 4/1979 | Beattie et al. | 424/246 |

*Primary Examiner*—Donald G. Daus
*Assistant Examiner*—Diana G. Rivers
*Attorney, Agent, or Firm*—Prabodh I. Almaula

[57] ABSTRACT

7β-Amino-3-$R_3$-thio-3-cephem-4-carboxylic acid compounds of the formula

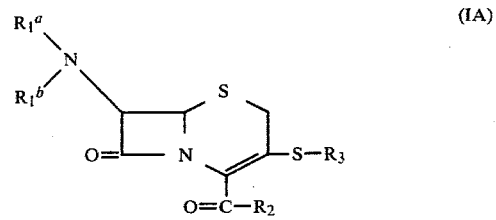

wherein $R_1{}^a$ represents hydrogen or an amino protective group $R_1{}^A$ and $R_1{}^b$ represents hydrogen or an acyl group Ac, or $R_1{}^a$ and $R_1{}^b$ conjointly represent a divalent amino protective group, $R_2$ represents hydroxyl or a radical $R_2{}^A$ which, conjointly with the carbonyl grouping —C(=O)—, forms a protected carboxyl group and $R_3$ represents an unsubstituted or substituted hydrocarbon radical or an unsubstituted or substituted heterocyclic radical, and salts of such compounds with salt-forming groups possess antibiotic properties.

17 Claims, No Drawings

7β-AMINO-3-THIO-3-CEPHEM-4-CARBOXYLIC ACID COMPOUNDS, AND ANTIBACTERIAL COMPOSITIONS AND METHODS USING THEM

The present invention relates to thio derivatives, especially 7β-amino-3-R₃-thio-3-cephem-4-carboxylic acid compounds of the formula

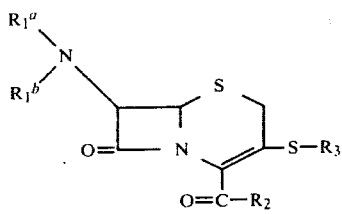

wherein $R_1{}^a$ represents hydrogen or an amino protective group $R_1{}^A$ and $R_1{}^b$ represents hydrogen or an acyl group Ac, or $R_1{}^a$ and $R_1{}^b$ conjointly represent a divalent amino protective group, $R_2$ represents hydroxyl or a radical $R_2{}^A$ which, conjointly with the carbonyl grouping —C(=O)—, forms a protected carboxyl group and $R_3$ represents an optionally substituted hydrocarbon radical or an optionally substituted heterocyclic radical, as well as S-oxides of 3-cephem compounds of the formula IA and also the corresponding 2-cephem compounds of the formula

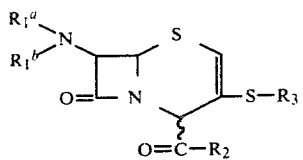

wherein $R_1{}^a$, $R_1{}^b$, $R_2$ and $R_3$ have the abovementioned meanings, and the S-oxides thereof, or salts of such compounds with salt-forming groups, and also processes for their manufacture as well as pharmaceutical preparations containing those compounds which have a pharmacological action and the use thereof.

In 2-cephem compounds of the formula IB with the double bond in the 2,3-position, the optionally protected carboxyl group of the formula —C(=O)—R₂ preferably has the α-configuration.

A divalent amino protective group formed by the radicals $R_1{}^a$ and $R_1{}^b$ conjointly, is especially the divalent acyl radical of an organic dicarboxylic acid, preferably with up to 18 carbon atoms, above all the diacyl radical of an aliphatic or aromatic dicarboxylic acid, as well as the acyl radical of an α-aminoacetic acid which is preferably substituted in the α-position, for example which contains an aromatic or heterocyclic radical, and wherein the amino group is bonded to the nitrogen atom via a methylene radical, which is preferably substituted, for example which contains two lower alkyl groups, such as methyl groups. The radicals $R_1{}^a$ and $R_1{}^b$ conjointly can also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—R₂ᴬ is, above all, an esterified carboxyl group but can also represent an anhydride group, customarily a mixed anhydride group, or an optionally substituted carbamoyl or hydrazinocarbonyl group.

The group $R_2{}^A$ can thus be a hydroxyl group etherified by an organic radical, the organic radical preferably containing up to 18 carbon atoms, which conjointly with the —C(=O)— grouping forms an esterified carboxyl group. Examples of organic radicals of this type are aliphatic, cycloaliphatic, cycloaliphatic-aliphatic, aromatic or araliphatic radicals, especially optionally substituted hydrocarbon radicals of this type, as well as heterocyclic or heterocyclic-aliphatic radicals.

The group $R_2{}^A$ can also represent an organic silyloxy radical as well as a hydroxyl group etherified by an organometallic radical, such as a corresponding organic stannyloxy group, especially a silyloxy or stannyloxy group which is substituted by 1 to 3 optionally substituted hydrocarbon radicals, preferably with up to 18 carbon atoms, such as aliphatic hydrocarbon radicals, and optionally by halogen, such as chlorine.

A radical $R_2{}^A$ which with a —C(=O)— grouping forms an anhydride group, above all a mixed anhydride group, is, for example, halogen, such as chlorine, or an acyloxy radical, wherein acyl represents the corresponding radical of an organic carboxylic acid, preferably with up to 18 carbon atoms, such as an aliphatic, cycloaliphatic, cycloaliphatic-aliphatic, aromatic or araliphatic carboxylic acid, or of a carbonic acid halfderivative, such as a carbonic acid half-ester.

A radical $R_2{}^A$ which with a —C(=O)— grouping forms a carbamoyl group is an optionally substituted amino group, wherein substituents represent optionally substituted monovalent or divalent hydrocarbon radicals, preferably with up to 18 carbon atoms, such as optionally substituted monovalent or divalent aliphatic, cycloaliphatic, cycloaliphatic-aliphatic, aromatic or araliphatic hydrocarbon radicals with up to 18 carbon atoms, as well as corresponding heterocyclic or heterocyclic-aliphatic radicals with up to 18 carbon atoms and/or functional groups, such as optionally functionally modified hydroxyl, but especially free hydroxyl, and also etherified or esterified hydroxyl, wherein the etherifying or esterifying radicals have, for example, the abovementioned meanings and preferably contain up to 18 carbon atoms, as well as acyl radicals, above all those of organic carboxylic acids and of carbonic acid halfderivatives, preferably with up to 18 carbon atoms.

In a substituted hydrazinocarbonyl group of the formula —C(=O)—R₂ᴬ, one or both of the nitrogen atoms can be substituted, possible substituents being above all optionally substituted monovalent or divalent hydrocarbon radicals, preferably with up to 18 carbon atoms, such as optionally substituted, monovalent or divalent, aliphatic, cycloaliphatic, cycloaliphatic-aliphatic, aromatic or araliphatic hydrocarbon radicals with up to 18 carbon atoms, as well as corresponding heterocyclic or heterocyclic-aliphatic radicals with up to 18 carbon atoms, and/or functional groups, such as acyl radicals, above all those of organic carboxylic acids or of carbonic acid half-derivatives, preferably with up to 18 carbon atoms.

An optionally substituted hydrocarbon radical R₃ is preferably a corresponding cycloaliphatic or cycloaliphatic-aliphatic hydrocarbon radical, but especially an optionally substituted aliphatic or aromatic hydrocarbon radical, as well as a corresponding araliphatic hydrocarbon radical. An optionally substituted heterocyclic radical R₃ is bonded to the thio group by one of its carbon atoms and is preferably of aromatic character but can also be partially or completely hydrogenated and contains at least 1 hetero-atom from the group nitrogen, oxygen and sulphur.

The general concepts used in the preceding and following description have, for example, the following meanings:

An aliphatic radical, including the aliphatic radical of a corresponding organic carboxylic acid, as well as a corresponding ylidene radical, is an optionally substituted monovalent or divalent aliphatic hydrocarbon radical, especially lower alkyl, as well as lower alkenyl or lower alkinyl and also lower alkylidene, which can contain, for example, up to 7, preferably up to 4, carbon atoms. Such radicals can be optionally monosubstituted, disubstituted or polysubstituted by functional groups, for example by free, etherified or esterified hydroxyl or mercapto groups, such as lower alkoxy, lower alkenyloxy or lower alkylenedioxy, optionally substituted phenyloxy or phenyl-lower alkoxy, lower alkylthio or optionally substituted phenylthio, phenyl-lower alkylthio, heterocyclylthio or heterocyclyl-lower alkylthio, optionally substituted lower alkoxycarbonyloxy or lower alkanoyloxy, or halogen, and also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, lower alkoxy-carbonylamino, halogen-lower alkoxycarbonylamino, optionally substituted phenyl-lower alkoxycarbonylamino, optionally substituted carbamoylamino, ureidocarbonylamino or guanidinocarbonylamino, and also sulphoamino, which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl, and also optionally substituted ureidocarbonyl or guanidinocarbonyl, or cyano, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be present in the form of a salt, such as in the form of an alkali metal salt.

A divalent aliphatic radical, including the corresponding radical of a divalent aliphatic carboxylic acid, is, for example, lower alkylene or lower alkenylene, which optionally can be monosubstituted, disubstituted or polysubstituted, for example like an abovementioned aliphatic radical, and/or interrupted by hetero-atoms, such as oxygen, nitrogen or sulphur.

A cycloaliphatic or cycloaliphatic-aliphatic radical, including the cycloaliphatic or cycloaliphatic-aliphatic radical in a corresponding organic carboxylic acid or a corresponding cycloaliphatic or cycloaliphatic-aliphatic ylidene radical, is an optionally substituted, monovalent or divalent cycloaliphatic or cycloaliphatic-aliphatic hydrocarbon radical, for example monocyclic, bicyclic or polycyclic cycloalkyl or cycloalkenyl, as well as cycloalkylidene or cycloalkyl-lower alkyl or cycloalkyl-lower alkenyl or cycloalkenyl-lower alkyl or cycloalkenyl-lower alkenyl, as well as cycloalkyl-lower alkylidene or cycloalkenyl-lower alkylidene, wherein cycloalkyl and cycloalkylidene contain, for example, up to 12, such as 3–8, preferably 3–6, ring carbon atoms, whilst cycloalkenyl has, for example, up to 12, such as 3–8, for example 5–8, preferably 5 or 6 ring carbon atoms as well as 1 to 2 double bonds and the aliphatic part of a cycloaliphatic-aliphatic radical can contain, for example, up to 7, preferably up to 4 carbon atoms. The above cycloaliphatic or cycloaliphatic-aliphatic radicals, if desired, can be monosubstituted, disubstituted or polysubstituted, for example by optionally substituted aliphatic hydrocarbon radicals, such as by the abovementioned, optionally substituted lower alkyl groups, or, for example, like the abovementioned aliphatic hydrocarbon radicals, by functional groups.

An aromatic radical, including the aromatic radical of a corresponding carboxylic acid, is an optionally substituted aromatic hydrocarbon radical, for example a monocyclic, bicyclic or polycyclic aromatic hydrocarbon radical, especially phenyl, as well as biphenylyl or naphthyl, which optionally can be monosubstituted, disubstituted or polysubstituted, for example like the abovementioned aliphatic and cycloaliphatic hydrocarbon radicals.

A divalent aromatic radical, for example of an aromatic carboxylic acid, is above all 1,2-arylene, especially 1,2-phenylene, which optionally can be monosubstituted, disubstituted or polysubstituted, for example like the above-mentioned aliphatic and cycloaliphatic hydrocarbon radicals.

An araliphatic radical, including the araliphatic radical in a corresponding carboxylic acid, and also an araliphatic ylidene radical, is, for example, an optionally substituted araliphatic hydrocarbon radical, such as an optionally substituted aliphatic hydrocarbon radical which contains, for example up to three, optionally substituted monocyclic, bicyclic or polycyclic aromatic hydrocarbon radicals, and above all represents phenyl-lower alkyl or phenyl-lower alkenyl, as well as phenyl-lower alkinyl and also phenyl-lower alkylidene, it being possible for such radicals to contain, for example, 1–3 phenyl groups and optionally to be monosubstituted, disubstituted or polysubstituted in the aromatic and/or aliphatic part, for example like the abovementioned aliphatic and cycloaliphatic radicals.

Heterocyclic groups, including those in heterocyclicaliphatic radicals, including heterocyclic or heterocyclic-aliphatic groups in corresponding carboxylic acids, are especially monocyclic, as well as bicyclic or polycyclic, aza-, thia-, oxa-, thiaza-, thiadiaza-, oxaza-, diaza-, triaza- or tetraza-cyclic radicals of aromatic character, as well as corresponding partially or wholly saturated heterocyclic radicals of this type, it being possible for such radicals optionally to be monosubstituted, disubstituted or polysubstituted, for example like the abovementioned cycloaliphatic radicals, The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of a corresponding half-ester, wherein the organic radical of the ester group represents an optionally substituted aliphatic, cycloaliphatic, aromatic or araliphatic hydrocarbon radical or a heterocyclic-aliphatic radical, and is above all the acyl radical of an optionally substituted lower alkyl half-ester of carbonic acid, for example a lower alkyl half-ester of carbonic acid substituted in the α- or β-position, as well as a lower alkenyl, cycloalkyl, phenyl or phenyllower alkyl half-ester of carbonic acid which is optionally substituted in the organic radical. Acyl radicals of a carbonic acid half-ester are also corresponding radicals of lower alkyl half-esters of carbonic acid, in which the lower alkyl part contains a heterocyclic group, for example one of the abovementioned heterocyclic groups of aromatic character, it being possible for both the lower alkyl radical and the heterocyclic group to be optionally substituted. The acyl radical of a carbonic acid-half-derivative can also be an optionally N-substituted carbamoyl group, such as an optionally halogenated N-lower alkylcarbamoyl group.

An etherified hydroxyl group is above all optionally substituted lower alkoxy, wherein substituents represent above all free or functionally modified, such as etherified or esterified, hydroxyl groups, especially lower alkoxy or halogen, as well as lower alkenyloxy, cycloalkoxy or optionally substituted phenyloxy, and also heterocyclyloxy or heterocyclyl-lower alkoxy, especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl as well as n-pentyl, isopentyl, n-hexyl, isohexyl or n-heptyl, whilst lower alkenyl can be, for example, vinyl, allyl, isopropenyl, 2- or 3-methallyl or 3-butenyl, lower alkinyl can be, for example, propargyl or 2-butinyl and lower alkylidene can be, for example, isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by heteroatoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or cycloalkyl-lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or cycloalkenyl-lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, cyclohexylmethylene and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example corresponding monocyclic, monoaza-, monothia- or monooxa-cyclic radicals, such as pyrryl, for example 2-pyrryl or 3-pyrryl, pyridyl, for example 2-, 3- or 4-pyridyl, and also pyridinium, thienyl, for example 2- or 3-thienyl, or furyl, for example 2-furyl, bicyclic monoaza-, monooxa- or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diaza-, triaza-, tetraza-, oxaza-, thiaza- or thiadiaza-cyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl or 1,2,4- or 1,3,4-thiadiazolyl, for example 1,2,4-thiadiazol-3-yl or 1,3,4-thiadiazol-2-yl, or bicyclic diaza-, oxaza- or thiaza-cyclic radicals, such as benzimidazolyl, for example 2-benzimidazolyl, benzoxazolyl, for example 2-benzoxazolyl or benzthiazolyl, for example 2-benzthiazolyl. Corresponding partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl which contain heterocyclic groups, especially the abovementioned heterocyclic groups. The abovementioned heterocyclyl radicals can be substituted, for example by optionally substituted aliphatic or aromatic hydrocarbon radicals, especially lower alkyl, such as methyl, or phenyl which is optionally substituted, for example by halogen, such as chlorine, for example phenyl or 4-chlorophenyl, or by functional groups, for example like the aliphatic hydrocarbon radicals.

Lower alkoxy is, for example, methoxy, ethoxy, n-propoxy, isopropoxy, n-butoxy, isobutoxy, sec.-butoxy, tert.-butoxy, n-pentyloxy or tert.-pentyloxy. These groups can be substituted, for example as in halogeno-lower alkoxy, especially 2-halogeno-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxy-diphenylmethoxy, and heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio and phenyl-lower alkylthio is, for example, benzylthio, whilst mercapto groups etherified by heterocyclyl radicals or heterocyclylaliphatic radicals are especially pyridylthio, for example 4-pyridylthio, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentyloxycarbonyl.

N-lower alkylcarbamoyl or N,N-di-lower alkylcarbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium salt or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino and aza-lower alkyleneamino is, for example, piperazino or 4-methylpiperazino. Acylamino represents especially carbamoylamino, lower alkylcarbamoylamino, such as methylcarbamoylamino, ureidocarbonylamino, 3,5-dioxo-2,3,4,5-tetrahydro-1,2,4-triazin-6-yl-carbonylamino, guanidinocarbonylamino, lower alkoxycarbonylamino, for example methoxycarbonylamino, ethoxycarbonylamino or tert.-butoxycarbonylamino, halogeno-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino, which is optionally present in the form of a salt, such as an alkali metal salt, for example a sodium salt or an ammonium salt.

Lower alkanoyl is, for example, formyl, acetyl, propionyl or pivaloyl.

O-Lower alkyl-phosphono is, for example O-methyl-phosphono or O-ethyl-phosphono, O,O'-di-lower alkyl phosphono is, for example, O,O'-dimethyl-phosphono or O,O'-diethylphosphono, O-phenyl-lower alkyl-phosphono is, for example, O-benzyl-phosphono and O-lower alkyl-O'-phenyl-lower alkylphosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxybenzyloxycarbonyl, diphenylmethoxycarbonyl or α-4-biphenylyl-α-methyl-ethoxycarbonyl. Lower alkoxycarbonyl wherein lower alkyl contains, for example, a monocyclic monoaza-, monooxa- or monothia-cyclic group is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino is, for example, 2-methylhydrazino or 2,2-dimethylhydrazino, 2-lower alkoxycarbonylhydrazino is, for example, 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a naturally occurring or biosynthetically, semi-synthetically or total-synthetically obtainable, preferably pharmacologically active, N-acyl derivative of 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

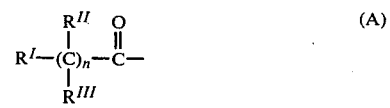

(A)

wherein n represents O and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ denotes hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character, $R^{II}$ denotes an optionally functionally modified, for example esterified or etherified, hydroxyl or mercapto group, such as a halogen atom, an optionally substituted amino group, an optionally functionally modified carboxyl or sulpho group, an optionally O-monosubstituted or O,O'-disubstituted phosphono group or an azido group and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character, and the two radicals $R^{II}$ and $R^{III}$ conjointly represent a hydroxyimino group which is etherified by an aliphatic, cycloaliphatic or aromatic hydrocarbon radical and which is preferably in the syn-configuration.

In the abovementioned acyl groups of the formula A, for example, n represents O and $R^I$ represents hydrogen or a cycloalkyl group with 5–7 ring carbon atoms which is optionally substituted, preferably in the 1-position, by optionally protected amino, acylamino, wherein acyl above all represents the acyl radical of a carbonic acid half-ester, such as a lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or by halogen, for example chlorine, a heterocyclic group which is optionally substituted, for example by lower alkyl, for example methyl, and/or phenyl, which in turn can carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or n represents 1, $R^I$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaning, and/or halogen, for example chlorine, or a lower alkyl group which is substituted by optionally protected amino and/or carboxyl, for example a 3-amino-3-carboxypropyl radical which has an optionally protected amino and/or carboxyl group, for example a silylated, such as tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group or an esterified carboxyl group, such as a carboxyl group which is esterified by lower alkyl, 2-halogeno-lower alkyl or phenyl-lower alkyl, for example diphenylmethyl, or represents a lower alkenyl group, a phenyl group which is optionally substituted, such as a phenyl group which optionally contains hydroxyl which is acylated, for example as indicated above, and/or halogen, for example chlorine, and also amino-lower alkyl, such as aminomethyl, which is optionally protected, for example acylated as indicated above, or contains optionally substituted phenyloxy such as phenyloxy which possesses hydroxyl which is optionally acylated, for example as indicated above, and/or halogen, for example chlorine, or represents a pyridyl group, for example a 4-pyridyl group, pyridinium group, for example a 4-pyridinium group, thienyl group, for example a 2-thienyl or 5-aminomethylthien-2-yl group, furyl group, for example a 2-furyl group, imidazolyl group, for example a 1-imidazolyl group, or tetrazolyl group, for example a 1-tetrazolyl group, which are optionally substituted, for example by lower alkyl, such as methyl, or by amino or aminomethyl, which are optionally protected, for example acylated as indicated above, or represents an optionally substituted lower alkoxy group, for example a methoxy group, a phenyloxy group which is optionally substituted, such as a phenyloxy group which contains optionally protected hydroxyl, for example hydroxyl acylated as indicated above, and/or halogen, such as chlorine, or represents a lower alkylthio group, for example a N-butylthio group, or lower alkenylthio group, for example an allylthio group, a phenylthio, pyridylthio, for example 4-pyridylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadazol-3-ylthio, 1,3,4-thiadiazol-2-ylthio, such as 5-methyl-1,3,4-thiadiazol-2-ylthio or 5-tetrazolylthio, such as 1-methyl-5-tetrazolylthio group, which are optionally substituted, for example by lower alkyl, such as methyl, or represents a halogen atom, especially a chlorine or bromine atom, an optionally functionally modified carboxyl group, such as lower alkoxycarbonyl, for example methoxycarbonyl or ethoxycarbonyl, cyano or carbamoyl which is optionally N-substituted, for example by lower alkyl, such as methyl, or phenyl, or represents an optionally substituted lower alkanoyl group, for example an acetyl or propionyl group, or a benzoyl group, or an azido group, and $R^{II}$ and $R^{III}$ represent hydrogen, or n represents 1, $R^I$ represents lower alkyl or a phenyl, furyl, for example 2-furyl, thienyl, for example 2- or 3-thienyl, or isothiazolyl, for example 4-isothiazolyl group which is optionally substituted, such as substituted by hydroxyl which is optionally acylated, for example as indicated above, and/or by halogen, for example chlorine, and also represents a 1-cyclohexenyl or 1,4-cyclohexadienyl group, $R^{II}$ represents optionally protected or substituted amino, for example amino, acylamino, such as lower alkoxycarbonylamino, 2-halogeno-lower alkoxycarbonylamino or optionally substituted phenyl-lower alkoxycarbonylamino, such as phenyl-lower alkoxycarbonylamino which contains lower alkoxy, for example methoxy, or nitro, for example tert.-butoxycarbonylamino, 2,2,2-trichloroethoxycarbonylamino, 4-methoxybenzyloxycarbonylamino or diphenylmethoxycarbonylamino, heterocyclylcarbonylamino, wherein heterocyclyl is a six-membered ring with 1 to 3 nitrogen atoms which is optionally substituted by 1 to 2 hydroxyl groups, for example 3,5-dioxo-2,3,4,5-tetrahydro-1,2,4-triazin-6-yl-carbonylamino, arylsulphonylamino, for example 4-methylphenylsulphonylamino, tritylamino, arylthioamino, such as nitrophenylthioamino, for example 2-nitrophenylthioamino, or tritylthioamino or 2- propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylidenamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in a protected form, such as in an esterified form, for example as a lower alkoxycarbonyl group, for example a methoxycarbonyl or ethoxycarbonyl group, or as a phenyloxycarbonyl group, for example a diphenylmethoxycarbonyl group, a cyano group, a sulpho group, an optionally functionally modified hydroxyl group, wherein functionally modified hydroxyl in particular represents acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy, or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1, $R^I$ represents a phenyl, furyl, for example 2-furyl, or thienyl, for example 2- or 3-thienyl, or isothiazolyl, for example a 4-isothiazolyl group, which are optionally substituted, for example by hydroxyl which is optionally acylated, for example as indicated above, and/or by halogen, for example chlorine, and also represents a 1,4-cyclohexadienyl group, $R^{II}$ represents aminomethyl which is optionally protected, for example as indicated above, and $R^{III}$ represents hydrogen or n represents 1 and each of the groups $R^I$, $R^{II}$ and $R^{III}$ represents lower alkyl, for example methyl, or n represents 1, $R^I$ represents phenyl, furyl or thienyl and $R^{II}$ and $R^{III}$ conjointly represent a hydroxyimino group which is etherified by lower alkyl, cycloalkyl or phenyl and which is preferably in the syn-configuration.

Such acyl radicals Ac are, for example, formyl, cyclopentylcarbonyl, α-aminocyclopentylcarbonyl or α-amino-cyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or by reduction, for example on treatment with a chemical reducing agent, such as zinc in the presence of aqueous acetic acid, or catalytic hydrogen, or hydrolytically, or an acyl radical which can be converted into such a radical, preferably a suitable acyl radical of a carbonic acid half-ester, such as lower alkoxycarbonyl, for example tert.-butoxycarbonyl, 2-halogeno-lower alkylcarbonyl, for example 2,2,2-trichloroethoxycarbonyl, 2-bromoethoxycarbonyl or 2-iodoethoxycarbonyl, arylcarbonylmethoxycarbonyl, for example phenacyloxycarbonyl, optionally substituted phenyl-lower alkoxycarbonyl, such as phenyl-lower alkoxycarbonyl containing lower alkoxy, for example methoxy, or nitro, for example 4-methoxybenzyloxycarbonyl or diphenylmethoxycarbonyl, or of a carbonic acid half-amide, such as carbamoyl or N-substituted carbamoyl, such as N-lower alkylcarbamoyl, for example N-methylcarbamoyl, as well as by trityl, also by arylthio, for example 2-nitrophenylthio, arylsulphonyl, for example 4-methylphenylsulphonyl or 1-lower alkoxycarbonyl-2-propylidene, for example 1-ethoxycarbonyl-2-propylidene), 2,6-dimethoxybenzoyl, 5,6,7,8-tetrahydronaphthoyl, 2-methoxy-1-naphthoyl, 2-ethoxy-1-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonoyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxy-valeryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methy or ethyl ester, or an aryl-lower alkyl ester, for example a diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromo-phenylacetyl, α-azido-phenylacetyl, 3-chlorophenylacetyl, 2- or 4-aminomethylphenylacetyl (with an amino group which is optionally substituted, for example as indicated), phenacylcarbonyl, phenyloxyacetyl, 4-trifluoromethylphenoxyacetyl, benzyloxyacetyl, phenylthioacetyl, bromophenylthioacetyl, α-phenyloxypropionyl, α-phenyloxyphenylacetyl, α-methoxyphenylacetyl, α-ethoxyphenylacetyl, α-methoxy-3,4-dichlorophenylacetyl, α-cyanophenylacetyl, phenylglycyl, 4-hydroxyphenylglycyl, 3-chloro-4-hydroxy-phenylglycyl, 3,5-dichloro-4-hydroxyphenylglycyl, α-amino-α-(1,4-cyclohexadienyl)-acetyl, α-amino-α-(1-cyclohexenyl)-acetyl, α-(3,5-dioxo-2,3,4,5-tetrahydro-1,2,4-triazin-6-yl-carbonylamino)-α-phenylacetyl, α-aminomethyl-α-phenylacetyl or α-hydroxyphenylacetyl (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or a α-O-methylphosphono-phenylacetyl or α-O,O-dimethyl-phosphonophenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-amino-pyridiniumacetyl (optionally with an amino group which is substituted, for example as indicated above), 2-thienylacetyl, 3-thienylacetyl, 5-aminomethylthien-2-yl-acetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2'-furyl)-acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolyl-thioacetyl, 1,2,4-triazol-3-yl-thioacetyl, 1,3,4-triazol-2-ylthioacetyl, 5-methyl-1,2,4-thiadiazol-3-ylthioacetyl, 5-methyl-1,3,4-thiadiazol-2-ylthioacetyl, 1-methyl-5-tetrazolylthioacetyl, 2-(2-furyl)-2-syn-methoxyiminoacetyl, 2-(2-thienyl)-2-syn-methoxyiminoacetyl, 2-(2-furyl)-2-syn-phenoxyiminoacetyl, 2-phenyl-2-syn-methoxyiminoacetyl, 2-phenyl-2-syn-phenoxyiminoacetyl, 2-(2-furyl)-2-syn-cyclopentoxyiminoacetyl, 2-phenyl-2-syn-ethoxyiminoacetyl or 2-(2-thienyl)-2-syn-tert.-butoxyiminoacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentyloxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyllower alkoxycarbonyl, above all α-phenyl-lower alkoxycarbonyl, wherein the α-position is preferably polysubstituted, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A divalent acyl group formed by the two radicals $R_1^A$ and $R_1^b$ is, for example, the acyl radical of a lower alkanedicarboxylic acid or a lower alkenedicarboxylic acid, such as succinyl, or of a o-arylenedicarboxylic acid, such as phthaloyl.

A further divalent radical formed by the groups $R_1^A$ and $R_1^b$ is, for example, a 1-oxo-3-aza-1,4-butylene radical which is substituted, especially in the 2-position, and contains, for example, optionally substituted phenyl or thienyl, and is optionally monosubstituted or disubstituted in the 4-position by lower alkyl, such as methyl, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping, an esterified carboxyl group which can be split easily on treatment with chemical reducing agents under neutral or weakly acid conditions, for example with zinc in the presence of aqueous acetic acid, or an esterified carboxyl group which can easily be converted into such a group, and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=O)— grouping represents an esterified carboxyl group which can be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group, wherein aryl in particular denotes a monocyclic, preferably substituted, aromatic hydrocarbon radical. Such a radical forms, together with the —C(=O)— grouping, an esterified carboxyl group which can be split easily on irradiation, preferably with ultraviolet light, under neutral or acid conditions. An aryl radical in such an arylmethoxy group is especially lower alkoxyphenyl, for example methoxyphenyl (wherein methoxy above all is in the 3-, 4- and/or 5-position), and/or above all nitrophenyl (wherein nitro is preferably in the 2-position). Such radicals are, in particular, lower alkoxy-, for example methoxy-, and/or nitro-benzyloxy, above all 3- or 4-methoxybenzyloxy, 3,5-dimethoxybenzyloxy, 2-nitrobenzyloxy or 4,5-dimethoxy-2-nitrobenzyloxy.

An etherified hydroxyl group $R_2^A$ can also represent a radical which, together with the —C(=O)— grouping, forms an esterified carboxyl group which can be split easily under acid conditions, for example on treatment with trifluoroacetic acid or formic acid. Such a radical is above all a methoxy group, in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this type are tert.-lower alkoxy, for example tert.-butoxy or tert.-pentyloxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxy-phenyl-lower alkoxy, such as 4-methoxybenzyloxy or 3,4-dimethoxy-benzyloxy, or furfuryloxy, such as 2-furfuryloxy. A polycycloaliphatic hydrocarbon radical, in which methyl of the methoxy group represents a branched, preferably triply branched, ring member, is, for example, adamantyl, such as 1-adamantyl, and an abovementioned oxacycloaliphatic or thiacycloaliphatic radical wherein methyl of the methoxy group is the ring member which represents the α-position to the oxygen or sulphur atom, denotes, for example, 2-oxa- or 2-thia-lower alkylene or -lower alkenylene with 5–7 ring atoms, such as 2-tetrahydrofuryl, 2-tetrahydropyranyl or 2,3-dihydro-2-pyranyl or corresponding sulphur analogues.

The radical $R_2^A$ can also represent an etherified hydroxyl group which, together with the —C(=O)— grouping, forms an esterified carboxyl group which can be split hydrolytically, for example under weakly basic or weakly acid conditions. Such a radical is preferably an etherified hydroxyl group which forms an activated ester group with the —C=O— grouping, such as nitrophenyloxy, for example 4-nitrophenyloxy or 2,4-dinitrophenyloxy, nitrophenyl-lower alkoxy, for example 4-nitrobenzyloxy, hydroxy-lower alkyl-benzyloxy, for example 4-hydroxy-3,5-tert.-butyl-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

Benzyloxy groups containing nitro groups, especially the 4-nitrobenzyloxy group, can also first be converted by reduction with an agent which reduces a nitro group to a hydroxylamino or amino group, such as a hydrosulphite, for example sodium hydrosulphite ($Na_2S_2O_4$), into a hydroxylamino or amino group, after which hydrolytic splitting takes place.

The group $R_2^A$ can also represent an etherified hydroxyl group which, together with the carbonyl grouping of the formula —C(=O)—, forms an esterified carboxyl group which can be split under hydrogenolytic conditions, and is, for example, α-phenyl-lower alkoxy which is optionally substituted, for example by lower alkoxy or nitro, such as benzyloxy, 4-methoxy-benzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all an acylmethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoylmethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains as substituents optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, and represents above all tri-lower alkylsilyloxy, for example trimethylsilyloxy, halogeno-lower alkoxy-lower alkylsilyl, for example chloro-methoxy-methyl-silyl, or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy which is optionally substituted, such as by halogen, for example fluorine or chlorine, preferably is the α-position, for example acetoxy, pivalyloxy or trichloroacetoxy, or lower alkoxycarbonyloxy, for example methoxycarbonyloxy or ethoxycarbonyloxy.

A radical $R_2^A$ which, together with a —C(=O)— grouping, forms an optionally substituted carbamoyl or hydrazinocarbonyl group is, for example, amino, lower alkylamino or di-lower alkylamino, such as methylamino, ethylamino, dimethylamino or diethylamino, lower alkyleneamino, for example pyrrolidino or piperidino, or oxa-lower alkyleneamino, for example morpholino, hydroxyamino, hydrazino or 2-lower alkylhydrazino or 2,2-di-lower alkylhydrazino, for example 2-methylhydrazino or 2,2-dimethylhydrazino.

An optionally substituted aliphatic hydrocarbon radical $R_3$ is, in particular, lower alkyl with up to 7, preferably up to 4, carbon atoms, such as methyl, ethyl, n-propyl, isopropyl, n-butyl, isobutyl or sec.-butyl, and also lower alkenyl, for example, allyl, optionally protected amino-lower alkyl or tert.-amino-lower alkyl, wherein the tert.-amino group is separated from the sulphur atom by at least two carbon atoms, such as 2- or 3-amino-lower alkyl, for example 2-amino-ethyl or 3-amino-propyl, 2- or 3-di-lower alkylamino-lower alkyl, for example 2-dimethylaminoethyl, 2-diethylaminoethyl or 3-dimethylaminopropyl, or etherified hydroxy-lower alkyl, wherein the etherified hydroxy group, in particular lower alkoxy, is separated from the sulphur atom by at least two carbon atoms, such as 2- or 3-lower alkoxy-lower alkyl, for example 2-methoxy-ethyl or 2-ethoxy-ethyl, or carbo-lower alkoxy-lower alkyl, such as carbomethoxymethyl or carboethoxymethyl, or halogenomethyl, such as trifluoromethyl.

An optionally substituted aromatic hydrocarbon radical $R_3$ is above all phenyl, which can be substituted by 1 or more lower alkyl groups, such as methyl, aryl groups such as phenyl, lower alkoxy groups, such as methoxy, or halogen, such as fluorine, chlorine or bromine.

An optionally substituted araliphatic hydrocarbon radical $R_3$ is above all an optionally substituted phenyl-lower alkyl radical, especially a 1-phenyl-lower alkyl radical, with 1–3 optionally substituted phenyl radicals, such as benzyl, diphenylmethyl or trityl, possible substituents being, for example, esterified or etherified hydroxyl, such as halogen, for example fluorine, chlorine or bromine, or lower alkoxy, such as methoxy.

An optionally substituted heterocyclic radical $R_3$, which is bonded to the thio group by one of its carbon atoms, is above all an aromatic heterocyclic structure with 1 to 4 nitrogen atoms and/or an oxygen or a sulphur atom, possible substituents being lower alkyl, such as methyl, lower alkoxy, such as methoxy, or halogen, such as fluorine or chlorine, such as pyridyl, for example 4-pyridyl, 2-imidazolyl, 1,2,4-triazol-3-yl, 1,3,4-triazol-2-yl, 1,2,4-thiadiazol-3-yl, 5-methyl-1,2,4- thiadiazol-3-yl, 1,3,4-thiadiazol-2-yl, 5-methyl-1,3,4-thiadiazol-2-yl, 5-tetrazolyl or 1-methyl-5-tetrazolyl.

S-oxides of compounds of the formula IA and IB are above all mono-S-oxides, especially 1-oxides, and also 3-S(→O)-$R_3$ compounds and di-S-oxides, that is to say 1-oxide-3-S(→O)-$R_3$ compounds, as well as mixtures thereof.

Salts are, in particular, those of compounds of the formulae IA and IB having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneimines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or 4-methylphenylsulphonic acid. Compounds of the formulae IA and IB having an acid group and a basic group can also be in the form of inner salts, that is to say in the form of a zwitterion. S-Oxides of compounds of the formula IA and IB having salt-forming groups can also form salts, as described above.

The new compounds of the present invention possess valuable pharmacological properties or can be used as intermediate products for the manufacture of such compounds. Compounds of the formula IA wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ conjointly represent a 1-oxo-3-aza-1,4-butylene radical which is preferably substituted in the 2-position, for example by an aromatic or heterocyclic radical, and preferably substituted in the 4-position, for example by 2 lower alkyls, such as methyl, and $R_2$ denotes hydroxyl or an etherified hydroxyl group $R_2^A$ which, together with the carbonyl group, forms an esterified carboxyl group which can be split easily under physiological conditions, and $R_3$ has the abovementioned meaning and functional groups which may be present in an acyl radical $R_1^a$, such as amino, carboxyl, hydroxyl and/or sulpho, are usually in the free form, or pharmacologically acceptable salts of such compounds with salt-forming groups are of low toxicity and are active in vitro, in a dosage range from about 0.02 mcg/ml to about 100 mcg/ml, against Gram-positive and Gram-negative germs, as well as against Mycobacterium tuberculosis, as well as in vivo, on parenteral and/or oral administration, against microorganisms, such as Gram-positive bacteria, for example *Staphylococcus aureus*, (for example in mice in doses of about 0.0014 to about 0.023 g/kg subcutaneously or of about 0.003 to about 0.025 g/kg perorally) and Gram-negative bacteria, for example *Escherichia coli*, (for example in mice in doses of about 0.007 to about 0.09 g/kg subcutaneously or perorally), and especially against penicillin-resistant bacteria, such as *Staphylococcus aureus*. These new compounds can thus be used, for example in the form of preparations which have an antibiotic action and which can be administered parenterally or orally, for the treatment of corresponding infections.

Compounds of the formula IB or S-oxides of compounds of the formula IA and IB, wherein $R_1^a$, $R_1^b$, $R_2$ and $R_3$ have the meanings indicated in the context of formula IA, or compounds of the formula IA wherein $R_3$ has the abovementioned meaning and the radicals $R_1^a$ and $R_1^b$ represent hydrogen, or $R_1^a$ denotes an amino protective group different from an acyl radical occurring in pharmacologically active N-acyl derivatives of 6-β-amino-penam-3-carboxylic acid compounds or 7β-amino-3-cephem-4-carboxylic acid compounds and $R_1^b$ denotes hydrogen, or $R_1^a$ and $R_1^b$ conjointly represent a divalent amino protective group different from a 1-oxo-3-aza-1,4-butylene radical which is preferably substituted in the 2-position, for example by an aromatic or heterocyclic radical, and preferably substituted in the 4-position, for example by 2 lower alkyls, such as methyl, and $R_2$ represents hydroxyl, or $R_1^a$ and $R_1^b$ have the abovementioned meanings, $R_2$ represents a radical $R_2^A$ which together with the —C(=O)— grouping forms a protected carboxyl group which can preferably be split easily, a carboxyl group protected in this way being different from a carboxyl group which can be split physiologically, and $R_3$ has the abovementioned meanings, are valuable intermediate products, which can be converted in a simple manner, for example as is described below, into the abovementioned pharmacologically active compounds.

The invention in particular relates to 3-cephem compounds of the formula IA, wherein $R_1^a$ denotes hydrogen or preferably an acyl radical contained in a fermentatively obtainable, that is to say naturally occurring, or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula A, in which $R^I$, $R^{II}$, $R^{III}$ and n above all have the preferred meanings, $R_1^b$ represents hydrogen, or wherein $R_1^a$ and $R_1^b$ conjointly represent a 1-oxo-3-aza-1,4-butylene radical which is preferably substituted in the 2-position, for example by an aromatic or heterocyclic radical, such as phenyl, and preferably substituted in the 4-position, for example by two lower alkyl, such as methyl, $R_2$ represents hydroxyl, lower alkoxy which is optionally mono-substituted or polysubstituted preferably in the α-position, for example by optionally substituted aryloxy, such as lower alkoxyphenyloxy, for example 4-methoxyphenyloxy, lower alkanoyloxy, for example acetoxy or pivaloyloxy, α-amino-lower alkanoyloxy, for example glycyloxy, L-valyloxy, or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or is optionally monosubstituted or polysubstituted in the β-position by halogen, for example chlorine, bromine or iodine, such as lower alkoxy, for example methoxy, ethoxy, n-propoxy, isopropoxy, n-butoxy, tert.-butoxy or tert.-pentyloxy, bisphenyloxy-methoxy which is optionally substituted by lower alkoxy, for example bis-4-methoxyphenyloxy-methoxy, lower alkanoyloxy-methoxy, for example acetoxymethoxy or pivaloyloxymethoxy, α-amino-lower alkanoyloxy-methoxy, for example glycyloxymethoxy, phenacyloxy, optionally substituted phenyl-lower alkoxy, especially 1-phenyl-lower alkoxy, such as phenylmethoxy, it being possible for such radicals to contain 1–3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy, or 2-halogeno-lower alkoxy, for example 2,2,2-trichloroethoxy, 2-chloroethoxy, 2-bromoethoxy or 2-iodoethoxy, and also represents 2-phthalidyloxy, as well as acyloxy, such as lower alkoxycarbonyloxy, for example methoxyarbonyloxy or ethoxycarbonyloxy, or lower alkanoyloxy, for example acetoxy or pivaloyloxy, tri-lower alkylsilyloxy, for example trimethylsilyloxy, or amino or hydrazino which is optionally substituted, for example by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxyamino, and R$_3$ represents lower alkyl, for example methyl, ethyl, n-propyl, isopropyl or n-butyl, 2-amino-lower alkyl, such as 2-aminoethyl, carbo-lower alkoxy-lower alkyl, such as carbomethoxymethyl, lower alkenyl, for example allyl, phenyl or phenyl which is optionally substituted by methyl, methoxy, fluorine or chlorine, optionally substituted phenyl-lower alkyl, especially 1-phenyl-lower alkyl with 1 to 3 phenyl radicals which are optionally substituted, for example by lower alkoxy, such as methoxy, for example benzyl, diphenylmethyl or trityl, or an aromatic heterocyclic radical which has 1 to 4 nitrogen atoms and/or an oxygen or sulphur atom and which is optionally substituted by lower alkyl, lower alkoxy or halogen, as well as the 1-oxides thereof, and also the corresponding 2-cephem compounds of the formula IB, or salts of such compounds with salt-forming groups.

Above all, in a 3-cephem compound of the formula IA, as well as in a corresponding 2-cephem compound of the formula IB, and also a 1-oxide thereof, or in a salt of such a compound having salt-forming groups, $R_1{}^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, especially an acyl radical of the formula A, wherein $R^I$, $R^{II}$, $R^{III}$ and n above all have the preferred meanings, such as a phenylacetyl or phenyloxyacetyl radical which is optionally substituted, for example by hydroxyl, also a lower alkanoyl or lower alkenoyl radical which is optionally substituted, for example by lower alkylthio, or lower alkenylthio, as well as by optionally substituted, such as acylated, amino and/or functionally modified, such as esterified, carboxyl, for example 4-hydroxy-phenylacetyl, hexanoyl, octanoyl or n-butyl-thioacetyl, and especially 5-amino-5-carboxy-valeryl, wherein the amino and/or the carboxyl groups are optionally protected and are present, e.g., respectively as acylamino or esterified carboxyl, or phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, especially an acyl radical of the formula A, wherein $R^I$, $R^{II}$, $R^{III}$ and n above all have the preferred meanings, such as formyl, 2-halogenoethylcarbamoyl, for example 2-chloroethylcarbamoyl, cyanoacetyl, phenylacetyl, thienylacetyl, for example 2-thienylacetyl, or 5-amino-methylthien-2-yl-acetyl, or tetrazolylacetyl, for example 1-tetrazolylacetyl, or acetyl substituted in the α-position by a cyclic, such as a cycloaliphatic, aromatic or heterocyclic, above all monocyclic, radical and by a functional group, above all amino, carboxyl, sulpho or hydroxyl groups, such as phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl, or 3- or 4-hydroxyphenyl, 3-chloro-4-hydroxyphenyl or 3,5-dichloro-4-hydroxyphenyl (optionally also with a protected, such as acylated, hydroxyl group), and wherein the amino group can also optionally be substituted and represents, for example, a sulphoamino group, which is optionally present in the form of a salt, or an amino group which contains, as substituents, a hydrolytically removable trityl group or, above all, an acyl group, such as an optionally substituted carbamoyl group, such as an optionally substituted ureidocarbonyl group, for example ureidocarbonyl or N'-trichloromethylureidocarbonyl, or an optionally substituted triazinylcarbonyl group, such as 3,5-dioxo-2,3,4,5-tetrahydro-1,2,4-triazin-6-yl-carbonyl, or an optionally substituted guanidinocarbonyl group, for example guanidinocarbonyl, or an acyl radical which can be split off, preferably easily, for example on treatment with an acid agent, such as trifluoroacetic acid, or reductively, such as on treatment with a chemical reducing agent, such as zinc in the presence of aqueous acetic acid, or with catalytic hydrogen, or hydolytically, or an acyl radical which can be converted into such a radical, preferably a suitable acyl radical of a carbonic acid half-ester, such as one of the abovementioned, for example optionally halogen-substituted or benzoyl-substituted lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl, or phenacyloxycarbonyl, optionally lower alkoxy-substituted or nitro-substituted phenyl-lower alkoxycarbonyl, for example 4-methoxybenzyloxycarbonyl or diphenylmethoxycarbonyl, or a suitable acyl radical of a carbonic acid half-amide, such as carbamoyl or N-methylcarbamoyl, or an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl-2-propylidene or 1-lower alkanoyl-2-propylidene radical which can be split off with an acid agent, such as formic acid or aqueous mineral acid, for example hydrochloric acid or phosphoric acid, for example 1-ethoxycarbonyl-2-propylidene, and also α-(1,4-cyclohexadienyl)-glycol, α-(1-cyclohexenyl)-glycyl, α-thienylglycyl, such as α-2-thienylglycyl or α-3-thienylglycyl, α-furylglycyl, such as α-2-furylglycyl, α-isothiazolylglycyl, such as α-4-isothiazolyl-glycyl, it being possible for the amino group in such radicals to be substituted or protected, for example as indicated for a phenylglycyl radical, also α-carboxy-phenylacetyl or α-carboxy-thienylacetyl, for example α-carboxy-2-thienylacetyl (optionally with a functionally modified carboxy group, for example a carboxyl group present in the form of a salt, such as a sodium salt, or in the form of an ester, such as a lower alkyl ester, for example a methyl or ethyl ester, or a phenyl-lower alkyl ester, for example a diphenylmethyl ester), α-sulpho-phenylacetyl (optionally also with a sulpho group which is functionally modified, for example like the carboxyl group), α-phosphono-, α-O-methylphosphono- or α-O,O'-dimethylphosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid-half-ester, such as one of the abovementioned, for example a lower alkoxycarbonyl radical which is optionally substituted by halogen or benzoyl, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), as well as 1-amino-cyclohexylcarbonyl, aminomethylphenylacetyl, such as 2- or 4-aminomethyl-phenylacetyl, or amino-pyridiniumacetyl, for example 4-aminopyridiniumacetyl (optionally also with an amino group which is substituted, for example as indicated above), or pyridylthioacetyl, for example 4-pyridylthioacetyl, or 2-(2-furyl)-2-syn-methoxy-iminoacetyl, 2-(2-thienyl)-2-syn-methoxyiminoacetyl, 2-(2-furyl)-2-syn-phenoxyiminoacetyl, 2-phenyl-2-syn-methoxyiminoacetyl, 2-phenyl-2-syn-phenoxyiminoacetyl, 2-(2-furyl)-2-syn-cyclopentoxyiminoacetyl, 2-phenyl-2-syn-ethoxyiminoacetyl or 2-(2-thienyl)-2-syn-tert.-butoxyiminoacetyl, and $R_1^b$ represents hydrogen, or $R_1^a$ and $R_1^b$ conjointly represent a 1-oxo-3-aza-1,4-butylene radical which is optionally substituted, preferably in the 2-position, by protected hydroxyl, such as acyloxy, for example optionally halogen-substituted lower alkoxycarbonyloxy or lower alkanoyloxy, and/or by phenyl which is substituted by halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl (optionally also with a hydroxyl group which is protected, for example acylated as indicated above), and which optionally contains two lower alkyls, such as methyl, in the 4-position, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy, or 2-chloroethoxy or 2-bromoethoxy, which can easily be converted into 2-iodoethoxy, phenacyloxy, 1-phenyl-lower alkoxy with 1-3 phenyl radicals, which are optionally substituted by lower alkoxy or nitro, for example 4-methoxybenzyloxy, 4-nitrobenzyloxy, diphenylmethoxy, 4,4'-dimethoxy-diphenylmethoxy or trityloxy, lower alkanoyloxy-methoxy, for example acetoxymethoxy or pivaloyloxymethoxy, α-amino-lower alkanoylmethoxy, for example glycyloxymethoxy, 2-phthalidyloxymethoxy, lower alkoxycarbonyloxy, for example ethoxycarbonyloxy, or lower alkanoyloxy, for example acetoxy, and also tri-lower alkylsilyloxy, for example trimethylsilyloxy, and $R_3$ represents, above all, lower alkyl, for example methyl, ethyl or n-butyl, 2-amino-lower alkyl, such as 2-aminoethyl, carbo-lower alkoxy-lower alkyl, such as carbomethoxymethyl, and phenyl as well as lower alkenyl, for example allyl, and also 1-phenyl-lower alkyl, for example benzyl, diphenylmethyl or trityl, but also an aromatic heterocyclic radical which has 1 to 4 nitrogen atoms and/or an oxygen or sulphur atom and which is optionally substituted by lower alkyl, lower alkoxy or halogen, such as 1-methyl-5-tetrazolyl.

The invention relates above all to 3-cephem compounds of the formula IA, wherein $R_1^a$ denotes hydrogen, cyanoacetyl or an acyl group of the formula

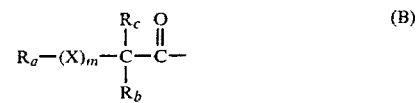

wherein $R_a$ denotes phenyl or hydroxyphenyl, for example 3- or 4-hydroxyphenyl, also hydroxy-chlorophenyl, for example 3-chloro-4-hydroxyphenyl or 3,5-dichloro-4-hydroxyphenyl, it being possible for hydroxy substituents in such radicals to e protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, 5-aminomethyl-2-thienyl and also pyridyl, for example 4-pyridyl, aminopyridinium, for example 4-aminopyridinium, furyl, for example 2-furyl, isothiazolyl, for example 4-isothiazolyl, or tetrazolyl, for example 1-tetrazolyl, or 1-cyclohexenyl or also 1,4-cyclohexadienyl, X represents oxygen or sulphur, m represents 0 or 1 and $R_b$ and $R_c$ each represent hydrogen or, if m represents 0, $R_c$ represents hydrogen and $R_b$ represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino or diphenylmethoxycarbonylamino, dihydroxytriazinylcarbonylamino or 3-guanylureido, as well as sulphoamino or tritylamino and also arylthioamino, for example 2-nitrophenylthioamino, arylsulphonylamino, for example 4-methylphenylsulphonylamino, or 1-lower alkoxycarbonyl-2-propylideneamino, for example 1-ethoxycarbonyl-2-propylideneamino, carboxyl or carboxyl present in the form of a salt, for example an alkali metal salt, such as a sodium salt, as well as protected carboxyl, for example etherified carboxyl, such as phenyl-lower alkoxycarbonyl, for example diphenylmethoxycarbonyl, sulpho or sulpho present in the form of a salt, for example an alkali metal salt, such as a sodium salt, as well as protected sulpho, hydroxyl, as well as protected hydroxyl, such as acyloxy, for example α-poly-branched lower alkoxycarbonyloxy, such as tert.-butoxycarbonyloxy, or 2-halogen-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O'-di-lower alkylphosphono, for example O-methylphosphono or O,O'-dimethylphosphono, or denotes a 5-amino-5-carboxy-valeryl radical, wherein the amino and/or carboxyl groups can also be protected and respectively are present, for example, as acylamino, for example lower alkanoylamino, such as acetylamino, halogeno-lower alkanoylamino, such as dichloroacetylamino, benzoylamino or phthaloylamino, and as esterified carboxyl, such as phenyl-lower alkoxycarbonyl, for example diphenylmethoxycarbonyl, and m preferably denotes 1 if $R_a$ represents phenyl, hydroxyphenyl, hydroxychlorophenyl or pyridyl, and m denotes O and $R_b$ differs from hydrogen if $R_a$ represents phenyl, hydroxyphenyl, hydroxychlorophenyl, thienyl, furyl, isothiazolyl, 1,4-cyclohexadienyl or 1-cyclohexenyl, or wherein m is O, $R_a$ denotes phenyl, 2-thienyl or 2-furyl and $R_b$ and $R_c$ conjointly denote lower alkoxyimino, cycloalkoxyimino or phneylalkoxyimino in the syn-configuration, $R_1^b$ denotes hydrogen, $R_2$ above all represents hydroxyl and also represents lower alkoxy, especially α-poly-branched lower alkoxy, for example tert.-butoxy, 2-halogen-lower alkoxy, for example 2,2,2-trichloroethoxy, 2-iodoethoxy or 2-bromoethoxy, or diphenylmethoxy which is optionally substituted, for example by lower alkoxy, for example methoxy, for example diphenylmethoxy or 4,4'-dimethoxy-diphenylmethoxy, as well as tri-lower alkylsilyloxy, for example trimethylsilyloxy, and $R_3$ denotes lower alkyl, for example methyl, ethyl or n-butyl, 2-amino-lower alkyl, such as 2-aminoethyl, carbo-lower alkoxy-lower alkyl, such as carbomethoxymethyl, as well as lower alkenyl, for example allyl, phenyl or phenyl-lower alkyl, for example benzyl, diphenyl or trityl, and also an aromatic heterocyclic radical which has 1 to 4 nitrogen atoms and/or an oxygen or sulphur atom and which is optionally substituted by lower alkyl, lower alkoxy or halogen, such as 1-methyl-5-tetrazolyl, as well as the 1-oxides of such 3-cephem compounds of the formula IA, and also the corresponding 2-cephem compounds of the formula IB, or salts, especially pharmaceutically usable, non-toxic salts, of such compounds having salt-forming groups, such as alkali metal salts, for example sodium salts, or alkaline earth metal salts, for example calcium salts, or ammonium salts, including those with amines, of compounds wherein $R_2$ represents hydroxyl, or inner salts of compounds wherein $R_2$ represents hydroxyl, and which contain a free amino group in the acyl radical of the formula B.

Above all, in 3-cephem compounds of the formula IA, and also in corresponding 2-cephem compounds of the formula IB, as well as in salt, especially in pharmaceutically usable, non-toxic salts of such compounds having salt-forming groups, as in the salts mentioned in the preceding paragraph, $R_1^a$ represents hydrogen, cyanoacetyl or the acyl radical of the formula B, wherein $R_a$ denotes phenyl, as well as hydroxyphenyl, for example 4-hydroxyphenyl, thienyl, for example 2- or 3-thienyl, 5-amino-methyl-2-thienyl, 2-furyl, 1-tetrazolyl, 4-isothiazolyl, 1,4-cyclohexadienyl or 1-cyclohexenyl, X denotes oxygen, m denotes 0 or 1 and $R_b$ and $R_c$ each denote hydrogen or, if m represents O, $R_b$ denotes amino, as well as protected amino, such as acylamino, for example 60-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzylcarbonylamino, dihydroxytriazinylcarbonylamino or hydroxyl, as well as protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxy-valeryl radical, wherein the amino and carboxyl groups can also be protected and respectively are present, for example, as acylamino, for example lower alkanoylamino, such as acetylamino, halogeno-lower alkanoylamino, such as dichloroacetylamino, benzoylamino, or phthaloylamino, and as esterified carboxyl, such as phenyl-lower alkoxycarbonyl, for example diphenylmethoxycarbonyl, with m preferably denoting 1, if $R_a$ is phenyl or hydroxyphenyl, or wherein m is O, $R_a$ denotes phenyl, 2-thienyl or 2-furyl and $R_b$ and $R_c$ conjointly denote lower alkoxyimino, cycloalkoxyimino or phenylalkoxyimino in the syn-configuration, $R_1^b$ represents hydrogen, $R_2$ above all denotes hydroxyl and also lower alkoxy, which is optionally halogen-substituted, for example chlorine-substituted, bromine-substituted or iodine-substituted, in the 2-position, especially α-poly-branched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy, as well as tri-lower alkylsilyloxy, for example trimethyldisylyloxy, and $R_3$ denotes lower alkyl, for example methyl, ethyl or n-butyl, 2-amino-lower alkyl, such as 2-aminoethyl, carbo-lower alkoxy-lower alkyl, such as carbomethoxymethyl, as well as lower alkenyl, for example allyl, phenyl or phenyl-lower alkyl, for example benzyl, diphenylmethyl or trityl, or an aromatic heterocyclic radical which has 1 to 4 nitrogen atoms and/or an oxygen or sulphur atom and which is optionally substituted by lower alkyl, lower alkoxy or halogen, such as 1-methyl-5-tetrazolyl.

The invention relates above all to 7β-(D-α-amino-α-$R_a$-acetylamino)-3-$R_3$-thio-3-cephem-4-carboxylic acids, wherein $R_a$ represents phenyl, 4-hydroxyphenyl, 2-thienyl, 1,4-cyclohexadienyl or 1-cyclohexenyl and wherein amino is optionally substituted by triazinylcarbonyl which contains two hydroxyl groups, especially 3,5-dioxo-2,3,4,5-tetrahydro-1,2,4-triazin-6-yl-carbonyl, and in particular to 7β-(α-$R_a$-acetylamino)-3-$R_3$-thio-3-cephem-4-carboxylic acid, wherein $R_a$ denotes cyano, phenyl, phenyloxy, 4-hydroxyphenyl, 2-thienyl, 5-aminomethyl-2-thienyl, 2-furyl, 1-tetrazolyl, 1,4-cyclohexadienyl or 1-cyclohexenyl, as well as to 7β-(α-$R_a$-α-hydroxyacetylamino)- and 7β-(α-$R_a$-α-syn-lower alkoxyimino-acetylamino)-3-$R_3$-thio-3-cephem-4-carboxylic acids, wherein $R_a$ denotes phenyl, 2-thienyl or 2-furyl and lower alkoxy, especially methoxy, and $R_3$ represents methyl, 2-aminoethyl, carbomethoxymethyl, allyl, phenyl, trityl or 1-methyl-5-tetrazolyl, and above all to 3-methylthio-, 3-(2-aminoethylthio)-, 3-carbomethoxymethylthio-, 3-allylthio-, 3-(1-methyl-5-tetrazolylthio)- and 3-phenylthio-7β-(D-α-phenyl-glycylamino-3-cephem-4-carboxylic acid and in particular to 3-carbomethoxymethylthio-7β-phenylacetylamino-3-cephem-4-carboxylic acid, 3-methylthio-7β-D-mandeloylamino)-3-cephem-4-carboxylic acid, 3-methylthio-7β-phenoxyacetylamino-3-cephem-4-carboxylic acid and 3-(1-methyl-5-tetrazolylthio)-7β-[2-(1-tetrazolyl)-acetylamino]-3-cephem-4-carboxylic acid and the pharmaceutically acceptable salts thereof. In the abovementioned concentrations, these compounds are of low toxicity and exhibit excellent antibiotic properties both against Gram-positive and especially Gram-negative bacteria on parenteral administration and, in the case of 7β-(D-α-amino-α-$R_a$-acetylamino)-3-$R_3$-thio-3-cephem-4-carboxylic acids especially on oral administration.

The processes for the manufacture of compounds of the formulae IA and IB and of their S-oxides and salts are characterised in that (a) a compound of the formula

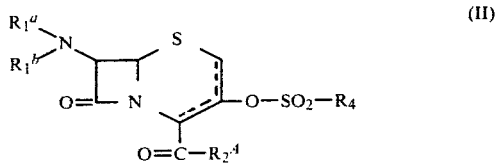

wherein $R_4$ represents an optionally substituted hydrocarbon radical and $R_1{}^a$, $R_1{}^b$ and $R_2{}^A$ have the meaning mentioned under the formula IA or IB and wherein the double bond is in the 2,3-position or 3,4-position, or a 1-oxide of such a compound is treated in the presence of a base with a thiol of the formula HS—$R_3$ (III), or (b) the compound HO—$R_5$ is split off, in the presence of an acid, from a compound of the formula

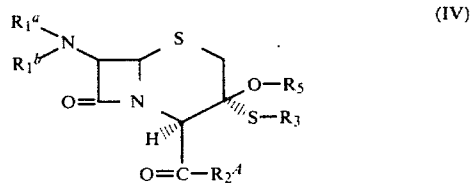

wherein the broken lines designate the α-configuration, or from a S-oxide thereof, wherein $R_5$ represents an optionally substituted hydrocarbon radical and $R_1{}^a$, $R_1{}^b$, $R_2{}^A$ and $R_3$ have the meaning indicated under the formula IA or IB, or (c) in a compound of the formula

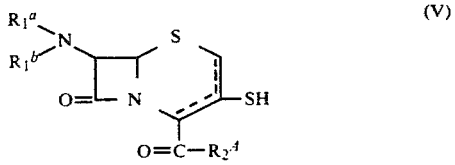

wherein $R_1{}^a$, $R_1{}^b$ and $R_2{}^A$ have the meaning indicated under the formula IA or IB and wherein the double bond is in the 2,3-position or 3,4-position, or in a corresponding 1-oxide of such a compound, the mercapto group is converted by etherification into a —S—$R_3$ group and, if desired, in a resulting compound of the formula IA or IB or in a 1-oxide thereof, the protected carboxyl group of the formula —C(=O)—$R_2{}^A$ is converted into the free carboxyl group or into another protected carboxyl group and/or if desired, within the definition of the end products, a resulting compound is coverted into another compound and/or, if desired, a resulting compound having a salt-forming group is converted into a salt or a resulting salt is converted into the free compound or into another salt and/or, if desired, a resulting mixture of isomeric compounds is separated into the individual isomers.

In a starting material of the formula II, $R_4$ is an optionally substituted aliphatic, cycloaliphatic, araliphatic or aromatic hydrocarbon radical with up to 18, preferably up to 10, carbon atoms. Suitable groups $R_4$ are, for example, an alkyl group, especially a lower alkyl group, such as a methyl, ethyl or butyl group, an alkenyl group, such as an allyl or butenyl group, which are optionally substituted, such as monosubstituted or polysubstituted by lower alkoxy, such as methoxy, halogen, such as fluorine, chlorine or bromine, aryl, such as phenyl, or aryloxy, such as phenyloxy, or a cycloalkyl group, such as a cyclopentyl or cyclohexyl group, or a naphthyl or especially a phenyl group which is optionally monosubstituted or polysubstituted by lower alkyl, such as methyl, lower alkoxy, such as methoxy, halogen, such as fluorine, chlorine or bromine, aryl, such as phenyl, aryloxy, such as phenyloxy, or nitro, for example phenyl, o-, m- or preferably p-tolyl, o-, m- or preferably p-methoxyphenyl, o-, m- or p-chlorophenyl, p-biphenylyl, p-phenoxyphenyl, p-nitrophenyl or 1- or 2-naphthyl.

In a starting material of the formula III, $R_3$ has the same meaning as in end products of the formula IA or IB and functional groups, such as amino, hydroxyl, carboxyl and the like, are preferably in the protected form.

In a starting material of the formula IV, $R_3$ is preferably an optionally substituted hydrocarbon radical or an optionally substituted heterocyclic radical and the carbon atom bonded to the thio group is saturated, that is to say does not form a double bond.

In a starting material of the formula IV, $R_5$ represents an optionally substituted hydrocarbon radical and can thus have the same meaning as the optionally substituted hydrocarbon radical $R_3$ in the end product of the formula IA or IB. Preferred hydrocarbon radicals $R_5$ are lower alkyl radicals, especially the methyl radical. The substituent —O—$R_5$, which is to be split off, has the β-configuration. Depending on the preparation, the group —C(=O)—$R_2{}^A$ has the β- or the α-configuration. Either the pure positional isomers or the epimer mixtures of 3β-(O—$R_5$)-3α-(S—$R_3$)-cephem-4β-carboxylic acid derivatives and the corresponding 3β-(O—$R_5$)-3α-(S—$R_3$)-cepham-4α-carboxylic acid derivatives can be employed in the reaction but only the former are able to split off HO—$R_5$.

In a starting material of the formula II, IV or V, $R_2{}^A$ preferably represents an etherified hydroxyl group $R_2{}^A$ which, with the —C(=O)—grouping, forms an etherified hydroxyl group which can be split, especially under mild conditions, it being possible for functional groups which may be present in a carboxyl protective group $R_2{}^A$ to be protected in a manner which is in itself known, for example as indicated above. A group $R_2{}^A$ is, for example, in particular an optionally halogen-substituted lower alkoxy group, such as α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromethoxy or 2-iodoethoxy, or an optionally substituted 1-phenyl-lower alkoxy group, such as a 1- phenyl-lower alkoxy group which contains lower alkoxy, for example methoxy, or nitro, such as benzyloxy or diphenylmethoxy which are optionally substituted, for example as indicated, for example benzyloxy, 4-methoxybenzyloxy, 4-nitrobenzyloxy, diphenylmethoxy or 4,4′-dimethoxy-diphenylmethoxy, and also an organic silyloxy or stannyloxy group, such as tri-lower alkylsilyloxy, for example trimethylsilyloxy. Preferably, in a starting material of the formula II, IV or V, the radical $R_1{}^a$ denotes an amino protective group $R_1{}^A$, such as an acyl group Ac, wherein free functional groups which may be present, for example amino, hydroxyl, carboxyl or phosphono groups, can be protected in a manner which is in itself known, amino groups, for example, by the abovementioned acyl, trityl, silyl or stannyl radicals as well as substituted thio or sulphonyl radicals, and hydroxyl, carboxyl or phosphono groups, for example, by the abovementioned ether or ester groups, including silyl or stannyl groups, and $R_1{}^b$ denotes hydrogen.

Particularly preferred starting materials of the formula IV are those which have no basic group, especially no amino group, or no protected basic group which can be converted into a free basic group during the elimination reaction with acids.

In starting materials of the formulae II and V, the ring double bond can be in the 2,3-position or 3,4-position. It is also possible to use a mixture of a compound of the formula II and the corresponding 1-oxide, or a mixture of a compound of the formula IV and the corresponding 1-oxide, or a mixture of the formula V and the corresponding 1-oxide as the starting material and to obtain as the product a mixture of compounds of the formulae IA and IB and the 1-oxide of a compound of the formula IA. A starting material can be employed in the pure form or in the form of the crude reaction mixture obtainable from its preparation. The starting material of the formula V can also be employed in the form of its thioketone and enolised only during the etherification reaction.

The substitution of the group $-O-SO_2-R_4$ by the group $-S-R_3$, which is effected according to process (a), takes place in a manner which is in itself known with cooling, at room temperature or with warming, that is to say at temperatures between about $-70°$ C. and about $+100°$ C., preferably at about $0°$ C. to about $40°$ C., in a suitable inert solvent and in a base. Suitable inert solvents are, for example, aliphatic, cycloaliphatic or aromatic hydrocarbons, which are optionally substituted, for example halogenated, such as fluorinated or chlorinated, such as hexane, cyclohexane, benzene, toluene, xylene, methylene chloride, chloroform or carbon tetrachloride, ether-like solvents, such as di-lower alkyl ethers, for example diethyl ether, diisopropyl ether, 1,2-dimethoxyethane, tetrahydrofurane or dioxane, N,N-di-lower alkylamides, such as N,N-dimethylformamide or N,N-dimethylacetamide, lower alkylnitriles, such as acetonitrile, di-lower alkyl sulphides, such as dimethyl sulphide, di-lower alkylsulphoxides, such as dimethylsulphoxide, or mixtures thereof. Suitable bases are, in particular, sterically hindered amines, such as trilower alkylamines, for example N,N-diisopropyl-N-ethylamine, and also alkali metal hydrides, amides or alcoholates, such as sodium hydride, sodium amide or lithium amide, sodium ethylate or potassium tert.-butylate. The reaction can be carried out in an inert gas atmosphere, such as a nitrogen atmosphere, and, if necessary, in a closed vessel under pressure.

The elimination of the alcohol HO—$R_5$, which is effected according to process (b), takes place in the presence of an acid, in the presence or absence of a suitable inert solvent and with cooling, at room temperature or with warming, that is to say at temperatures between about $-70°$ C. and $+100°$ C., preferably at about $5°$ C. to about $40°$ C. Acids which are suitable for splitting off HO—$R_5$ are strong organic or inorganic protic acids, especially mineral acids, such as hydrochloric acid, sulphuric acid, nitric acid or phosphoric acid, and also sulphonic acids, such as lower alkanesulphonic acids, for example methanesulphonic acid, or aromatic sulphonic acids, for example benzenesulphonic acid or toluenesulphonic acid, halogenated lower alkanecarboxylic acids, such as trifluoroacetic acid or trichloroacetic acid, or formic acid. Suitable solvents are, for example, aliphatic, cycloaliphatic or aromatic hydrocarbons which are optionally substituted, such as halogenated, for example fluorinated or chlorinated, such as hexane, cyclohexane, benzene, toluene, xylene, methylene chloride, chloroform or carbon tetrachloride, ether-like solvents, such as di-lower alkyl ethers, for example diethyl ether, diisopropyl ether, 1,2-dimethoxyethane, tetrahydrofurane or dioxane, di-lower alkylamides, such as N,N-dimethylformamide or N,N-dimethylacetamide, lower alkylnitriles, such acetonitrile, di-lower alkyl sulphides, such as dimethyl sulphide, and di-lower alkylsulphoxides, such as dimethylsulphoxide, or mixtures thereof.

Compounds of the formula IA and/or IB are obtained according to process (c) by any method suitable for the etherification of thioenol groups, it being possible to use starting materials of the formula V, wherein $R_1{}^a$ and $R_1{}^b$ represent hydrogen but wherein $R_1{}^a$ preferably represents an amino protective group $R_1{}^A$. For example, a diazo compound, which corresponds to the radical $R_3$, of the formula $R_3-N_2$, above all an optionally substituted diazo-lower alkane, for example diazomethane, diazoethane or diazo-n-butane, as well as an optionally substituted phenyl-diazo-lower alkane, such as a 1-phenyl-diazo-lower alkane, for example phenyldiazomethane or diphenyldiazomethane, is used as the etherification reagent. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, a lower alkanol, for example methanol, ethanol or tert.-butanol, or an ether, such as a di-lower alkyl ether, for example diethyl ether, or a cyclic ether, for example tetrahydrofurane or dioxane, or a solvent mixture and, depending on the diazo reagent, with cooling, at room temperature or with slight warming and, if necessary, in a closed vessel and/or under an inert gas atmosphere, for example a nitrogen atmosphere.

Furthermore, compounds of the formula IA and/or IB can be formed according to process (c) by treatment with a reactive ester of an alcohol, corresponding to the radical $R_3$, of the formula $R_3$—OH. Suitable esters are, above all, those with strong inorganic or organic acids, such as mineral acids, for example hydrogen halide acids, such as hydrochloric acid, hydrobromic acid or hydriodic acid, as well as sulphuric acid or halogenosulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzenesulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially di-lower alkyl sulphates, such as dimethyl sulphate, as well as lower alkyl fluorosulphates, for example methyl fluorosulphate, or optionally halogen-substituted methanesulphonic acid lower alkyl esters, for example trifluoromethanesulphonic acid methyl ester, are customarily used in the presence of a solvent, such as an optionally halogenated, such as chlorinated, aliphatic, cycloaliphatic or aromatic hydrocarbon, for example methylene chloride, an ether, such as dioxane or tetrahydrofurane, or a lower alkanol, such as methanol, or a mixture thereof. With this process, suitable condenation agents, such as alkali metal carbonates or bicarbonates, for example sodium carbonate or bicarbonate or potassium carbonate or bicarbonate (usually together with a sulphate), or organic bases, such as tri-lower alkylamines, which are usually sterically hindered, for example N,N-diisopropyl-N-ethylamine (preferably together with lower alkyl halogenosulphates or optionally halogen-substituted methanesulphonic acid lower alkyl esters) are preferably used and the reaction is carried out with cooling, at room temperature or with warming, for example at temperatures from about $-20°$ C. to about $50°$ C., and, if necessary, in a closed vessel and/or in an inert gas atmosphere, for example a nitrogen atmosphere.

The etherification with a reactive ester of an alcohol $R_3$—OH, corresponding to the radical $R_3$, can also be carried out without adding further condensation agents, using the heavy metal sulphide of a starting material of the formula V, which may be obtained, for example, during the preparation of the starting material of the formula V, that is to say a compound of the formula V wherein the hydrogen atom of the —SH group is replaced by a heavy metal.

The etherification can also be carried out by treatment with a compound which contains, on the same carbon atom of aliphatic character, two or three etherified hydroxyl groups of the formula $R_3$—O—, that is to say with a corresponding acetal or ortho-ester, in the presence of an acid agent. Thus, for example, it is possible to use gem-lower alkoxy-lower alkanes, such as 2,2-dimethoxy-propane, as the etherification agent, in the presence of a strong organic sulphonic acid, such as p-toluenesulphonic acid, and a suitable solvent, such as a lower alkanol, for example methanol, or a di-lower alkylsulphoxide or lower alkylene-sulphoxide, for example dimethylsulphoxide, or an ortho-formic acid tri-lower alkyl ester, for example ortho-formic acid triethyl ester, in the presence of a strong mineral acid, for example sulphuric acid, or of a strong organic sulphonic acid, such as p-toluenesulphonic acid and a suitable solvent, such as a lower alkanol, for example ethanol, or an ether, for example dioxane, and thus to obtain thioenol compounds of the formula IA and/or IB, wherein $R_3$ represents lower alkyl, for example methyl or ethyl.

The thioenol ethers of the formula IA and/or IB can also be obtained when starting materials of the formula V are treated with tri-$R_3$-oxonium salts of the formula $(R_3)_3O^{\oplus}A^{\ominus}$ (so-called Meerwein salts), as well as di-$R_3O$-carbenium salts of the formula $(R_3O)_2CH^{\oplus}A^{\ominus}$ or di-$R_3$-halonium salts of the formula $(R_3)_2hal^{\oplus}A^{\ominus}$, wherein $A^{\ominus}$ denotes the anion of an acid and $hal^{\oplus}$ denotes a halonium ion, especially a bromonium ion.

The salts are, above all, tri-lower alkyloxonium salts, as well as di-lower alkoxycarbenium salts or di-lower alkylhalonium salts, especially the corresponding salts with complex, fluorine-containing acids, such as the corresponding tetrafluoborates, hexafluorophosphates, hexafluoroantimonates or hexachloroantimonates. Examples of such reagents are trimethyloxonium hexafluoroantimonate, hexachloroantimonate, hexafluorophosphate or tetrafluoborate or triethyloxonium hexafluoroantimonate, hexachloroantimonate, hexafluorophosphate or tetrafluoborate, dimethoxycarbenium hexafluorophosphate or dimethylbromonium hexafluoroantimonate. These etherification agents are preferably used in an inert solvent, such as an ether or a halogenated hydrocarbon, for example diethyl ether, tetrahydrofurane or methylene chloride, or in a mixture thereof, if necessary in the presence of a base, such as an organic base, for example a tri-lower alkylamine, which is preferably sterically hindered, for example N,N-diisopropyl-N-ethylamine, and with cooling, at room temperature or with slight warming, for example at about $-20°$ C. to about $50°$ C., if necessary in a closed vessel and/or in an inert gas atmosphere, for example a nitrogen atmosphere.

The thioenol ethers of the formulae IA and/or IB can also be prepared by treating starting materials of the formula V with a 3-substituted 1-$R_3$-triazene compound (that is to say a compound of the formula substituent—N=N—NH—$R_3$), the substituent on the nitrogen atom in the 3-position denoting an organic radical which is bonded via a carbon atom, preferably a carbocyclic aryl radical, such as an optionally substituted phenyl radical, for example lower alkylphenyl, such as 4-methylphenyl. Triazene compounds of this type are 3-aryl-1-lower alkyl-triazenes, for example 3-(4-methylphenyl)-1-methyl-triazene, 3-(4-methyl-phenyl)-1-ethyl-triazene, 3-(4-methylphenyl)-1-n-propyl-triazene or 3-(4-methylphenyl)-1-isopropyl-triazene, 3-aryl-1-lower alkenyl-triazenes, for example 3-(4-methylphenyl)-allyl-triazine, or 3-aryl-1-phenyl-lower alkyl-triazenes, for example 3-(4-methylphenyl)-1-benzyl-triazene. These reagents are customarily used in the presence of inert solvents, such as optionally halogenated hydrocarbons or ethers, for example benzene, or solvent mixtures, and with cooling, at room temperature and preferably at elevated temperature, for example at about $20°$ C. to about $100°$ C., if necessary in a closed vessel and/or in an inert gas atmosphere, for example a nitrogen atmosphere.

In the reactions according to the invention it is possible, depending on the starting material and the reaction conditions, to obtain single compounds of the formula IA or IB or mixtures thereof. Thus, for example, the latter arise when, for example, mixed starting materials of the formula II or formula V are used or when the reaction is carried out under basic conditions. Resulting mixtures can be separated in a manner which is in itself known, for example with the aid of suitable methods of separation, for example by adsorption and fractional elution, including chromatography (column, paper or plate chromatography) using suitable adsorbents, such as silica gel or aluminium oxide, and eluting agents, and also by fractional crystallisation, solvent partition and the like.

In the process according to the invention, and in additional measures which may need to be carried out, it is possible, if necessary, temporarily to protect, in a manner which is in itself known, free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation, and in each case to liberate them after the reaction has taken place, if desired, individually or conjointly, in a manner which is in itself known. Thus it is preferably possible, for example, to protect amino, hydroxyl, carboxyl or phosphono groups in an acyl radical $R_1^A$ or $R_1^b$, for example in the form of acylamino groups, such as those mentioned above, for example, 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, in the form of arylthioamino or aryl-lower alkylthioamino groups, for example 2-nitrophenylthioamino groups, or arylsulphonylamino groups, for example 4-methylphenylsulphonylamino groups, or in the form of 1-lower alkoxycarbonyl-2-propylideneamino groups, or, respectively, of acyloxy groups, such as those mentioned above, for example tert.-butoxycarbonyloxy, 2,2,2-trichloroethoxycarbonyloxy or 2-bromoethoxycarbonyloxy groups, or in the form of esterified carboxyl groups, such as those mentioned above, for example diphenylmethoxycarbonyl groups, or, respectively, O,O'-disubstituted phosphono groups, such as those mentioned above, for example O,O'-di-lower alkylphosphono groups, for example O,O'-dimethylphosphono groups, and subsequently, if appropriate after conversion of the protective group, for example of a 2-bromoethoxycarbonyl group into a 2-iodoethoxycarbonyl group, to split the protected group in a manner which is in itself known and depending on the nature of the protective group, for example to split a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifuoroacetic acid, an arylthioamino or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with aqueous mineral acid, or a tert.-butoxycarbonyl group by treatment with formic acid or trifluoroacetic acid, or a 2,2,2-trichloroethoxycarbonyloxy group by treatment with a chemical reducing agent, such as zinc in the presence of aqueous acetic acid, or a diphenylmethoxycarbonyl group by treatment with formic acid or trifluoroacetic acid or by hydrogenolysis, or a O,O'-disubstituted phosphono group by treatment with an alkali metal halide, the splitting being carried out, for example, partially.

In a compound of the formula IA or IB obtainable according to the invention and possessing a protected, especially esterified, carboxyl group of the formula $-C(=O)-R_2^A$, the latter can be converted into the free carboxyl group in a manner which is in itself known, for example depending on the nature of the group $R_2^A$. An esterified carboxyl group, for example a carboxyl group esterified by a lower alkyl radical, especially methyl or ethyl, especially in a 2-cephem compound of the formula IB, can be converted into a free carboxyl group by hydrolysis in a weakly basic medium, for example by treatment with an aqueous solution of an alkali metal hydroxide or carbonate or an alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or by an arylcarbonylmethyl group can be split, for example by treatment with a chemical reducing agent, such as a metal, for example zinc, or a reducing metal salt, such as a chromium-II salt, for example chromium-II chloride, usually in the presence of a hydrogen donor which, together with the metal, is capable of producing nascent hydrogen, such as an acid, above all acetic acid and also formic acid, or of an alcohol, water preferably being added, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl grouping can be split, for example, by irradiation, preferably with ultraviolet light, for example below 290 mµ, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 mµ, if the arylmethyl group denotes, for example, a benzyl radical which is substituted in the 2-position by a nitro group, a carboxyl group which is esterified by a suitable substituted methyl group, such as tert.-butyl or diphenylmethyl, can be split, for example, by treatment with a suitable acid agent, such as formic acid or trifluoroacetic acid, optionally with the addition of a nucleophilic compound, such as phenol or anisole, an activated esterified carboxyl group, and also a carboxyl group present in the form of an anhydride, can be split by hydrolysis, for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula IA or IB can be converted in a manner which is in itself known into other compounds of the formula IA or IB.

In a resulting compound it is possible, for example, to split off an amino protective group $R_1^A$ or $R_1^b$, especially an easily removable acyl group, in a manner which is in itself known, for example an α-polybranched lower alkoxycarbonyl group, such as tert.-butoxycarbonyl, can be split off by treatment with trifluoroacetic acid and a 2-halogeno-lower alkoxycarbonyl group, such as 2,2,2-trichloroethoxycarbonyl or 2-iodoethoxycarbonyl, or a phenacyloxycarbonyl group, can be split off by treatment with a suitable reducing metal or corresponding metal compound, for example zinc or a chromium-II compound, such as chromium-II chloride or chromium-II acetate, advantageously in the presence of an agent which, together with the metal or the metal compound, generates nascent hydrogen, preferably in the presence of aqueous acetic acid.

It is furthermore possible, in a resulting compound of the formula IA or IB, wherein a carboxyl group of the formula —C(=O)—R$_2$ preferably represents a carboxyl group which is protected, for example by esterification, including silylation, for example by reaction with a suitable organic halogenosilicon compound or halogentin-IV compound, such as trimethylchlorosilane or tri-n-butyl-tin chloride, to split off an acyl group R$_1^a$ or R$_1^b$, wherein free functional groups which may be present are optionally protected, by treatment with an imide-halide-forming agent, reaction of the resulting imide-halide with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carbxoylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monomamine or diamine, such as a tri-lower alkylamine, for example trimethylamine, triethylamine or N,N-diisopropyl-N-ethylamine, also a N,N,N',N'-tetra-lower alkyl-lower alkylenediamine, for example N,N,N',N'-tetramethyl-1,5-pentylene-diamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methylpiperidine or N-methylmorpholine, as well as 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic, monocyclic or bicyclic base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can, however, also be present in more than or less than an equimolar amount, for example in an about 0.2-fold to about 1-fold amount or in an up to about 10-fold, in particular about 3-fold to 5-fold, excess.

The reaction with the imide-halide-forming agent is preferably carried out with cooling, for example at temperatures of about −50° C. to about +10° C., but it is also possible to work at higher temperatures, that is to say, for example, up to about 75° C., if the stability of the starting materials and of the products permits a higher temperature.

The imide-halide product, which is usually further processed without isolation, is reacted, according to the process, with an alcohol, preferably in the presence of one of the abovementioned bases, to give the imino-ether. Examples of suitable alcohols are, for example, aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, as well as optionally substituted phenyl-lower alkanols, such as benzyl alcohol. Usually an excess, for example an up to about 100-fold excess, of the alcohol is used and the reaction is preferably carried out with cooling, for example at temperatures of about −50° C. to about 10° C.

The imino-ether product can advantageously be split without isolation. The splitting of the imino-ether can be achieved by treatment with a suitable hydroxy compound, preferably by means of hydrolysis, and also be alcoholysis, the latter being able to take place directly following the formation of the imino-ether if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5, which can, if necessary, be obtained by adding a basic agent, such as an aqueous alkali metal hydroxide, for example sodium hydroxide or potassium hydroxide, or an acid, for example a mineral acid or an organic acid, such as hydrochloric acid, sulphuric acid, phosphoric acid, fluoboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product, which can be obtained by the above process, instead of being reacted with an alcohol, is reacted with a salt, such as an alkali metal salt, of a carboxylic acid, especially of a sterically hindered carboxylic acid, a compound of the formula IA or IB, wherein both radicals R$_1^a$ and R$_1^b$ represent acyl groups, is obtained.

In a compound of the formula IA or IB, wherein both radicals R$_1^a$ and R$_1^b$ represent acyl groups, one of these groups, preferably the sterically less hindered group, can be removed selectively, for example by hydrolysis or aminolysis.

In a compound of the formula IA or IB, wherein R$_1^A$ and R$_1^b$, conjointly with the nitrogen atom, represent a phthalimido group, the latter can be converted into the free amino group, for example by hydrazinolysis, that is to say on treatment of such a compound with hydrazine.

Certain acyl radicals R$_1^A$ of an acylamino grouping in compounds obtainable according to the invention, such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl or phthaloyl, can also be split off by treatment with a nitrosylating agent, such as nitrosyl chloride, with a carbocyclic arenediazonium salt, such as benzenediazonium chloride, or with an agent which releases positive halogen, such as a N-halogeno-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol, or, if the 5-amino-5-carboxyvaleryl radical $R_1^A$ the amino group is unsubstituted and the carboxyl group is protected, for example by esterification, and $R_1^b$ preferably represents an acyl radical, but can also denote hydrogen, by leaving the substance to stand in an inert solvent, such as dioxane or a halogenated aliphatic hydrocarbon, for example methylene chloride, and, if necessary, working up the free or monoacylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group $R_1^A$, such as the trityl group, can be split off, for example by treatment with an acid agent, such as a mineral acid, for example hydrochloric acid.

In a compound of the formula IA or IB, wherein $R_1^a$ and $R_1^b$ represent hydrogen, the free amino group can be substituted by methods which are in themselves known, above all acylated by treatment with acids, such as carboxylic acids, or reactive derivatives thereof.

If a free acid, wherein optionally present functional groups, such as an optionally present amino group, are preferably protected, is employed for the acylation, suitable condensation agents are customarily used, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium-3'-sulphonate and N-tert.-butyl-5-methylisoxazolinium perchlorate, or a suitable acylamino compound, for example 2-ethoxy-1-ethoxycarbonyl-1,2-dihydroquinoline.

The condensation reaction is preferably carried out in one of the anhydrous reaction media mentioned further below, for example in methylene chloride, dimethylformamide or acetonitrile.

An amide-forming functional derivative of an acid, wherein optionally present groups, such as an optionally present amino group, are preferably protected, is above all an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with an acid containing phosphorus, for example phosphoric acid or phosphorous acid, with an acid containing sulphur, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl half-ester or isobutyl half-ester of carbonic acid, or with organic, especially aliphatic or aromatic, sulphonic acids, for example p-toluenesulphonic acid.

It is also possible to use, as acylating agents, inner anhydrides, such as ketenes, for example diketene, isocyanates (that is to say inner anhydrides of carbamic acid compounds) or inner anhydrides of carboxylic acid compounds having carboxyl-substituted hydroxyl or amino groups, such as mandelic acid O-carboxanhydride or the anhydride of 1-N-carboxyaminocyclohexanecarboxylic acid.

Further acid derivatives suitable for reaction with the free amino group are activated esters wherein optionally present functional groups are usually protected, such as esters with vinylogous alcohols (that is to say enols), such as vinylogous lower alkanols, or aryl esters, such as phenyl esters which are preferably substituted, for example by nitro or halogen, such as chlorine, for example pentachlorophenyl, 4-nitrophenyl or 2,4-dinitrophenyl esters, heteroaromatic esters, such as benztriazole esters or diacylamino esters, such as succinylimino or phthalylimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as a tri-lower alkylamine, for example triethylamine, a N,N-di-lower alkylaniline, for example N,N-dimethylaniline, or a base of the pyridine type, for example pyridine, or of an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or of an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions it is possible to start from compounds of the formulae IA or IB, wherein $R_2$ has the above meaning, and compounds having free carboxyl groups of the formula —C(=O)—$R_2$, wherein $R_2$ represents hydroxyl, can also be used in the form of salts, for example ammonium salts, such as with triethylamine, or in the form of a compound having a carboxyl group protected by reaction with a suitable organic phosphorus halide compound, such as with a lower alkylor lower alkoxy-phosphorus dihalide, such as methyl-phosphorus dichloride, ethyl-phosphorus dibromide or methoxy-phosphorus dichloride; in the resulting acylation product the protected carboxyl group can be liberated in a manner which is in itself known, for example as described above, including by hydrolysis or alcoholysis.

An acyl group can also be introduced by acylating a compound of the formula IA or IB, wherein $R_1{}^a$ and $R_1{}^b$ conjointly represent an ylidene radical (which can also be introduced subsequently, for example by treatment of a compound wherein $R_1{}^a$ and $R_1{}^b$ represent hydrogen, with an aldehyde, such as an aliphatic, aromatic or araliphatic aldehyde), for example according to the methods indicated above, and hydrolysing the acylation product, preferably in a neutral or weakly acid medium.

An acyl group can also be introduced stepwise. Thus, for example, it is possible to introduce into a compound of the formula IA or IB, having a free amino group, a halogenolower alkanoyl group, for example a bromoacetyl group, or, for example, by treatment with a carbonic acid dihalide, such as phosgene, a halogenocarbonyl group, for example a chlorocarbonyl group, and to react a N-(halogeno-lower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, and thus to obtain substituted N-lower alkanoylamino compounds or N-hydroxycarbonylamino compounds.

In both reactants, free functional groups can temporarily be protected during the acylation reaction, in a manner which is in itself known, and can be liberated, after the acylation, by means of methods which are in themselves known, for example as described above.

The acylation can also be effected by exchanging an already existing acyl group for another, preferably sterically hindered, acyl group, for example according to the process described above, by preparing the imide-halide compound, treating this with a salt of an acid and, in the product thus obtainable, splitting off hydrolytically one of the acyl groups present, usually the sterically less hindered acyl group.

It is furthermore possible, for example, to react a compound of the formula IA or IB, wherein $R_1{}^a$ represents a glycyl group which is preferably substituted in the α-position, such as phenylglycyl, and $R_1{}^b$ represents hydrogen, with an aldehyde, for example formaldehyde, or a ketone, such as a lower alkanone, for example acetone, and thus to obtain compounds of the formula IA or IB, wherein $R_1{}^a$ and $R_1{}^b$, conjointly with the nitrogen atom, represent a 5-oxo-1,3-diazacyclopentyl radical which is preferably substituted in the 4-position and optionally substituted in the 2-position.

In a compound of the formula IA or IB, wherein $R_1{}^a$ and $R_1{}^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkylsilane, lower alkoxy-lower alkyl-dihalogenosilane or tri-lower alkyl-silyl halide, for example dichloro-dimethylsilane, methoxy-methyl-dichlorosilane, trimethylsilyl chloride or dimethyl-tert.-butyl-silyl chloride, such silyl halide compounds preferably being used in the presence of a base, for example pyridine, or by treatment with an optionally N-mono-lower alkylated, N,N-di-lower alkylated, N-tri-lower alkylsilylated or N-lower alkyl-N-tri-lower alkylsilylated N-(tri-lower alkylsilyl)-amine (see, for example, British Pat. No. 1,073,530), or with a silylated carboxylic acid amide, such as a bis-tri-lower alkylsilyl-acetamide, or example bis-trimethylsilyl-acetamide, or trifulorosilylacetamide, or also by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, a tetra-lower alkoxy-tin compound or a tetra-lower alkyl-tin compound, or with a tri-lower alkyl-tin halide, for example tri-n-butyl-tin chloride (see, for example, Netherlands Published Specification 67/11,107).

In a compound of the formula IA or IB, obtainable according to the process, which contains a free carboxyl group of the formula $—C(=O)—R_2$, such a group can be converted into a protected carboxyl group in a manner which is in itself known. Thus esters are obtained, for example, by treatment with a suitable diazo compound, such as a diazo-lower alkane, for example diazomethane or diazobutane, or a phenyldiazo-lower alkane, for example diphenyldiazomethane, if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N'-disubstituted O- or S-substituted isourea or isothiourea, wherein a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or by any other known and suitable esterification process, such as reaction of a salt of the acid with a reactive ester of an alcohol and of a strong inorganic acid, or with a strong organic sulphonic acid. Furthermore, acid halides, such as acid chlorides (prepared, for example, by treatment with oxalyl chloride), activated esters (formed, for example, with N-hydroxy-nitrogen compounds, such as N-hydroxy-succinimide), or mixed anhydrides (obtained, for example, with halogeno-formic acid lower alkyl esters, such as chloroformic acid ethyl ester or chloroformic acid isobutyl ester, or with halogenoacetic acid halides, such as trichloroacetic acid chloride) can be converted into an esterified carboxyl group by reaction with alcohols, optionally in the presence of a base, such as pyridine.

In a resulting compound having an esterified grouping of the formula $—C(=O)—R_2$, this grouping can be converted into another esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be prepared by reacting a compound of the formula IA or IB having a free carboxyl group of the formula $—C(=O)—R_2$, preferably a salt, especially an alkali metal salt, for example a sodium salt or ammonium salt, for example the triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula —C(=O)—R$_2$, such a group can also be converted into an optionally substituted carbamoyl or hydrazinocarbonyl group, this being effected by reacting preferably reactive functionally modified derivatives, such as the abovementioned acid halides, and generally esters, including also the abovementioned activated esters, or mixed anhydrides, of the appropriate acid with ammonia or amines, including hydroxylamine, or hydrazines.

A carboxyl group protected by an organic silyl or stannyl group can be formed in a manner which is in itself known, for example by treating compounds of the formulae IA or IB, wherein R$_2$ represents hydroxyl, or salts, such as alkali metal salts, for example sodium salts, thereof, with a suitable silylating or stannylating agent, such as one of the abovementioned silylating or stannylating agents; see, for example, British Pat. No. 1,073,530 and Netherlands Published Specification No. 67/17,107.

It is furthermore possible to liberate modified functional substituents in groups R$_1^A$, R$_1^b$ and/or R$_2$, such as substituted amino groups, acylated hydroxyl groups, esterified carboxyl groups or O,O'-disubstituted phosphono groups, by methods which are in themselves known, for example those described above, or functionally to modify free functional substituents in groups R$_1^A$, R$_1^b$ and/or R$_2$, such as free amino, hydroxyl, carboxyl or phosphono groups, by processes which are in themselves known, for example by acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanylsemicarbazide with sodium nitrate can be reacted with a compound of the formula IA or IB, wherein, for example, the amino protective group R$_1^A$ represents an optionally substituted glycyl group, and the amino group can thus be converted into a 3-guanylureido group. Furthermore, compounds with aliphatically bonded halogen, for example with an optionally substituted α-bromoacetyl grouping, can be reacted with esters of phosphorous acid, such as tri-lower alkyl phosphite compounds, and the corresponding phosphono compounds can thus be obtained.

A mixture, obtainable according to the process, of a compound of the formula IA and a corresponding 1-oxide can be oxidised direct, either partially to the 1-oxide or, by using an excess of oxidising agent, to the di-S-oxide of a compound of the formula IA or can be reduced to a 3-cephem compound of the formula IA or IB. These oxidation and reduction steps are described below in connection with the isomerisation of a 2-cephem compound of the formula IB to the corresponding 3-cephem compound of the formula IA using a 1-oxide as the intermediate product.

Resulting cephem compounds of the formula IA and B can be converted into 1-oxides or di-S-oxides of the corresponding cephem compounds of the formula IA or B by oxidation with suitable oxidising agents, such as those described below. Resulting S-oxides of 3-cephem compounds of the formula IA can be reduced to the corresponding 3-cephem compounds of the formula IA by reduction with suitable reducing agents, such as, for example, those described below. In these reactions care must be taken to ensure that, if necessary, free functional groups are protected and, if desired, are subsequently liberated again.

Resulting cephem compounds can be isomerised. Thus, resulting 2-cephem compounds of the formula IB can be converted into the corresponding 3-cephem compounds of the formula IA by isomerising a 2-cephem compound of the formula IB, wherein free functional groups can, if appropriate, be protected temporarily, for example as indicated. In this reaction it is possible to use, for example, 2-cephem compounds of the formula IB, wherein the group of the formula —C(=O)—R$_2$ represents a free or protected carboxyl group, and it is also possible to form a protected carboxyl group during the reaction.

Thus, it is possible to isomerise a 2-cephem compound of the formula IB by treating it with a weakly basic agent and isolating the corresponding 3-cephem compound of the formula IA from an equilibrium mixture of the 2- and 3-cephem compounds which may be obtained.

Examples of suitable isomerising agents are organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-zacycloalkanes, for example N-methyl-piperidine, or N-phenyl-lower alkyl-N,N-di-lower alkylamines, for example N-benzyl-N,N-dimethylamine, as well as mixtures thereof, such as the mixture of a base of the pyridine type, for example pyridine, and a N,N,N-tri-lower alkylamine, for example pyridine and triethylamine. Furthermore, it is also possible to use inorganic or organic salts of bases, especially of medium strength to strong bases, with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can be carried out, for example, in the presence of a derivative of a carboxylic acid which is suitable for forming a mixed anhydride, such as a carboxylic acid anhydride or carboxylic acid halide, for example with pyridine in the presence of acetic anhydride. This reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases which are used as reactants and are liquid under the reaction conditions at the same time also to serve as solvents, if necessary with cooling or heating, preferably in a temperature range from about −30° C. to about +100° C., in an inert gas atmosphere, for example a nitrogen atmosphere, and/or in a closed vessel.

The 3-cephem compounds of the formula IA, thus obtainable, can be separated from 2-cephem compounds of the formula IB which may still be present, in a manner which is in itself known, for example by adsorption and/or crystallisation.

The isomerisation of 2-cephem compounds of the formula IB can also be carried out by oxidising these in the 1-position and optionally at the S-R$_3$ group, if desired, separating a mixture of the S-oxides of 2- and/or 3-cephem compounds of the formula IA and IB, which is obtainable, for isomerising this mixture to the corresponding S-oxides of 3-cephem compounds, and reducing the S-oxides of the corresponding 3-cephem compounds of the formula IA, which are thus obtainable.

Suitable oxidising agents which can be used for the oxidation of 2-cephem compounds in the 1-position and at the —S—$R_3$ group are inorganic per-acids which have a reduction potential of at least +1.5 volt and which consist of nonmetallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids, which can be added as such or can be formed in situ by the use of at least one equivalent of hydrogen peroxide and of a carboxylic acid. It is appropriate to use a large excess of the carboxylic acid when, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphonic acid.

The oxidation can also be carried out using hydrogen peroxide with catalytic abounts of an acid having a dissociation constant of at least $10^{-5}$, it being possible to employ low concentrations, for example 1–2% or less, but also larger amounts, of the acid. The activity of the mixture depends above all on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. About equimolar amounts of the oxidising agent are used to produce the 1-oxides. When an excess is used the di-S-oxides are formed to an increased extent. The oxidation is carried out under mild conditions, for example at temperatures from about −50° C. to about +100° C., preferably from about −10° C. to about +40° C.

The oxidation of cephem compounds to their S-oxides can also be carried out by treatment with ozone, as well as with organic hypohalite compounds, such as lower alkyl hypochlorites, for example tert.-butyl hypochlorite, which are used in the presence of inert solvents, such as optionally halogenated hydrocarbons, for example methylene chloride, and at temperatures from about −10° C. to about +30° C., with periodate compounds, such as alkali metal periodates, for example potassium periodate, which are preferably used in an aqueous medium at a pH value of about 6 and at temperatures from about −10° C. to about +30° C., with iodobenzene dichloride, which is used in an aqueous medium, preferably in the presence of an organic base, for example pyridine, and with cooling, for example at temperatures from about −20° C. to about 0°, or with any other oxidising agent which is suitable for conversion of a thio grouping into a sulphoxide grouping.

When oxidising 2-cephem compounds of the formula IB to the 1-oxides or di-S-oxides it is possible, if the reaction is carried out in a non-polar solvent, for example tetrahydrofurane or chloroform, for the S-oxides of 2-cephem compounds initially to be formed preferentially; these can be isomerised easily to the S-oxides of the corresponding 3-cephem compounds by treatment with acids, for example formic acid, or with polar solvents, such as dimethylsulphoxide or dimethylformamide, or also by customary working up in aqueous solvents.

In the S-oxides of 3-cephem compounds of the formula IA, thus obtainable, especially in those compounds in which $R_1{}^a$, $R_1{}^b$ and $R_2$ have the abovementioned preferred meanings, the groups $R_1{}^a$, $R_1{}^b$ and/or $R_2$ can, within the defined framework, be converted into one another, split off or introduced. A mixture of isomeric α- and β-1-oxides can be separated, for example chromatographically.

The reduction of the S-oxides of 3-cephem compounds of the formula IA can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable support, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions, which are used in the form of appropriate inorganic or organic salts, such as alkali metal salts, for example sodium dithionite or potassium dithionite, sodium iodide or potassium iodide or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acid, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, di- or tri-chlorosilane, di- or tri-bromosilane, diphenylchlorosilane, dimethylchlorosilane and the like; reducing quaternary chloromethylene-iminium salts, especially the chlorides or bromides, wherein the iminium group is substituted by one divalent or by two monovalent organic radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which are above all employed together with the dithionite, iodide or ferrocyanide reducing agents and the trivalent phosphorus reducing agents which do not contain halogen, or in the catalytic reduction, there should be mentioned in particular organic carboxylic acid halides and sulphonic acid halides, as well as sulphur halides, phosphorus halides or silicon halides having a second order hydrolysis constant equal to or greater than that of benzoyl chloride, for example phosgene, oxalyl chloride, acetic acid chloride or acetic acid bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane, and also suitable acid anhydrides, such as trifluoroacetic anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting materials and the choice of the reducing agent, thus, for example, lower alkanecarboxylic acids or esters thereof, such as acetic acid and ethyl acetate, are used in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylsulphone, and the like are used together with the chemical reducing agents, these solvents preferably not containing any water. The reaction is usually carried out at temperatures from about $-20°$ C. to about $100°$ C., it being possible to carry out the reaction at lower temperatures, if very reactive activating agents are used.

In the 3-cephem compounds of the formula IA, thus obtainable, $R_1{}^a$, $R_1{}^b$ and/or $R_2$ can be converted into other groups $R_1{}^a$, $R_1{}^b$ or $R_2$, as described above; it must be taken into account that the 3-cephem compounds are considerably more sensitive towards basic agents than the corresponding 2-cephem compounds of the formula IB.

It is also possible to isomerise 3-cephem compounds to 2-cephem compounds in a manner which is in itself known and this reaction can be carried out by treatment with a base, preferably an organic base, such as a heterocyclic base, for example pyridine, and/or a tertiary amine, such a tri-lower alkylamine, for example triethylamine, and, if a free 3-cephem-4-carboxylic acid compound is used, additionally in the presence of a suitable acid derivative which is able to form a mixed anhydride group, such as a carboxylic acid anhydride, such as a lower alkanecarboxylic acid anhydride, for example acetic anhydride. The desired 2-cephem compound can be isolated from an equilibrium mixture of the 2- and 3-cephem compounds, which may be obtained, in a manner which is in itself known.

Salts of compounds of the formulae IA and IB can be manufactured in a manner which is in itself known. Thus, salts of such compounds having acid groups can be formed, for example, by treatment with metal compounds, such as alkali metal salts of suitable carboxylic acids, for example the sodium salt of α-ethyl-caproic acid, or with ammonia or a suitable organic amine, preferably using stoichiometric amounts or only a small excess of the salt-forming agent. Acid addition salts of compounds of the formulae IA and IB having basic groupings are obtained in the customary manner, for example by treatment with an acid or with a suitable anion exchange reagent. Inner salts of compounds of the formulae IA and IB which contain a salt-forming amino group and a free carboxyl group can be formed, for example, by neutralising salts, such as acid addition salts, to the isoelectric point, for example using weak bases, or by treatment with liquid ion exchangers. Salts of 1-oxides of compounds of the formula IA having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers by methods which are in themselves known; for example, mixtures of diastereomeric isomers can be separated by fractional crystallisation, adsorption chromatography (column chromatography or thin layer chromatography) or other suitable separation processes. Resulting racemates can be resolved into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds initially mentioned as being particularly preferred are obtained.

The starting materials of the formula II and their 1-oxides, which are used according to the invention, are new and are also a subject of the present invention. They can be prepared, for example, by converting the 3-hydroxyl group in a cephem compound of the formula

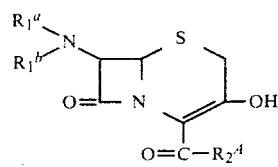

(VI)

wherein $R_1^a$, $R_1^b$ and $R_2^A$ have the meaning indicated under formula IA or IB, or in a 1-oxide thereof, into a 3—O—SO$_2$—R$_4$ group and, if desired, within the definition of the end products, converting a resulting compound into another compound and/or, if desired, separating a resulting mixture of isomeric compounds into the individual isomers.

In a starting material of the formula VI, the radicals $R_1^a$, $R_1^b$ and $R_2^A$ preferably have the same meaning as is indicated for the preferred starting materials of the formula II. The starting material of the formula VI can also be employed in the form of its ketone and enolised only during the esterification reaction.

The esterification of the hydroxyl group in the 3-position in a compound of the formula VI is carried out in a manner which is in itself known with a sulphonic acid of the formula HO—SO$_2$—R$_4$ or with a reactive derivative thereof in an inert solvent and, if necessary, in the presence of a suitable condensing agent, with cooling, at room temperature or with warming, for example at temperatures between about $-10°$ C. and the boiling point of the solvent used, preferably at about $0°$ C. up to room temperature. Suitable reactive sulphonic acid derivatives are, in particular, corresponding halides, such as fluorides or chlorides. Examples of suitable inert solvents are aliphatic, cycloaliphatic or aromatic hydrocarbons, which are optionally substituted, such as halogenated, for example fluorinated or chlorinated, such as hexane, cyclohexane, benzene, toluene, xylene, methylene chloride, chloroform or carbon tetrachloride, ether-like solvents, such as di-lower alkyl ethers, for example diethyl ether of diisopropyl ether, 1,2-dimethoxyethane, tetrahydrofurane or dioxane, di-lower lower alkylamides, such as N,N-dimethylformamide or N,N-dimethylacetamide, lower alkylnitriles, such as acetonitrile, di-lower alkyl sulphides, such as dimethyl sulphide, di-lower alkylsulphoxides, such as dimethylsulphoxide, or mixtures thereof. When sulphonic acids are used, suitable condensing agents are, for example, carbodiimide compounds, such as dicyclohexylcarbodiimide, or carbonyl compounds, such as diimidazolylcarbonyl. When reactive sulphonic acid derivatives are used it is possible to use basic condensing agents, such as tertiary amines, for example tri-lower alkylamines, such as triethylamine, or heterocyclic bases, such as pyridine, or also alkali metal carbonates or bicarbonates or alkaline earth metal carbonates or bicarbonates, such as sodium carbonate or bicarbonate or potassium carbonate or bicarbonate, or alkali metal alcoholates of sterically hindered alcohols, such as potassium tert.-butylate.

A resulting compound of the formula II, or a resulting 1-oxide thereof, can be converted into another compound of the formula II or a 1-oxide thereof and, whilst avoiding reactions in which the —O—SO$_2$—R$_4$ group is split off, it is possible to carry out reactions which are the same in principle as those indicated above for the conversion of the end products of the formula IA and IB or of the 1-oxides thereof. Resulting mixtures of isomers can be separated into the individual isomers by methods analogous to those indicated above for mixtures of isomers of compounds of the formulae IA and IB and 1-oxides thereof.

Starting materials of the formula IV and their 1-oxides are new and are also a subject of the present invention. They can be obtained by subjecting a compound of the formula

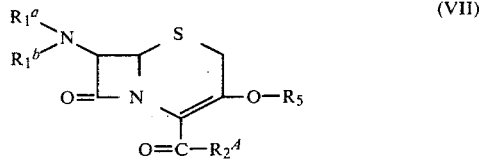

(VII)

wherein $R_1^a$, $R_1^b$, $R_2^A$ and $R_5$ have the meanings indicated under the formula IV, or a 1-oxide thereof, to an addition reaction with a thiol of the formula HS—R$_3$ (III) and, if desired, within the definition of the end products, converting a resulting compound into another compound and/or, if desired, separating a resulting mixture of isomeric compounds into the individual isomers.

In a starting material of the formula VII, the radicals $R_1^a$, $R_1^b$ and $R_2^A$ preferably have the same meaning as indicated for the preferred starting materials of the formula IV.

Thiols of the formula III which are suitable for the addition reaction are, in particular, those in which R$_3$ represents an optionally substituted hydrocarbon radical or an optionally substituted heterocyclic radical and in which the carbon atom bonded to the mercapto group is saturated, that is to say does not form a double bond.

Surprisingly, the addition reaction of the thiol of the formula HS—R$_3$ (III) at the 3,4-double bond of a compound of the formula VII takes place stereospecifically under the conditions of the Michael addition. The reaction takes place in a suitable solvent in the presence of a base which forms the nucleophilic anion $\ominus$S—R$_3$ from the thiol HS—R$_3$, the proton being split off. Such bases are, for example, bicyclic amidines, such as diazabicycloalkenes, for example 1,5-diazabicyclo[4.3.0]non-5-ene or 1,5-diazabicyclo[5.4.0]undec-5-ene, substituted guanidines, for example guanidines which are polysubstituted by lower alkyl, such as tetramethylguanidine, and especially alkali metal hydrides, amides and alcoholates, such as sodium hydride, sodium amide or lithium amide or sodium alcoholates, lithium alcoholates or potassium alcoholates of lower alkanols, such as methanol, ethanol, propanol, isopropanol, butanol or tert.-butanol, for example sodium methylate or sodium ethylate, or preferably potassium tert.-butylate, as well as alkali metal hydrocarbons, especially of lithium, such as lower alkyl-lithium or aryl-lithium, for example ethyl-, n-butyl-, sec.-butyl-, tert.-butyl- or phenyl-lithium. Suitable solvents are, for example, aliphatic, cycloaliphatic or aromatic, optionally substituted, ether-like solvents, such as di-lower alkyl ethers, for example diethyl ether or diisopropyl ether, 1,2-dimethoxyethane, tetrahydrofurane or dioxane, di-lower alkylamides, such as N,N-dimethylformamide, N,N-dimethylacetamide or N,N-diethylacetamide, lower alkylnitriles, such as acetonitrile, di-lower alkyl sulphides, such as dimethyl sulphide, di-lower alkylsulphoxides, such as dimethylsulphoxide, or mixtures thereof. The reaction is carried out with cooling, that is to say at temperatures between about −80° C. and about −58° C., preferably at about −78° C., if appropriate in an inert gas atmosphere, for example a nitrogen atmosphere. Surprisingly, at low temperatures only the sterically homogeneous compounds of the formula IV are formed and not the 3β-(O—R$_5$)—3α—(—S—R$_3$)—cepham-4α-carboxylic acid derivatives which are epimeric thereto; the latter are formed in increased amounts only at higher temperatures.

It is also possible to use 2-cephem compounds analogous to the compounds of the formula VII, or mixtures of corresponding 2- and 3-cephem compounds, in the addition reaction, in which case, under basic addition reaction conditions, the 2,3-double bond is first rearranged into a 3,4-double bond, after which the addition of the thiol HS—R$_3$ (III) takes place in the desired manner.

A resulting compound of the formula IV, or a resulting 1-oxide thereof, can be converted into another compound of the formula IV or a 1-oxide thereof, it being possible, whilst avoiding reactions in which elimination of HO—R$_5$ occurs, to carry out reactions which are the same in principle as indicated above for the conversion of the end products of the formula IA and IB, or of their 1-oxides. Resulting mixtures of isomers can be separated into the individual isomers by methods analogous to those indicated above for mixtures of isomers of compounds of the formulae IA and IB and 1-oxides thereof. In the case of compounds of the formula IV and 1-oxides thereof, attention must be paid, in particular, to the separation of 3β-(O—R$_5$)-3α-(S—R$_3$)-cepham-4β-carboxylic acid derivatives and 3β-(O—R$_5$)-3α-(S—R$_3$)-4α-carboxylic acid derivatives, which can be carried out, for example, by chromatographic methods and/or fractional crystallisation.

Compounds of the formula V and their 1-oxides are new and are also a subject of the present invention. They can be prepared, for example, by replacing the group R$_6$ in a compound of the formula

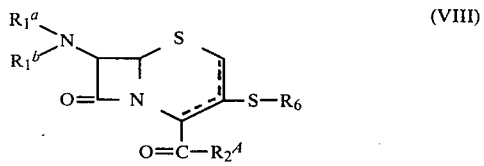

(VIII)

wherein R$_1{}^a$, R$_1{}^b$ and R$_2{}^A$ have the meaning indicated under formula IA or IB and R$_6$ denotes an optionally substituted triarylmethyl group and wherein the double bond is in the 2,3-position or 3,4-position, or in a 1-oxide thereof, by hydrogen and, if desired, within the definition of the end products, converting a resulting compound into another compound and/or, if desired, separating a resulting mixture of isomeric compounds into the individual isomers.

In a starting material of the formula VIII, R$_6$, as an optionally substituted triarylmethyl group, is, in particular, the triphenylmethyl group, wherein the phenyl rings are preferably unsubstituted or optionally carry one or more substituents, such as lower alkyl, for example methyl, lower alkoxy, for example methoxy, or halogen, for example fluorine or chlorine. Other possible aryl groups are naphthyl groups which are optionally substituted as above, for example 1-, 2- or 4-naphthyl, it being possible for the aryl groups to be either identical or different, within the defined scope.

The optionally substituted triarylmethyl group R$_6$ is split off in a manner which is in itself known, for example by treatment with a heavy metal salt, the solubility product of which is greater than that of the heavy metal sulphide formed, for example with a heavy metal nitrate, acetate, or sulphate, such as silver nitrate, mercury-II diacetate or copper-II sulphate, or also a soluble chloride, such as tin-II chloride dihydrate. The compound of the formula V can then be liberated from the heavy metal sulphide, which may be obtained initially, by treatment with an acid which forms a more sparingly soluble salt with the heavy metal.

The optionally substituted triarylmethyl group R$_6$ can also be split off directly under the action of a suitable acid agent, such as formic acid or trifluoroacetic acid, it being possible to carry out the reaction in one of the above-mentioned inert solvents.

The reaction of a compound of the formula VIII with the heavy metal salt can be carried out in an inert organic solvent, in water or in a solvent mixture consisting of water and a water-miscible solvent. Suitable inert organic solvents are, for example, aliphatic, cycloaliphatic or aromatic hydrocarbons, such as pentane, hexane, cyclohexane, benzene, toluene or xylene, or aliphatic, cycloaliphatic or aromatic alcohols, such as lower alkanols, for example methanol or ethanol, cyclohexanol or phenol, polyhydroxy compounds, such as polyhydroxyalkanes, for example, a dihydroxylower alkane, such as ethylene glycol or propylene glycol, carboxylic acid esters, for example lower carboxylic acid lower alkyl esters, such as ethyl acetate, lower ketones, such as acetone or methyl ethyl ketone, ether-like solvents, such as dioxane or tetrahydrofurane, or polyethers, such as dimethoxyethane, lower carboxylic acid amides, such as dimethylformamide, lower alkylnitriles, such as acetonitrile or lower sulphoxides, such as dimethylsulphoxide. The reaction usually proceeds considerably more rapidly in water or especially in mixtures of water and one of the solvents mentioned, including in emulsions, than in the organic solvents alone.

The reaction temperature is usually room temperature but can be lowered to slow down the reaction or raised, say up to the boiling point of the solvent employed, to accelerate the reaction, and it is possible to carry out the reaction under normal or elevated pressure.

Compounds of the formula V can also be prepared by treating a compound of the formula VII, wherein R$_1{}^a$, R$_1{}^b$, R$_1{}^A$ and R$_5$ have the meaning indicated under the formula IV, or a 1-oxide thereof, with a bisulphide and, if desired, within the definition of the end products, converting a resulting compound into another compound and/or, if desired, separating a resulting mixture of isomeric compounds into the individual isomers. Bisulphides which can be used according to the invention contain a metal cation or ammonium cation as the ion of opposite charge.

Suitable bisulphides are, in particular, alkali metal bisulphides, such as sodium bisulphide, lithium bisulphide or potassium bisulphide and also quaternary ammonium bisulphides, such as ammonium bisulphides which are monosubstituted to trisubstituted and especially tetrasubstituted by lower alkyl, cycloalkyl or aryl-lower alkyl, for example tetramethylammonium bisulphide, tetraethylammonium bisulphide, benzyltrimethylammonium bisulphide or benzyl-triethylammonium bisulphide. The reaction is carried out in a suitable solvent, optionally in the presence of a strong base, such as a bicyclic amidine, for example a diazabicycloalkene, such as 1,5-diazabicyclo[4.3.0]non-5-ene or 1,5-diazabicyclo[5,4,0]undec-5-ene, or a substituted guanidine, for example guanidine polysubstituted by lower alkyl, such as tetramethylguanidine. Suitable solvents are, for example, aliphatic cycloaliphatic or aromatic, optionally substituted, ether-like solvents, such as di-lower alkyl ethers, for example diethyl ether or diisopropyl ether, 1,2-dimethoxyethane, tetrahydrofurane or dioxane, di-lower alkylamides, such as N,N-dimethylformamide, N,N-dimethylacetamide or N,N-diethylacetamide, lower alkylnitriles, such as acetonitrile, di-lower alkyl sulphides, such as dimethyl sulphide, di-lower alkylsulphoxides, such as dimethylsulphoxide, or mixtures thereof. The reaction is carried out with cooling, that is to say at temperatures between about −80° C. and about 0° C., preferably at about −5° C., if appropriate in an inert gas atmosphere, for example a nitrogen atmosphere.

A resulting compound of the formula V, or a 1-oxide thereof, can be converted into another compound of the formula V or a 1-oxide thereof, it being possible, if necessary, to protect the -SH group in the 3-position and to liberate this again after the reaction has taken place and to carry out reactions which in principle are the same as those indicated above for the conversion of the end products of the formula IA and IB, or of their 1-oxides. Resulting mixtures of isomers can be separated into the individual isomers by methods analogous to those indicated above for mixtures of isomers of compounds of the formula IA and IB or 1-oxides thereof.

The pharmacologically usable compounds of the present invention can be used, for example, to produce pharmaceutical preparations which contain an effective amount of the active substance together or in a mixture with inorganic or organic, solid or liquid, pharmaceutically usable excipients, which are suitable for enteral or parenteral administration. Thus, tablets or gelatine capsules are used, which contain the active substance together with excipients, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorption agents, colorants, flavourings and sweeteners. The new pharmacologically active compounds can also be used in the form of injectable preparations, for example preparations which can be administered intravenously, or infusion solutions. Such solutions are preferably isotonic aqueous solutions or suspensions and these can be prepared before use, for example from lyophilised preparations which contain the active substance alone or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which, if desired, can contain further pharmacologically valuable substances, are produced in a manner which is in itself known, for example by means of conventional mixing, granulating, dragee-making, dissolving or lyophilising processes, and contain from about 0.1% to 100%, especially from about 1% to about 50%, of lyophilisates, up to 100% of the active substance.

In the context of the present description, the organic radicals described as "lower" contain, unless expressly defined, up to 7, preferably up to 4, carbon atoms; acyl radicals contain up to 20, preferably up to 12, and above all up to 7, carbon atoms.

The examples which follow serve to illustrate the invention.

EXAMPLE 1

A solution of 0.96 g (1.62 mmols) of 7β-phenylacetylamino-3-phenylthio-3-cephem-4-carboxylic acid diphenylmethyl ester and 0.26 ml (2.43 mmols) of anisole in 9.6 ml of methylene chloride is stirred with 1.24 ml (16.2 mmols) of trifluoroacetic acid for 30 minutes at 0° C. and the mixture is treated with 50 ml of cold toluene and evaporated in vacuo and the residue is dried in a high vacuum. The residue is digested with diethyl ether, filtered off, rinsed with the same solvent and dried in vacuo. 7β-Phenylacetylamino-3-phenylthio-3-cephem-4-carboxylic acid is obtained as a microcrystalline, colourless powder which can be recrystallised from acetone/methylene chloride/diethyl ether. Melting point 190° C. (decomposition). Thin layer chromatogram (silica gel): Rf ~0.60 (n-butanol/pyridine/acetic acid/$H_2O$, 40:24:6:30); UV spectrum (ethanol): $\lambda_{max}$=263 nm ($\epsilon$=7000); 305 nm ($\epsilon$=9000); IR spectrum (nujol): characteristic bands at 3.02; 5.59; 5.81; 6.01; 6.22 and 6.48μ.

The starting material can be prepared as follows:

(a) 5.72 g (30 mmols) of tosyl chloride are added to a solution of 10.0 g (20 mmols) of 7β-phenylacetylamino-3-hydroxy-3-cephem-4-carboxylic acid diphenylmethyl ester in 50 ml of pyridine at 0° C. and the mixture is stirred for 3 hours under nitrogen in an ice bath. The reaction mixture is poured onto ice water and extracted twice with ethyl acetate. The organic phases are extracted by shaking three times with 2 N hydrochloric acid, three times with saturated aqueous sodium bicarbonate solution and three times with saturated aqueous sodium chloride solution, dried over sodium sulphate and evaporated in vacuo. The residue is chromatographed on 400 g of silica gel. Toluene, containing 10-15% of ethyl acetate, elutes a mixture consisting of 7β-phenylacetylamino-3-p-toluene-sulphonyloxy-3-cephem-4-carboxylic acid diphenylmethyl ester and 7β-phenylacetylamino-3-p-toluenesulphonyloxy-2-cephem-4α-carboxylic acid diphenylmethyl ester. Thin layer chromatogram (silica gel) Rf ~0.58 (3-cephem derivative), Rf ~0.54 (2-cephem derivative) (toluene-/ethyl acetate, 3:1); IR spectrum ($CH_2Cl_2$): characteristic bands of the 2-cephem derivative at 2.94; 5.60; 5.71; 5.92; 6.25 and 6.67μ; characteristic bands of the 3-cephem derivative at 2.94; 5.58; 5.75; 5.92; 6.24 and 6.67μ.

(b) A solution of 4.0 g (6.12 mmols) of the mixture obtained according to (a), which consists of 7β-phenylacetylamino-3-p-toluenesulphonyloxy-3-cephem-4-carboxylic aciddiphenylmethyl ester and 7β-phenylacetylamino-3-p-toluenesulphonyloxy-2-cephem-4α-carboxylic acid diphenylmethyl ester, in 80 ml of methylene chloride is stirred with 1.36 g (6.70 mmols) of m-chloroperbenzoic acid for 1 hour at 0° C. and the mixture is then concentrated in vacuo. The residue is taken up in ethyl acetate and the solution is extracted by shaking with saturated aqueous sodium bicarbonate solution and saturated aqueous sodium chloride solution, dried over sodium sulphate and evaporated in vacuo. The residue is chromatographed on 150 g of silica gel. Toluene/ethyl acetate, 4:1, elutes 7β-phenylacetylamino-3-p-toluenesulphonyloxy-3-cephem-4-carboxylic acid diphenylmethyl ester 1-oxide, which is recrystallised from acetone/diethyl ether; melting point 163°–165° C. (decomposition). UV spectrum (ethanol): $\lambda_{max}=270$ nm ($\epsilon=5300$); IR spectrum ($CH_2Cl_2$): characteristic bands at 2.94; 5.53; 5.73; 5.89; 6.24; 6.61 and 6.67μ. Thin layer chromatogram (silica gel): Rf ~0.43 (toluene/ethyl acetate, 1:1).

(c) 0.694 ml (4.02 mmols) of N-ethyl-N,N-diisopropylamine is added dropwise in the course of 5 minutes to a solution, cooled to 0° C., of 2.15 g (3.22 mmols) of 7β-phenylacetylamino-3-p-toluenesulphonyloxy-3-cephem-4-carboxylic acid diphenylmethyl ester 1-oxide and 0.496 ml (4.82 mmols) of thiophenol in 21.5 ml of dimethylformamide. The reaction mixture is stirred for a further 10 minutes in an ice bath and then diluted with ethyl acetate and washed successively with ice-cold 2 N hydrochloric acid, saturated aqueous sodium bicarbonate solution and saturated aqueous sodium chloride solution. The organic phase is dried over sodium sulphate, filtered and evaporated in vacuo. The residue is chromatographed on 90 g of silica gel. Toluene containing 20-25% of ethyl acetate elutes 7β-phenylacetylamino-3-phenylthio-3-cephem-4-carboxylic acid diphenylmethyl ester 1-oxide. which can be crystallised from methylene chloride/diethyl ether; melting point 180° C. (decomposition). Thin layer chromatogram (silica gel): Rf ~0.31 (toluene/acetone, 5:1); IR spectrum (nujol): characteristic bands at 3.02; 5.61; 5.83; 5.97; 6.54 and 9.56μ. UV spectrum (ethanol): $\lambda_{max}=260$ nm ($\epsilon=7200$); 319 nm ($\epsilon=10900$).

(d) A solution, cooled to 0° C., of 1.08 g (1.78 mmols) of 7β-phenylacetylamino-3-phenylthio-3-cephem-4-carboxylic acid diphenylmethyl ester 1-oxide in 10.8 ml of methylene chloride is stirred with 0.54 ml of dimethylacetamide and 0.311 ml (3.56 mmols) of phosphorus trichloride for 15 minutes in an ice bath and the mixture is then diluted with ethyl acetate and washed successively with ice-cold 2 N hyrochloric acid, saturated aqueous sodium bicarbonate solution and saturated aqueous sodium chloride solution. The organic phase is dried over sodium sulphate, filtered and evaporated in vacuo. The residue is chromatographed on silica gel thick layer plates with toluene/ethyl acetate, 3:1, as the running agent and this gives 7β-phenylacetylamino-3-phenylthio-3-cephem-4-carboxylic acid diphenylmethyl ester. Thin layer chromatogram (silica gel): Rf ~0.38 (toluene/ethyl acetate, 3:1); UV spectrum (ethanol): $\lambda_{max}=260$ nm ($\epsilon=7600$); 312 nm ($\epsilon=9100$); IR spectrum ($CH_2Cl_2$): characteristic bands at 2.94; 5.60; 5.77; 5.92 and 6.66μ.

EXAMPLE 2

A solution of 1.68 g (2.56 mmols) of a mixture of 7β-phenylacetylamino-3-p-toluenesulphonyloxy-3-cephem-4-carboxylic acid diphenylmethyl ester and 7β-phenylacetylamino-3-p-toluenesulphonyloxy-2-cephem-4α-carboxylic acid diphenylmethyl ester in 17 ml of dimethylformamide is stirred with 0.27 ml (2.56 mmols) of thiophenol and 0.44 ml (2.56 mmols) of N-ethyl-N,N-diisopropylamine for 15 minutes at 0° C. and for 45 minutes at room temperature. The reaction mixture is diluted with ethyl acetate and washed successively with ice-cold 2 N hydrochloric acid, saturated aqueous sodium bicarbonate solution and saturated aqueous sodium chloride solution. The organic phase is dried over sodium sulphate, filtered and evaporated in vacuo. The residue is chromatographed on 45 g of silica gel. Toluene/ethyl acetate, 3:1, elutes a mixture consisting of 7β-phenylacetylamino-3-phenylthio-3-cephem-4-carboxylic acid diphenylmethyl ester and 7β-phenylacetylamino-3-phenylthio-2-cephem-4α-carboxylic acid diphenylmethyl ester; thin layer chromatogram: double spot at a Rf value ~0.41 (silica gel; toluene/ethyl acetate, 3:1); IR spectrum (in methylene chloride): characteristic bands at 2.94; 5.59; 5.76; 5.90 and 6.66μ.

The mixture of isomers obtained can be converted into the S-oxides as follows:

(a) A solution of 410 mg (2.03 mmols) of m-chloroperbenzoic acid in 10 ml of methylene chloride is added to a solution of 1.10 g (1.85 mmols) of a mixture of isomers consisting of 7β-phenylacetylamino-3-phenylthio-3-cephem-4-carboxylic acid diphenylmethyl ester and 7β-phenylacetylamino-3-phenylthio-2-cephem-4α-carboxylic acid diphenylmethyl ester in 11 ml of methylene chloride at 0° C. and the mixture is stirred in an ice bath for 30 minutes. The reaction mixture is diluted with ethyl acetate and washed successively with saturated aqueous sodium bicarbonate solution and saturated aqueous sodium chloride solution and the organic phase is dried over sodium sulphate and evaporated in vacuo. The residue is chromatographed on silica gel thick layer plates with toluene/ethyl acetate, 1:1. 7β-Phenylacetylamino-3-phenylthio-3-cephem-4-carboxylic acid diphenylmethyl ester 1-oxide of Rf value ~0.38 (silica gel; toluene/ethyl acetate, 1:1) is obtained and after recrystallisation from methylene chloride/diethyl ether melts at 180° C. with decomposition.

7β-Phenylacetylamino-3-phenylsulphinyl-3-cephem-4-carboxylic acid diphenylmethyl ester 1-oxide can be isolated as the more polar product of Rf value ~0.08 (silica gel; toluene/ethyl acetate, 1:1); IR spectrum (in methylene chloride): characteristic bands at 2.93; 5.52; 5.75; 5.86; 6.18 and 6.63μ.

EXAMPLE 3

1.03 ml (6.0 mmols) of N-ethyl-N,N-diisopropylamine are added in the course of 5 minutes to a solution of 3.15 g (4.0 mmols) of 7β-(D-α-tert.-butoxycarbonylamino-α-phenylacetylamino)-3-p-toluenesulphonyloxy-3-cephem-4-carboxylic acid diphenylmethyl ester 1-oxide and 0.823 ml (8.0 mmols) of thiophenol in 31.5 ml of dimethylformamide at 0° C. and the mixture is stirred for 30 minutes at 0° C. The reaction mixture is diluted with ethyl acetate and washed successively with 2 N hydrochloric acid, saturated aqueous sodium bicarbonate solution and saturated aqueous sodium chloride solution. The organic phase is dried over sodium sulphate and evaporated in vacuo. The residue is digested with diethyl ether and left to stand overnight at −10° C. and this gives 7β-(D-α-tert.-butoxycarbonylamino-α-phenylacetylamino)-3-phenylthio-3-cephem-4-carboxylic acid diphenylmethyl ester 1-oxide of melting point 190° C. (decomposition); thin layer chromatogram: Rf value ~0.13 (silica gel; toluene/ethyl acetate, 3:1), UV spectrum (ethanol): $\lambda_{max}=260$ mμ

($\epsilon = 7200$); IR spectrum (in methylene chloride): characteristic bands at 2.93; 5.54; 5.83; 5.88 and 6.68$\mu$.

The product can be further processed as follows:

(a) A solution of 1.45 g (2.0 mmols) of 7$\beta$-(D-$\alpha$-tert.-butoxycarbonylamino-$\alpha$-phenyl-acetylamino)-3-phenylthio-3-cephem-4-carboxylic acid diphenylmethyl ester 1-oxide in 14.5 ml of methylene chloride is stirred with a mixture of 0.35 ml (4.0 mmols) of phosphorus trichloride in 0.72 ml of dimethylacetamide for 15 minutes at 0° C. The reaction mixture is diluted with ethyl acetate and washed successively with ice water, saturated aqueous sodium bicarbonate solution and saturated aqueous sodium chloride solution. The organic phase is dried over sodium sulphate and evaporated in vacuo. The residue is chromatographed on silica gel thick layer plates with toluene/ethyl acetate, 3:1, as the running agent. 7$\beta$-(D-$\alpha$-Tert.-butoxycarbonylamino-$\alpha$-phenyl-acetylamino)-3-phenylthio-3-cephem-4-carboxylic acid diphenylmethyl ester of melting point 174°–176° C. (from methylene chloride/hexane) is eluted; Rf value ~0.40 (silica gel; toluene/ethyl acetate, 3:1); UV spectrum (ethanol): $\lambda_{max}=260$ m$\mu$ ($\epsilon=7400$); 313 m$\mu$ ($\epsilon=9300$).

(b) 3.9 ml (52 mmols) of pre-cooled trifluoroacetic acid are added to a solution of 916 mg (1.30 mmols) of 7$\beta$-(D-$\alpha$-tert.-butoxycarbonylamino-$\alpha$-phenyl-acetylamino)-3-phenylthio-3-cephem-4-carboxylic acid diphenylmethyl ester in 4.6 ml of methylene chloride in an ice bath and the mixture is stirred for 30 minutes. After adding 50 ml of cold toluene, the reaction mixture is evaporated in vacuo. 100 ml of chloroform/toluene, 1:1, are added to the residue and the mixture is again evaporated in vacuo and the residue is then digested with diethyl ether, filtered off and washed with diethyl ether. The resulting trifluoroacetate of 7$\beta$-(D-$\alpha$-phenylglycylamino)-3-phenylthio-3-cephem-4-carboxylic acid is suspended in 5.6 ml of water and the pH value of the suspension is adjusted to 4.5 with a 10% strength solution of triethylamine in methanol. 10 ml of acetone are then added and the mixture is left to stand overnight at 10° C. The precipitate is filtered off, washed with acetone and diethyl ether and dried in vacuo. The resulting inner salt of 7$\beta$-(D-$\alpha$-phenylglycylamino)-3-phenylthio-3-cephem-4-carboxylic acid is a colourless powder; UV spectrum (0.01 N hydrochloric acid): $\lambda_{max}=260$ m$\mu$ ($\epsilon=5800$); 313 m$\mu$ ($\epsilon=9000$).

The starting material and the intermediate products can be obtained as follows:

(c) A solution of 10.0 g (16.2 mmols) of 7$\beta$-(D-$\alpha$-tert.-butoxycarbonylamino-$\alpha$-phenylacetylamino)-3-hydroxy-3-cephem-4-carboxylic acid diphenylmethyl ester in 50 ml of pyridine is stirred with 4.02 g (21.1 mmols) of p-toluenesulphonyl chloride for 2 hours at about $-10°$ C. and for 1 hour in an ice bath. The reaction mixture is poured onto ice water and extracted twice with ethyl acetate. The combined organic phases are washed three times with 2 N hydrochloric acid and then with saturated aqueous sodium bicarbonate solution and saturated aqueous sodium chloride solution, dried over sodium sulphate and evaporated in vacuo. The residue is chromatographed on 400 g of silica gel. Toluene containing 10% of ethyl acetate elutes a mixture consisting of 7$\beta$-(D-$\alpha$-tert.-butoxycarbonylamino-$\alpha$-phenyl-acetylamino)-3-p-toluenesulphonyloxy-3-$\alpha$-cephem-4-carboxylic acid diphenylmethyl ester and 7$\beta$-[D-$\alpha$-tert.-butoxycarbonylamino-$\alpha$-phenylacetylamino]-3-p-toluenesulphonyloxy-2-cephem-4-carboxylic acid diphenylmethyl ester of Rf value ~0.4 (silica gel; toluene/ethyl acetate, 1:1).

(d) A solution of 8.28 g (1.08 mmols) of a mixture, obtained according to Example 3(e), of 7$\beta$-(D-$\alpha$-tert.-butoxycarbonylamino-$\alpha$-phenyl-acetylamino)-3-p-toluenesulphonyloxy-3-cephem-4-carboxylic acid diphenylmethyl ester and 7$\beta$-(D-$\alpha$-tert.-butoxycarbonylamino-$\alpha$-phenyl-acetylamino)-3-p-toluenesulphonyloxy-2-cephem-4-carboxylic acid diphenylmethyl ester in 166 ml of methylene chloride is stirred with 2.40 g (1.18 mmols) of m-chloroperbenzoic acid for 1 hour in an ice bath and the mixture is then concentrated in vacuo. The residue is diluted with ethyl acetate and washed successively with saturated aqueous sodium bicarbonate solution and saturated aqueous sodium chloride solution and the organic phase is dried over sodium sulphate and evaporated in vacuo. The crude product is chromatographed on 200 g of silica gel. Toluene containing 20% of ethyl acetate elutes 7$\beta$-(D-$\alpha$-tert.-butoxycarbonylamino-$\alpha$-phenyl-acetylamino)-3-p-toluenesulphonyloxy-3-cephem-4-carboxylic acid diphenylmethyl ester 1-oxide of melting point 130°–133° C. (from methylene chloride/diethyl ether); $[\alpha]_D^{20}=-12°\pm1°$ (c=0.906; chloroform); thin layer chromatogram: Rf value ~0.11 (silica gel; toluene/ethyl acetate, 3:1); UV spectrum (ethanol): $\lambda_{max}=270$ m$\mu$ ($\epsilon=8800$); 275 m$\mu$ ($\epsilon=8700$); IR spectrum (nujol): characteristic bands at 2.98; 5.57; 5.76; 5.92; 6.03; 6.25; 6.57 and 6.68$\mu$.

EXAMPLE 4

A solution of 192 mg (4 mmols) of methylmercaptan in 8 ml of methylene chloride and 0.52 ml (3 mmols) of N-ethyl-N,N-diisopropylamine is added to a solution of 0.785 g (1 mmol) of 7$\beta$-(D-$\alpha$-tert.-butoxycarbonylamino-$\alpha$-phenylacetylamino)-3-p-toluenesulphonyloxy-3-cephem-4-carboxylic acid diphenylmethyl ester 1-oxide in 4 ml of dimethylformamide and the mixture is stirred for 24 hours at room temperature under a nitrogen atmosphere. The reaction mixture is diluted with methylene chloride and washed with saturated aqueous sodium chloride solution. The organic phase is dried over sodium sulphate and evaporated in vacuo. The residue is chromatographed on silica gel thick layer plates using toluene/ethyl acetate, 3:1, as the running agent and gives 7$\beta$-(D-$\alpha$-tert.-butoxycarbonylamino-$\alpha$-phenylacetylamino)-3-methylthio-4-carboxylic acid diphenylmethyl ester 1-oxide of melting point 201°–202° C. (from methylene chloride/diethyl ether); thin layer chromatogram: Rf value ~0.2 (silica gel; toluene/ethyl acetate, 1:1); UV spectrum (ethanol): $\lambda_{max}=321$ m$\mu$ ($\epsilon=10600$); IR spectrum (in methylene chloride): characteristic bands at 2.93; 5.56; 5.84; 5.87 sh; 5.90 sh and 6.68$\mu$.

The compound can be further processed as follows:

(a) A solution of 300 mg (0.45 mmol) of 7$\beta$-(D-$\alpha$-tert.-butoxycarbonylamino-$\alpha$-phenyl-acetylamino)-3-methylthio-4-carboxylic acid diphenylmethyl ester 1-oxide in 3 ml of methylene chloride and 0.15 ml of dimethylacetamide is stirred with 0.079 ml of phosphorus trichloride (0.90 mmol) for 15 minutes at 0° C. The reaction mixture is diluted with ethyl acetate and washed with saturated aqueous sodium bicarbonate solution and saturated aqueous sodium chloride solution and the organic phase is dried over sodium sulphate and evaporated in vacuo. The residue is chromatographed on silica gel thick layer plates using toluene/ethyl acetate, 3:1, as the running agent and gives 7$\beta$-(D-$\alpha$-tert.- utoxycarbonylamino-α-phenyl-acetylamino)-3-methylthio-3-cephem-4-carboxylic acid diphenylmethyl ester of Rf value ~0.5 (silica gel: toluene/ethyl acetate, 1:1); UV spectrum (ethanol); $\lambda_{max}=318$ mµ ($\epsilon=9500$); IR spectrum (in methylene chloride): characteristic bands at 2.93; 5.59; 5.80b; 5.92 sh and 6.67µ.

(b) A solution of 200 mg (0.31 mmol) of 7β-(D-α-ert.-butoxycarbonylamino-α-phenyl-acetylamino)-3-methylthio-4-carboxylic acid diphenylmethyl ester in 2 ml of methylene chloride is stirred with 0.167 ml (1.55 mmols) of anisole and 0.05 ml (12.4 mmols) of trifluoroacetic acid for 30 minutes in an ice bath and the mixture is then treated with 20 ml of cold toluene and evaporated in vacuo. The residue is digested several times with diethyl ether and the diethyl ether is decanted off each time. The residue, consisting mainly of the trifluoroacetate of 7β-(D-α-phenylglycylamino)-3-methylthio-3-cephem-4-carboxylic acid, is taken up in 1.5 ml of water. The pH value of the mixture is adjusted to about 4.5 by adding a 10% strength solution of triethylamine in methanol. The precipitation is brought to completion by adding 5 ml of acetone. The precipitate is filtered off, washed with a little cold acetone and diethyl ether and dried. The resulting 7β-(D-α-phenylglycylamino)-3-methylthio-3-cephem-4-carboxylic acid has a melting point of 185° C.; Rf value ~0.40 (silica gel; n-butanol/pyridine/acetic acid/water, 40:24:6:30); UV spectrum (0.01 N hydrochloric acid): $\lambda_{max}=315$ mµ ($\epsilon=9000$), (in water): λmax=292 mµ ($\epsilon=7700$); IR spectrum (nujol): characteristic bands at 3.01; 5.63; 5.87; 6.27 and 6.66µ; $[\alpha]_D^{20}=+70°\pm1°$ (c=1; water).

EXAMPLE 5

A solution of 78.5 mg (0.1 mmol) of 7β-(D-α-tert.-butoxycarbonylamino-α-phenyl-acetylamino)-3-p-toluenesulphonyloxy-3-cephem-4-carboxylic acid diphenylmethyl ester 1-oxide in 0.4 ml of dimethylformamide is stirred with 55.2 mg (0.2 mmol) of tritylmercaptan and 26 µl (0.15 mmol) of N-ethyl-N,N-diisopropylamine for 5 hours at room temperature under a nitrogen atmosphere. The reaction mixture is diluted with ethyl acetate and washed with saturated aqueous sodium bicarbonate solution and saturated aqueous sodium chloride solution. The organic phase is dried over sodium sulphate and evaporated in vacuo. The residue is chromatographed on silica gel thick layer plates using toluene/acetyl acetate, 3:1, as the running agent and gives 7β-(D-α-tert.-butoxycarbonylamino-α-phenylacetylamino)-3-tritylthio-3-cephem-4-carboxylic acid diphenylmethyl ester 1-oxide of Rf value ~0.35 (silica gel; toluene/ethyl acetate, 3:1); IR spectrum (in methylene chloride); characteristic bands at 2.93; 5.57; 5.84; 5.90 sh and 6.57µ.

EXAMPLE 6

A solution of 1.85 ml (~10.9 mmols) of N-ethyl-N,N-diisopropylamine in 29 ml of dimethylformamide is added in the course of 30 minutes to a solution of 4.85 g (7.25 mmols) of 7β-phenylacetamido-3-(p-toluenesulphonyloxy)-3-cephem-4-carboxylic acid diphenylmethyl ester 1-oxide and 1.32 ml (~14.5 mmols) of mercaptoacetic acid methyl ester in 29 ml of dimethylformamide. The mixture is allowed to react for a further 2.5 hours and evaporated in a high vacuum, the residue is dissolved in ethyl acetate and the solution is extracted with 2 N hydrochloric acid, saturated aqueous sodium bicarbonate solution and saturated aqueous sodium chloride solution. The organic phase is dried with sodium sulphate and evaporated. The residue is chromatographed on silica gel with toluene/ethyl acetate 1:1 and gives 7β-phenylacetamido-3-carbomethoxymethylthio-3-cephem-4-carboxylic acid diphenylmethyl ester 1-oxide, which crystallises from methylene chloride/ethyl acetate/hexane; melting point: 208°–212° C.; $[\alpha]_D^{20}=+15°\pm1°$ (c=481, chloroform); UV spectrum (ethanol): $\lambda_{max}=314$ mµ ($\epsilon=8450$); IR spectrum (nujol): characteristic bands at 3.01; 5.58; 5.80; 6.00 and 6.52µ.

The resulting product can be further processed as follows:

(a) A solution, cooled to −10° C., of 1.10 g (~1.82 mmols) of 7β-phenylacetamido-3-carbomethoxy-methylthio-3-cephem-4-carboxylic acid diphenylmethyl ester 1-oxide in 7.3 ml of dimethylformamide is stirred for 15 minutes with 0.32 ml of phosphorus trichloride (~3.64 mmols) and the mixture is then poured onto ice and extracted with ethyl acetate. The organic phase is washed with saturated aqueous sodium bicarbonate solution and saturated aqueous sodium chloride solution, dried over sodium sulphate and evaporated. The residue is chromatographed on 50 g of silica gel, 7β-phenylacetamido-3-carbomethoxy-methylthio-3-cephem-4-carboxylic acid diphenylmethyl ester being eluted with toluene/ethyl acetate; 3:1. After crystallisation from acetone/ethyl acetate/hexane, colourless needles of melting point 152°–154° C. are obtained; $[\alpha]_D^{20}=26°\pm1°$ (c=0.639%; CHCl₃); UV spectrum (ethanol): $\lambda_{max}=303$ mµ ($\epsilon=7600$); IR spectrum (nujol); characteristic bands at 3.03; 5.60; 5.75; 5.84; 6.02 and 6.48µ.

(b) A solution of 0.76 g (1.29 mmols) of 7β-phenylacetamido-3-carbomethoxy-methylthio-3-cephem-4-carboxylic acid diphenylmethyl ester in 7.6 ml of methylene chloride is stirred with 0.21 ml (1.94 mmols) of anisole and 0.99 ml (12.9 mmols) of trifluoroacetic acid for 30 minutes in an ice bath. After adding 40 ml of cold toluene, the mixture is evaporated in vacuo and the residue is triturated with diethyl ether. The pulverulent precipitate is filtered off, washed with diethyl ether and petroleum ether and dried. Microcrystalline 7β-phenylacetamido-3-carbomethoxymethylthio-3-cephem-4-carboxylic acid, which according to thin layer chromatography is a single substance, is obtained. Melting point ~175° C. (decomposition); thin layer chromatogram: silica gel; Rf value ~0.55 (n-butanol/pyridine/acetic acid/H₂O, 40:24:6:30); UV spectrum (ethanol): $\lambda_{max}=296$ mµ ($\epsilon=6800$); IR spectrum (nujol): characteristic bands at 3.03; 3.25; 5.57; 5.75; 5.80; 5.98 and 6.46µ.

EXAMPLE 7

A solution of 2.55 ml (15 mmols) of N-ethyl-N,N-diisopropylamine in 40 ml of dimethylformamide is added, in the course of 1 hour, to a solution of 7.85 g (10 mmols) of 7β-(D(−)-α-tert.-butoxycarbonylamino-α-phenyl-acetylamino)-3-(p-toluenesulphonyloxy)-3-cephem-4-carboxylic acid diphenylmethyl ester 1β-oxide and 1.81 ml (20 mmols) of mercaptoacetic acid methyl ester in 10 ml of dimethylformamide and the mixture is stirred for 1 hour at room temperature. The reaction mixture is taken up in ethyl acetate and washed successively with water, 2 N hydrochloric acid, saturated aqueous sodium bicarbonate solution and saturated aqueous sodium chloride solution. The organic phase is dried over sodium sulphate and evaporated. Chromatography of the crude product on 180 g of silica gel and elution with toluene/ethyl acetate, 1:1, gives 7β-(D(−)-α-tert.butoxycarbonylamino-α-phenylacetylamino)-3-carbomethoxymethylthio-3-cephem-4-carboxylic acid diphenylmethyl ester 1β-oxide, which is recrystallised from methylene chloride/diethyl ether; melting point 173°–175° C.; $[\alpha]_D = -39° \pm 1°$ (c=1; dioxane); UV spectrum (ethanol): $\lambda_{max} = 315$ mμ (ε = 8800) and 269 mμ (ε = 3800); IR spectrum (methylene chloride): characteristic bands at 2.94; 5.56; 5.76 sh; 5.83; 5.89; 6.24 and 6.68μ.

The resulting compound can be further processed as follows:

(a) 0.424 ml (4.80 mmols) of phosphorus trichloride is added to a solution, cooled to −10° C., of 1.74 g (2.42 mmols) of 7β-(D(−)-α-tert.butoxycarbonylamino-α-phenylacetylamino)-3-carbomethoxymethylthio-3-cephem-4-carboxylic acid diphenylmethyl ester 1β-oxide in 8.5 ml of dimethylformamide and the mixture is stirred for 15 minutes at −10° C. and then poured onto ice. The product is extracted with ethyl acetate. The organic phase is washed with saturated aqueous sodium bicarbonate solution and saturated aqueous sodium chloride solution, dried over sodium sulphate and evaporated. Chromatography of the residue on 60 g of silica gel and elution with toluene/ethyl acetate, 4:1, gives 7β-(D(−)-α-tert.butoxycarbonylamino-α-phenyl-acetylamino)-3-carbomethoxymethylthio-3-cephem-4-carboxylic acid diphenylmethyl ester, which crystallises from methylene chloride/hexane; melting point 115°–117° C.; $[\alpha]_D = -40° \pm 1°$ (c=1.2; CHCl$_3$); UV spectrum (ethanol): $\lambda_{max} = 309$ mμ (ε = 7600) and 259 mμ (ε = 4100); IR spectrum (methylene chloride): characteristic bands at 2.92; 5.57; 5.77 sh; 5.82 sh; 5.87; 6.23 and 6.68μ.

(b) A solution of 1.0 g (1.42 mmols) of 7β-(D(−)-α-tert.butoxycarbonylamino-α-phenyl-acetylamino)-3-carbomethoxymethylthio-3-cephem-4-carboxylic acid diphenylmethyl ester in 5 ml of methylene chloride is stirred with 0.78 ml (7.1 mmols) of anisole and 4.35 ml (56.8 mmols) of trifluoroacetic acid for 30 minutes at 0° C. and the mixture is then treated with 100 ml of cold toluene and evaporated. The residue is digested with diethyl ether and the precipitate is filtered off and dried in a high vacuum. The resulting trifluoroacetate of 7β-(D(−)-α-phenylglycylamino)-3-carbomethoxymethylthio-3-cephem-4-carboxylic acid is suspended in 7 ml of water and brought into solution with 2 ml of methanol and the pH value of the solution is adjusted to 4.5 by adding a 10% strength methanolic triethylamine solution. The reaction mixture is left to stand at 0° C. for 24 hours and the fine crystalline precipitate is filtered off, washed with acetone and diethyl ether and dried in a high vacuum. 7β-(D(−)-α-Phenylglycylamino)-3-carbomethoxymethylthio-3-cephem-4-carboxylic acid is obtained in the zwitterionic form of melting point 158°–160° C.; $[\alpha]_D = +67° \pm 1°$ (c=0.719; 0.1 N hydrochloric acid); UV spectrum (ethanol): $\lambda_{max} = 286$ mμ (ε = 7600); IR spectrum (nujol): characteristic bands at 2.96; 3.06; 5.61 sh; 5.74; 5.86; 6.24 and 6.61μ.

EXAMPLE 8

A solution of 8.85 g of N-tert.-butoxycarbonylcysteamine in 50 ml of dimethylformamide is added, in the course of 1 hour, to a solution of 7.85 g (10 mmols) of 7β-(D-α-tert.butoxycarbonylamino-α-phenyl-acetylamino)-3-p-toluenesulphonyloxy-3-cephem-4-carboxylic acid diphenylmethyl ester 1β-oxide and 2.5 ml (15 mmols) of N,N-diethyl-N-isopropylamine in 50 ml of dimethylformamide. The reaction mixture is left to react for 5 hours, diluted with ethyl acetate and washed successively with 2 N hydrochloric acid, aqueous sodium bicarbonate solution and saturated aqueous sodium chloride solution and the organic phase is dried over sodium sulphate. The solvent is distilled off in vacuo and the residue is chromatographed on 200 g of silica gel. Using toluene and increasing amounts of ethyl acetate, amorphous 7β-(D-α-tert.butoxycarbonylamino-α-phenyl-acetylamino)-3-(2-tert.butoxycarbonylaminoethylthio)-3-cephem-4-carboxylic acid diphenylmethyl ester 1β-oxide is eluted. Thin layer chromatogram; Rf value: ∼0.30 (toluene/ethyl acetate, 1:1; silica gel) UV spectrum (ethanol): $\lambda_{max} = 319$ nm (ε = 6700); IR spectrum (methylene chloride): characteristic bands at 2.92; 5.57; 5.80 sh; 5.85; 5.89 sh; 6.24 and 6.65μ.

The resulting compound can be further processed as follows:

(a) A solution, cooled to −12° C., of 3.72 g (4.72 mmols) of 7β-(D-α-tert.-butoxycarbonylamino-α-phenyl-acetylamino)-3-(2-tert.butoxycarbonylaminoethylthio)-3-cephem-4-carboxylic acid diphenylmethyl ester in 20 ml of dimethylformamide is stirred with 0.82 ml (9.45 mmols) of phosphorus trichloride for 20 minutes under nitrogen and the mixture is then poured onto ice. The mixture is extracted with ethyl acetate. The organic phase is washed with saturated aqueous sodium bicarbonate solution and saturated aqueous sodium chloride solution, dried over sodium sulphate and evaporated in vacuo. The residue is chromatographed on 100 g of silica gel with toluene/ethyl acetate, 9:1, and this gives 7β-(D-α-tert.butoxycarbonylamino-α-phenyl-acetylamino)-3-(2-tert.butoxycarbonylaminoethylthio)-3-cephem-4-carboxylic acid diphenylmethyl ester, which according to thin layer chromatography is a single product. Thin layer chromatogram: Rf value: ∼0.53 (toluene/ethyl acetate, 1:1; silica gel) UV spectrum (ethanol): $\lambda_{max} = 315$ nm (ε = 7600); IR spectrum (methylene chloride): characteristic bands at 2.92; 5.58; 5.77 b; 6.24 and 6.66μ.

(b) A solution of 2.68 g (3.45 mmols) of 7β-(D-α-tert.-butoxycarbonylamino-α-phenyl-acetylamino)-3-(2-tert.butoxycarbonylaminoethylthio)-3-cephem-4-carboxylic acid diphenylmethyl ester in 12 ml of methylene chloride is stirred with 1.91 ml (5 equivalents) of anisole and 10.5 ml (40 equivalents) of trifluoroacetic acid for 30 minutes under nitrogen, in an ice bath, and, after adding 200 ml of cold toluene, the mixture is evaporated. The residue is digested with diethyl ether, filtered off and dried and gives the trifluoroacetate of 7β-(D(−)-α-phenylglycylamino)-3-(2-aminoethylthio)-3-cephem-4-carboxylic acid.

This is dissolved in 10 ml of methanol/water, 1:1, and the insoluble matter is filtered off. The pH value of the filtrate is adjusted to ∼5.0 by adding a 10% strength solution of triethylamine in methanol. Amorphous 7β-(D(−)-α-phenylglycylamino)-3-(2-aminoethylthio)-3-cephem-4-carboxylic acid is precipitated with acetone/ether, 1:1, and, according to thin layer chromatography, is a single product. Thin layer chromatogram, Rf value: ∼0.50 (silica gel; n-butanol/pyridine/acetic acid/water, 40:24:6:30); UV spectrum (ethanol): $\lambda_{max} = 283$ nm (ε = 6600); IR spectrum (nujol): characteristic bands at 2.90; 3,10; 5.60; 5.87 sh; 5.92 and 6.60μ.

EXAMPLE 9

16 g (138 mmols) of 5-mercapto-1-methyltetrazole and 23.7 ml (138 mmols) of N-ethyl-N,N-diisopropylamine are added to a solution of 58.4 g (98.2 mmols) of a mixture consisting of 7β-phenoxyacetylamino-3-methanesulphonyloxy-3-cephem-4-carboxylic acid diphenylmethyl ester and 7β-phenoxyacetylamino-3-methanesulphonyloxy-2-cephem-4-carboxylic acid diphenylmethyl ester in 224 ml of acetonitrile at 35° C. under nitrogen and the mixture is stirred at the same temperature for 17 hours. The solvent is evaporated off in vacuo, the residue is taken up in ethyl acetate and this solution is washed successively with water, aqueous sodium bicarbonate solution and saturated aqueous sodium chloride solution and the organic phase is dried over sodium sulphate and evaporated in vacuo. The residue is chromatographed on 1.1 kg of silica gel with toluene/ethyl acetate, 2:1. A mixture consisting of 7β-phenoxyacetylamino-3-(1-methyltetrazol-5-ylthio)-3-cephem-4-carboxylic acid diphenylmethyl ester of Rf value 0.24 (silica gel; toluene/ethyl acetate, 2:1) and 7β-phenoxyacetylamino-3-(1-methyltetrazol-5-ylthio)-2-cephem-4-carboxylic acid diphenylmethyl ester of Rf value 0.18 (silica gel; toluene/ethyl acetate, 2:1) is obtained.

The resulting mixture can be further processed as follows:

(a) 10.35 g (51.1 mmols) of m-chloroperbenzoic acid (85% strength) are added to a solution of 20.7 g (33.8 mmols) of a mixture consisting of 7β-phenoxyacetylamino-3-(1-methyl-5-tetrazolylthio)-3-cephem-4-carboxylic acid diphenylmethyl ester and 7β-phenoxyacetylamino-3-(1-methyl-5-tetrazolylthio)-2-cephem-4-carboxylic acid diphenylmethyl ester in 350 ml of chloroform at 0° C. and the mixture is stirred for 2 hours. Excess per acid is then destroyed by adding 85 ml of 0.1 N sodium thiosulphate. The reaction solution is extracted with aqueous sodium bicarbonate solution and saturated aqueous sodium chloride solution and the organic phase is dried over sodium sulphate and concentrated in vacuo. The residue is dried in a high vacuum and gives a mixture of the 1β-oxide and 1α-oxide of 7β-phenoxyacetylamino-3-(1-methyl-5-tetrazolylthio)-3-cephem-4-carboxylic acid diphenylmethyl ester; thin layer chromatogram: silica gel (toluene/ethyl acetate, 1:2), β-sulphoxide: Rf=0.26; α-sulphoxide: Rf=0.13. The two sulphoxides are chromatographed on 1 kg of silica gel with toluene/ethyl acetate, 1:2, and the pure β-sulphoxide of melting point 146° C. (from methyl acetate/hexane; IR spectrum (nujol): characteristic bands at 3.05; 5.58; 5.78; 5.83 and 5.97μ), and the pure α-sulphoxide of melting point 180° C. (decomposition; from methylene chloride/diethyl ether; IR spectrum (nujol): characteristic bands at 2.95; 5.53; 5.77 and 5.92μ) are obtained.

(b) A solution of 1 g (1.56 mmols) of 7β-phenoxyacetylamino-3-(1-methyl-5-tetrazolylthio)-3-cephem-4-carboxylic acid diphenylmethyl ester 1β-oxide in 5 ml of methylene chloride and 0.5 ml of dimethylformamide is cooled to 0° C., 0.695 ml (7.8 mmols) of phosphorus trichloride (distilled) is added under nitrogen and the mixture is stirred for 20 minutes. The reaction solution is washed with aqueous sodium bicarbonate solution until neutral and the organic phase is dried over sodium sulphate and concentrated in a rotary evaporator. The residue crystallises from methyl acetate/hexane and gives 7β-phenoxyacetylamino-3-(1-methyl-5-tetrazolylthio)-3-cephem-4-carboxylic acid diphenylmethyl ester of melting point 160° C. Thin layer chromatogram: silica gel (toluene/ethyl acetate, 1:2) Rf=0.53; IR spectrum (methylene chloride): characteristic bands at 2.92; 5.56; 5.75 and 5.87μ.

(c) A mixture of 7.1 g (11.6 mmols) of 7β-phenoxyacetylamino)-3-(1-methyl-5-tetrazolylthio)-3-cephem-4-carboxylic acid diphenylmethyl ester and 48 ml of trifluoroacetic acid is stirred for 35 minutes at 0° C. under nitrogen and then diluted with 100 ml of toluene and subsequently the solvent is stripped off in a high vacuum at a bath temperature of 35° C. The residue is partitioned between aqueous sodium bicarbonate solution and ethyl acetate. The organic phase is separated off and the aqueous phase is cooled to 0° C. and, after covering with ethyl acetate, the pH is adjusted to ~1.5 with phosphoric acid, whilst stirring vigorously. The organic phase is separated off, dried over sodium sulphate and evaporated in vacuo. The residue is chromatographed on 200 g of acid-washed silica gel with methylene chloride/ethyl acetate, 5:1, 7β-phenoxyacetylamino-3-(1-methyl-5-tetrazolylthio)-3-cephem-4-carboxylic acid being obtained in the amorphous form; thin layer chromatogram: silica gel (butanol/acetic acid/water, 75:7.5:21) Rf=0.31; IR spectrum (nujol): 3.00; 5.58; 5.90 and 6.25μ.

The starting material can be prepared as follows:

(d) A solution of 50.6 g (98 mmols) of 7β-phenoxyacetylamino-3-hydroxy-3-cephem-4-carboxylic acid diphenylmethyl ester in 500 ml of methylene chloride is cooled to −20° C. and, after adding 14 ml of methanesulphonyl chloride (142 mmols), 22.3 ml (142 mmols) of triethylamine are added slowly. After a reaction period of 1 hour at −15° C. to −20° C. under nitrogen, the solution is washed with water, aqueous sodium bicarbonate solution and saturated aqueous sodium chloride solution. The organic phase is dried over sodium sulphate, concentrated in a rotary evaporator and dried under a high vacuum. A mixture consisting of 7β-phenoxyacetylamino-3-methanesulphonyloxy-3-cephem-4-carboxylic acid diphenylmethyl ester and 7β-phenoxyacetylamino-3-methanesulphonyloxy-2-cephem-4-carboxylic acid diphenylmethyl ester is obtained; thin layer chromatogram (silica gel; toluene-/ethyl acetate, 2:1), 3-cephem derivative Rf=0.39; 2-cephem derivative Rf=0.32.

EXAMPLE 10

0.306 ml (1.27 mmols) of bis-trimethylsilylacetamide is added to a suspension of 200 mg (0.63 mmol) of 7β-amino-3-(1-methyl-5-tetrazolylthio)-3-cephem-4-carboxylic acid in 3.2 ml of methylene chloride and the mixture is stirred under nitrogen at room temperature for 40 minutes. The solution is cooled to 0° C., 224 mg (1.52 mmols) of tetrazol-1-ylacetyl chloride are added and the mixture is stirred for 1½ hours at 0° C. and extracted with aqueous sodium bicarbonate solution. The pH of the aqueous phase is adjusted to 1.5 and this phase is extracted with ethyl acetate. The organic phase is dried over sodium sulphate and evaporated in a rotary evaporator and gives 7β-[2-(tetrazol-1-yl)-acetylamino]-3-(1-methyl-5-tetrazolylthio)-3-cephem-4-carboxylic acid; thin layer chromatogram (silica gel; butanol/acetic acid/water, 75:7.5:21), Rf value 0.17; IR spectrum (nujol); characteristic bands at 3400, 1780, 1720 and 1690 cm$^{-1}$.

The starting material can be obtained as follows:

(a) 1 ml (7.9 mmols) of N,N-dimethylaniline and 0.268 ml (2.23 mmols) of dimethylchlorosilane are added to a suspension of 1 g (2.23 mmols) of 7β-phenoxyacetylamino-3-(1-methyl-5-tetrazolylthio)-3-cephem-4-carboxylic acid in 12.5 ml of methylene chloride, at room temperature and under nitrogen, and the mixture is stirred for 30 minutes at about 22° C. The solution is cooled to −18° C., 0.581 g (2.79 mmols) of phosphorus pentachloride is added and the mixture is stirred for 30 minutes at the same temperature. 3.52 ml of n-butanol and 0.35 ml of N,N-dimethylaniline are then added at −20° C. and the mixture is left to stand for 30 minutes at −10° C. The solution is warmed to 0° C., 0.2 ml of water is added and the pH is adjusted to 4 with triethylamine. The crystals which precipitate are filtered off, washed with acetone/water, 1:1, and dried in a high vacuum. The resulting 7β-amino-3-(1-methyl-5-tetrazolylthio)-3-cephem-4-carboxylic acid melts at 145° C. (decomposition); IR spectrum (nujol): characteristic bands at 3130 and 1800 cm$^{-1}$.

EXAMPLE 11

0.049 ml (0.388 mmol) of trimethylchlorosilane, 0.585 g (5.05 mmols) of 5-mercapto-1-methyltetrazole and 0.935 ml (5.43 mmols) of N-ethyl-N,N-diisopropylamine are added to a solution of 2.93 g (3.82 mmols) of 7β-(D-α-tert.butoxycarbonylamino-α-phenyl-acetylamino)-3-(p-toluenesulphonyloxy)-3-cephem-4-carboxylic acid diphenylmethyl ester in 11 ml of dimethylformamide. The red-brown solution is stirred for 16 hours at room temperature under nitrogen, diluted with ethyl acetate and purified by shaking with water, saturated aqueous sodium bicarbonate solution, 1 M sulphuric acid and saturated aqueous sodium chloride solution. The organic phase is dried over sodium sulphate and evaporated in vacuo. After drying the residue in a high vacuum, a mixture consisting of 7β-(D-α-tert.butoxycarbonylamino)-α-phenyl-acetylamino) 3-(1-methyl-5-tetrazolylthio)-3-cephem-4-carboxylic acid diphenylmethyl ester and the corresponding isomeric 2-cephem compound results and shows 2 spots in a thin layer chromatogram: silica gel (toluene/ethyl acetate, 2:1): Rf=0.13 (3-cephem compound); Rf=0.07 (2-cephem compound); IR spectrum of the crude product (CHCl$_3$): characteristic bands at 3400, 1780, 1730–1690 (broad), 1495 and 1370 cm$^{-1}$.

EXAMPLE 12

0.52 g (3.76 mmols) of the sodium salt of 5-mercapto-1-methyltetrazole is added to a solution of 2.0 g (2.89 mmols) of a mixture of isomers consisting of 7β-(D-α-tert.butoxycarbonylamino-α-phenyl-acetylamino)-3-methanesulphonyloxy-3-cephem-4-carboxylic acid diphenylmethyl ester and the corresponding 2-cephem derivative in 10 ml of dimethylformamide and the mixture is stirred for 17 hours at 33° C. under nitrogen. The reaction mixture is extracted with water and saturated aqueous sodium chloride solution. The organic phase is dried with sodium sulphate and evaporated in a rotary evaporator. The resulting mixture, consisting of 7β-(D-α-tert.butoxycarbonylamino-α-phenyl-acetylamino)-3-(1-methyl-4-tetrazolylthio)-3-cephem-4-carboxylic acid diphenylmethyl ester and the corresponding isomeric 2-cephem compound, has the same properties as indicated in Example 8.

The resulting mixture of isomers can be further processed as follows:

(a) A solution of 2.5 g of the mixture consisting of 7β-(D-α-tert.butoxycarbonylamino-α-phenyl-acetylamino)-3-(1-methyl-5-tetrazolylthio)-3-cephem-4-carboxylic acid diphenylmethyl ester and the corresponding isomeric 2-cephem compound in 65 ml of chloroform is cooled to 0° C., 0.86 g (4.24 mmols) of m-chloroperbenzoic acid (85% strength) is added whilst cooling well and the mixture is stirred for 1¾ hours. The excess per-acid is then destroyed by adding sodium thiosulphate. The reaction solution is extracted with aqueous sodium bicarbonate and saturated aqueous sodium chloride solution and the organic phase is dried over sodium sulphate and concentrated. The residue is crystallised from methylene chloride/diethyl ether and gives 7β-(D-α-tert.butoxycarbonylamino-α-phenylacetylamino)-3-(1-methyl-5-tetrazolylthio)-3-cephem-4-carboxylic acid diphenylmethyl ester 1β-oxide; thin layer chromatogram: silica gel (toluene/ethyl acetate, 1:1) Rf=0.23; IR spectrum (CHCl$_3$): characteristic bands at 3400, 1802, 1700, 1490 and 1380 cm$^{-1}$.

(b) A solution of 9.4 g (12.9 mmols) of 7β-(D-α-tert.butoxycarbonylamino-α-phenyl-acetylamino)-3-(1-methyl-5-tetrazolylthio)-3-cephem-4-carboxylic acid diphenylmethyl ester 1β-oxide in 70 ml of methylene chloride and 7 ml of dimethylformamide is cooled to 0° C., 5.62 ml (64.5 mmols) of phosphorus trichloride (distilled) are added and the mixture is stirred for 45 minutes. The reaction solution is extracted with aqueous sodium bicarbonate solution and saturated aqueous sodium chloride solution and the organic phase is dried over sodium sulphate and concentrated in a rotary evaporator. The residue crystallises from diethyl ether/hexane and gives 7β-(D-α-tert.butoxycarbonylamino-α-phenyl-acetylamino)-3-(1-methyl-5-tetrazolylthio)-3-cephem-4-carboxylic acid diphenylmethyl ester of melting point 170° C. Thin layer chromatogram: silica gel (toluene/ethyl acetate) Rf=0.35, IR spectrum (CH$_2$Cl$_2$): characteristic bands at 3420, 1800, 1710, 1500, and 1380 cm$^{-1}$.

(c) A mixture of 0.65 mg (0.91 mmol) of 7β-(D-α-tert.butoxycarbonylamino-α-phenyl-acetylamino)-3-(1-methyl-5-tetrazolylthio)-3-cephem-4-carboxylic acid diphenylmethyl ester and 8 ml of trifluoroacetic acid is stirred for 20 minutes, then diluted with toluene and subsequently substantially concentrated in a rotary evaporator. The residue is partitioned between water and ethyl acetate. The organic phase is separated off and the pH of the aqueous phase is adjusted to ~4.5 with triethylamine, 7β-(D(−)-α-phenylglycylamino)-3-(1-metyl-5-tetrazolylthio)-3-cephem-4-carboxylic acid crystallising out in the zwitterionic form. Melting point, 168° C. (decomposition); thin layer chromatogram: silica gel (butanol/acetic acid/water, 67:10:23), Rf=0.19; IR spectrum (nujol): characteristic bands at 1775 and 1690 cm$^{-1}$.

The starting material can be prepared as follows:

(d) A solution of 20.0 g (32,5 mmols) of 7β-(D-α-tert.butoxycarbonylamino-α-phenylacetylamino)-3-hydroxy-3-cephem-4-carboxylic acid diphenylmethyl ester in 400 ml of methylene chloride is cooled to −10° C., 3.75 g (48 mmols) of methanesulphonyl chloride and then 6.7 ml (48 mmols) of triethylamine are added and the mixture is stirred at the same temperature for ¼ hour. The reaction mixture is washed successively with dilute sulphuric acid, water, saturated aqueous sodium bicarbonate solution and saturated aqueous sodium chloride solution and the organic phase is dried over sodium sulphate and evaporated in vacuo. The residue is dried in a high vacuum and gives a mixture consisting of 7β-(D-α-tert.butoxycarbonylamino-α-phenylacetylamino)-3-methanesulphonyloxy-3-cephem-4-carboxylic acid diphenylmethyl ester and 7β-[D-α-tert.butoxycarbonylamino-α-phenylacetylamino]-3-methanesulphonyloxy-2-cephem-4-carboxylic acid diphenylmethyl ester of Rf value ~0.44 and 0.36 respectively (silica gel; toluene/ethyl acetate, 1:1).

EXAMPLE 13

A solution of 876 mg of N-ethyl-N,N-diisopropylamine in 10 ml of dimethylformamide and 2.5 g (33.75 mmols) of allylmercaptan are added to a solution of 3.2 g (4.5 mmols) of 7β-(D-α-tert.butoxycarbonylamino-α-phenyl-acetylamino)-3-methanesulphonyloxy-3-cephem-4-carboxylic acid diphenylmethyl ester 1-oxide in 20 ml of dimethylformamide and the mixture is stirred for 20 hours at room temperature under nitrogen. The reaction mixture is poured into water and extracted with ethyl acetate. The organic phase is washed successively with 20% strength phosphoric acid, saturated aqueous sodium bicarbonate solution and saturated aqueous sodium chloride solution. The ethyl acetate phase is dried over sodium sulphate and evaporated in vacuo. The residue is purified substantially by chromatography on 60 g of acid-washed silica gel with toluene/ethyl acetate, 80:20. The almost pure fractions are combined and recrystallised several times from ethyl acetate/hexane and give 7β-(D-α-tert.butoxycarbonylamino-α-phenylacetylamino)-3-allylthio-3-cephem-4-carboxylic acid diphenylmethyl ester 1-oxide of melting point 179°–181° C. (ethyl acetate/hexane): thin layer chromatogram Rf=0.225 (silica gel; toluene/ethyl acetate, 60:40); IR spectrum (methylene chloride): characteristic bands at 5.55 and 5.85μ.

(i) The same compound is obtained when 156 mg (0.2 mmol) of 7β-(D-α-tert.butoxycarbonylamino-α-phenyl-acetylamino)-3-p-toluenesulphonyloxy-3-cephem-4-carboxylic acid diphenylmethyl ester 1-oxide in 1 ml of dimethylformamide is stirred with a solution of allylmercaptan in dimethylformamide (3 ml, 0.5 molar, 1.5 mmols) in the presence of 39 mg (0.3 mmol) of N-ethyl-N,N-diisopropylamine for 20 hours at room temperature under nitrogen and the reaction mixture is worked up as above.

The product can be further processed as follows:

(a) 14 drops of phosphorus trichloride are added to a solution of 276 mg (0.4 mmol) of 7β-(D-α-tert.butoxycarbonylamino-α-phenyl-acetylamino)-3-allylthio-3-cephem-4-carboxylic acid diphenylmethyl ester 1-oxide in 2.8 ml of dimethylformamide and 11 ml of methylene chloride under nitrogen and the mixture is stirred for 1 hour at −20° C. The reaction mixture is diluted with water and ethyl acetate and the organic phase is washed successively with water, saturated aqueous sodium bicarbonate solution and saturated aqueous sodium chloride solution, dried over sodium sulphate and evaporated in vacuo. The residue is chromatographed on silica gel using toluene/ethyl acetate, 9:1, as the running agent. 7β-(D-α-Tert.butoxycarbonylamino-α-phenyl-acetylamino)-3-allylthio-3-cephem-4-carboxylic acid diphenylmethyl ester of melting point 153°–155° C. (from ethyl acetate/hexane) is eluted; thin layer chromatogram Rf=0.282 (silica gel; toluene/ethyl acetate, 80:20), $[\alpha]_D^{20} = -32° \pm 1°$ (c=0.96; chloroform); IR spectrum (methylene chloride): characteristic bands at 2.95; 5.60 and 5.90μ.

(b) 3 ml of trifluoroacetic acid, which has been precooled to 0° C., are added to 150 mg (0.224 mmol) of 7β-(D-α-tert.butoxycarbonylamino-α-phenyl-acetylamino)-3-allylthio-3-cephem-4-carboxylic acid diphenylmethyl ester at 0° C. under nitrogen. The reaction mixture is stirred for 15 minutes at 0° C. and added to 18 ml of a mixture of pentane/diethyl ether, 3:1, which has been cooled to 0° C. The precipitate which is deposited is centrifuged off and washed twice more with pentane/diethyl ether, 3:1. The crude product is dissolved in water, treated with active charcoal from the end of a spatula and filtered off through Hyflo. The solution is freed from solvent by freeze-drying and gives the trifluoroacetate of 7β-(D-α-phenylglycylamino)-3-allylthio-3-cephem-4-carboxylic acid which decomposes above 145° C.: IR spectrum (nujol): characteristic bands at 5.64 and 5.93μ.

The starting material can be obtained as follows:

(c) A solution of 1.7 g of m-chloroperbenzoic acid in 15 ml of ethyl acetate is added to a solution of 3.8 g of a mixture of 7β-(D-α-tert.butoxycarbonylamino-α-phenyl-acetylamino)-3-methanesulphonyloxy-3-cephem-4-carboxylic acid diphenylmethyl ester and 7β-(D-α-tert.butoxycarbonylamino-α-phenyl-acetylamino)-3-methanesulphonyloxy-2-cephem-4-carboxylic acid diphenylmethyl ester in 25 ml of ethyl acetate at 0° C. and the mixture is stirred for 30 minutes at 0° C. 50 ml of 5% strength aqueous sodium bisulphite solution are added to the reaction mixture and the mixture is stirred for 2 minutes. The organic phase is separated off and washed with saturated aqueous sodium bicarbonate solution and water, dried over sodium sulphate and evaporated in vacuo. The crude product is recrystallised from methylene chloride/pentane and gives 7β-(D-α-tert.butoxycarbonylamino-α-phenyl-acetylamino)-3-methanesulphonyloxy-3-cephem-4-carboxylic acid diphenylmethyl ester 1-oxide in the form of brown crystals.

EXAMPLE 14

A solution of 53 mg of 3-methylthio-7β-phenoxyacetylamino-3-cephem-4-carboxylic acid p-nitrobenzyl ester in 5 ml of a warm 2:1 mixture of tetrahydrofurane and methanol is added to a mixture, which has been prehydrogenated for 30 minutes in a hydrogenation apparatus, of 51 mg of 5% strength palladium-on-charcoal catalyst in 1 ml of tetrahydrofurane/methanol, 1:1, and the mixture is hydrogenated for 4 hours whilst stirring. The solution is filtered, the catalyst is washed with 4 times 6 ml of ethyl acetate and the filtrate and the washing liquid are evaporated in vacuo. The residue is dissolved in methylene chloride and extracted with dilute aqueous sodium bicarbonate solution. The aqueous phase is extracted by shaking three times with methylene chloride and the yellow oil of the intermediate layer is discarded. The aqueous bicarbonate solution is cooled in an ice bath, covered with ethyl acetate and acidified to about pH 2 with 2 N hydrochloric acid. The organic phase is separated off, the yellow oil of the intermediate layer is again discarded and the aqueous phase is extracted with methylene chloride. The combined ethyl acetate and methylene chloride phases are washed with water, dried over sodium sulphate and evaporated in vacuo. The residue is recrystallised from methylene chloride/diethyl ether and gives 3-methylthio-7β-phenoxyacetylamino-3-cephem-4-carboxylic acid of melting point 122°–125° C.; IR spectrum (KBr): characteristic bands at 5.64; 5.95; 6.25; 6.55; 6.70; 8.20; 8.58; 8.94 and 13.25μ.

The starting material can be obtained as follows:

(a) A solution of 50 mg (0.1 mmol) of 3-methoxy-7β-phenoxyacetylamino-3-cephem-4-carboxylic acid p-nitrobenzyl ester in 4 ml of dimethylformamide is cooled to about −58° C. in a dimethoxyethane/dry ice bath and a solution of 13 mg of potassium tert.butylate and 4 drops of methylmercaptan in 4 ml of dimethylformamide is added dropwise under a nitrogen atmosphere. The reaction mixture is stirred for a further 5 minutes at −58° C. and then shaken with 50 ml of ethyl acetate and 50 ml of dilute aqueous sodium bicarbonate solution. The organic phase is washed with water and saturated aqueous sodium chloride solution, dried over sodium sulphate and evaporated in vacuo. The residue, consisting of the two epimeric addition products 3β-methoxy-3α-methylthio-7β-phenoxyacetylamino-cepham-4β-carboxylic acid p-nitrobenzyl ester and 3β-methoxy-3α-methylthio-7β-phenoxyacetylamino-cepham-4α-carboxylic acid p-nitrobenzyl ester, is dissolved in 1 ml of benzene/trifluoroacetic acid, 3:1, and the solution is left to stand for about 90 hours at 5° C. The solution is diluted with ethyl acetate, washed successively with aqueous sodium bicarbonate solution, water and saturated aqueous sodium chloride solution, dried over sodium sulphate and evaporated in vacuo. The residue is recrystallised from chloroform/diethyl ether and gives analytically pure 3-methylthio-7β-phenoxyacetylamino-3-cephem-4-carboxylic acid p-nitrobenzyl ester of melting point 188°–189° C.

IR spectrum (in methylene chloride): characteristic bands at 2.91; 5.57; 5.87; 6.22; 6.55; 7.40; 8.21; 8.58; 8.94 and 11.71μ.

The two epimeric addition products formed as intermediate products can also be obtained as follows:

(ai) A solution of 50 mg (0.1 mmol) of 3-methoxy-7β-phenoxyacetylamino-2-cephem-4α-carboxylic acid p-nitrobenzyl ester in 2 ml of dimethylformamide is cooled to about −58° C. in a dimethoxyethane/dry ice bath and a solution of about 0.5 ml of methylmercaptan and 4 mg of potassium tert.butylate in 2 ml of dimethylformamide is added rapidly under a nitrogen atmosphere whilst stirring. The reaction mixture is stirred for a further 30 minutes at −58° C. and then poured, whilst still cold, into a mixture of 5% strength aqueous sodium bicarbonate solution and ethyl acetate and the mixture is shaken thoroughly. The organic phase is separated off, washed successively with water, dilute aqueous citric acid, water and aqueous sodium chloride solution, dried over sodium sulphate and evaporated in vacuo. According to thin layer chromatography (silica gel, toluene/ethyl acetate, 1:1), NMR spectra and IR spectra, the residue contains the two isomeric addition products 3β-methoxy-3α-methylthio-7β-phenoxyacetylamino-cepham-4β-carboxylic acid p-nitrobenzyl ester and 3β-methoxy-3α-methylthio-7β-phenoxyacetylamino-cepham-4α-carboxylic acid p-nitrobenzyl ester.

The addition of methylmercaptan at the $C_3$–$C_4$ double bond can also be carried out, under otherwise identical conditions, in tetrahydrofurane instead of in dimethylformamide.

The elimination of methanol, described under (a), can also be carried out, under otherwise identical conditions, in chloroform instead of in benzene.

A crystalline intermediate product can be obtained as follows:

(aii) A solution of 5 g (10 mmols) of a mixture consisting of 3-methoxy-7β-phenoxyacetylamino-3-cephem-4-carboxylic acid p-nitrobenzyl ester and 3-methoxy-7β-phenoxyacetylamino-2-cephem-4α-carboxylic acid p-nitrobenzyl ester in a ratio of about 1:1 in 75 ml of tetrahydrofurane (peroxide-free) is cooled to about −78° C. in an isopropanol/dry ice bath and 20 ml of a tetrahydrofurane solution containing 5 ml of methylmercaptan and 1 ml of n-butyl-lithium are added dropwise under a nitrogen atmosphere, whilst stirring. The reaction mixture is stirred for a further 1 hour at −72° C. internal temperature and a solution of 5 ml of glacial acetic acid in 15 ml of tetrahydrofurane is then added dropwise, again at −78° C., at such a rate that the internal temperature does not rise above −72° C. The reaction mixture is poured into water and extracted with ethyl acetate. The organic phase is washed with saturated aqueous sodium chloride solution, dried over sodium sulphate and evaporated in vacuo. The residue, consisting of the two epimeric addition products 3β-methoxy-3α-methylthio-7β-phenoxyacetylamino-cepham-4β-carboxylic acid p-nitrobenzyl ester and 3β-methoxy-3α-methylthio-7β-phenoxyacetylamino-cepham-4αcarboxylic acid p-nitrobenzyl ester is recrystallised from toluene/hexane and gives pure 3β-methoxy-3α-methylthio-7β-phenoxyacetylamino-cepham-4β-carboxylic acid p-nitrobenzyl ester of melting point 132°–134° C.; $[\alpha]_D^{20} = +185° \pm 1°$ (c=1, chloroform); thin layer chromatogram, silica gel (toluene/ethyl acetate, 1:1): Rf=0.64; UV spectrum (ethanol); $\lambda_{max}$ 268 mμ (ε=11600) and 265 mμ (ε=11500); IR spectrum (methylene chloride): characteristic bands at 2.94; 3.41; 5.61; 5.70; 5.90; 6.24; 6.55; 6.69; 7.42; 8.55 and 9.28μ.

Pure 3β-methoxy-3α-methylthio-7β-phenoxyacetylamino-cepham-4β-carboxylic acid p-nitrobenzyl ester can also be further processed as follows:

(b) A solution of 4.5 g (8.2 mmols) of 3β-methoxy-3α-methylthio-7β-phenoxyacetylamino-cepham-4β-carboxylic acid p-nitrobenzyl ester in 100 ml of a 9:1 mixture of dry benzene and trifluoroacetic acid is stirred under nitrogen for 15 to 18 hours at 40° C. The reaction mixture is washed with water and saturated aqueous sodium chloride solution, dried over sodium sulphate, filtered and evaporated. The residue is recrystallised from methylene chloride/diethyl ether and gives 3-methylthio-7β-phenoxyacetylamino-3-cephem-4-carboxylic acid p-nitrobenzyl ester of melting point 190°–191° C.; $[\alpha]_D^{20} = +44° \pm 1°$ (c=1, chloroform); UV spectrum (acetonitrile): $\lambda_{max}$=268 nm (ε=13400), 275 nm (ε=12500) and 314 nm (ε=10200); IR spectrum (methylene chloride): characteristic bands at 2.92; 5.57; 5.86; 6.23 6.55; 7.40; 8.20; 8.60; 8.95; 9.25; 9.40; 9.95 and 11.70μ; thin layer chromatogram, silica gel: (toluene/ethyl acetate, 1:1): Rf=0.70.

The analytically pure 3-methylthio-7β-phenoxyacetylamino-3-cephem-4-carboxylic acid p-nitrobenzyl ester can also be further processed as follows:

(c) A solution of 2.6 g (5 mmols) of 3-methylthio-7β-phenoxyacetylamino-3-cephem-4-carboxylic acid p-nitrobenzyl ester in 75 ml of a warm 5:1 mixture of tetrahydrofurane and ethanol is added to a mixture, which has been pre-hydrogenated for 30 minutes in a hydrogenation apparatus, of 2.5 g of 5% strength palladium-on-charcoal catalyst in 10 ml of tetrahydrofurane/ethanol, 1:1, and the mixture is hydrogenated for 4 hours whilst stirring. The solution is filtered, the catalyst is washed with ethyl acetate and the filtrate and washing liquor are combined, washed successively with an aqueous citric acid solution and water and then extracted several times with 5% strength aqueous sodium bicarbonate solution. The bicarbonate extracts are combined, washed with methylene chloride, cooled to 0° C., slowly acidified with 2 N hydrochloric acid and extracted with ethyl acetate. The organic phase is washed with water and saturated aqueous sodium chloride solution, dried over sodium sulphate, filtered and evaporated. The residue is recrystallised from methylene chloride/diethyl ether and gives 3-methylthio-7β-phenoxyacetylamino-3-cephem-4-carboxylic acid of melting point 164°–166° C. (decomposition); $[\alpha]_D^{20} = +109° \pm 1°$ (c=1; dioxane); thin layer chromatogram: silica gel (toluene/ethyl acetate/water, 5:5:1) Rf=0.16; UV spectrum (ethanol); $\lambda_{max}$=269 nm (ε=4800), 276 nm (ε=5200) and 308 nm (ε=7700); IR spectrum (KBr): characteristic bands at 3.00; 3.40; 5.63; 5.91; 6.25; 6.53; 6.68; 8.20; 8.55; 8.90; 9.25; 9.43; 13.20 and 14.45μ.

EXAMPLE 15

A suspension of 3.80 g (10 mmols) of 7β-phenoxyacetamido-3-methylthio-ceph-3-em-4-carboxylic acid in 38 ml of absolute methylene chloride is stirred with 4.45 ml of dimethylaniline and 1.50 ml of dimethyldichlorosilane for 30 minutes at room temperature. The reaction mixture is cooled to −20° C., 2.60 g of phosphorus pentachloride are added, the mixture is stirred for 30 minutes at −20° C. and is then added dropwise to a mixture, cooled to −20° C., of 15.5 ml of n-butanol and 1.47 ml of dimethylaniline. The temperature is allowed to rise to −10° C. and 15.5 ml of dioxane and 0.53 ml of water are added. When crystallisation starts, the pH value is adjusted to 4.1 with tributylamine and crystallisation is brought to completion by stirring for 2 hours at 0°–5° C. The precipitate is filtered off, washed with 10 ml of dioxane and 5 ml of methylene chloride and dried in a high vacuum. 7β-Amino-3-methylthio-ceph-3-em-4-carboxylic acid of melting point 205° C. (decomposition) is obtained; UV spectrum (0.1 N NaHCO₃): $\lambda_{max}$=293 (ε=7600); IR spectrum (nujol): characteristic bands at 3.15, 5.55 6.17 and 6.53μ.

EXAMPLE 16

1.68 g (15 mmols) of (D)-mandelic anhydride are added in the course of 15 minutes to a mixture, cooled to 0° C., of 1.23 g (5.0 mmols) of 7β-amino-3-methylthio-ceph-3-em-4-carboxylic acid and 630 mg (7.5 mmols) of sodium bicarbonate in 50 ml of acetone/water, 1:1, and the mixture is then stirred for a further 30 minutes at pH 7.5. The reaction mixture is concentrated in vacuo and extracted with ethyl acetate. The aqueous phase is acidified to pH 2 and extracted with ethyl acetate and the organic extract is extracted by shaking with saturated aqueous sodium chloride solution, dried over sodium sulphate and evaporated. The crude product is chromatographed on 50 g of silica gel, which had been deactivated by adding 5% of water. Using toluene/ethyl acetate, 1:1, 7β-(D-mandeloylamino)-3-methylthio-3-cephem-4-carboxylic acid is eluted; this is a single compound according to thin layer chromatography and is reprecipitated from methylene chloride/ethyl acetate with diethyl ether/hexane; thin layer chromatogram (silica gel: ethyl acetate/pyridine/acetic acid/water, 61:21:6:11) Rf=0.37; UV spectrum (ethanol) $\lambda_{max}$=309 mμ (ε=8000); IR spectrum (nujol); characteristic bands at 2.98; 5.63; 5.93 and 6.55μ.

EXAMPLE 17

17 ml of trifluoroacetic acid are added to a solution of 855 mg (1.37 mmols) of a mixture of 3β-methoxy-3α-benzylthio-7β-phenoxyacetylamino-4β-carboxylic acid p-nitrobenzyl ester and 3β-methoxy-3α-benzylthio-7β-phenoxyacetylamino-4α-carboxylic acid p-nitrobenzyl ester, which is epimeric thereto, in a ratio of about 8:2 in 17 ml of benzene and the mixture is left to stand for 16 hours at room temperature. The solvent is evaporated off in vacuo and the residue is evaporated a further three times together with toluene in order to remove trifluoroacetic acid. The residue is recrystallised from ethyl acetate and hexane and gives 3-benzylthio-7β-phenoxyacetylamino-3-cephem-4-carboxylic acid p-nitrobenzyl ester of melting point 174°–175° C.; $[\alpha]_D^{20} = 16° \pm 1°$ (c=0.725, chloroform); ultraviolet spectrum (ethanol); $\lambda_{max}$=268 nm (ε=9600) and 318 nm (ε=6500); IR spectrum (methylene chloride): characteristic bands at 2.95; 5.61 and 5.91μ.

The resulting product can be further processed as follows:

(a) 425 mg of activated zinc powder are added to a solution of 425 mg (0.72 mmol) of 3-benzylthio-7β-phenoxyacetylamino-3-cephem-4-carboxylic acid p-nitrobenzyl ester in 40 ml of glacial acetic acid and the mixture is stirred vigorously for 2 hours at room temperature and under nitrogen. The solvent is removed in vacuo and the residue is stirred with ethyl acetate and filtered. The solution is extracted with aqueous sodium bicarbonate solution and water. The combined aqueous phases are washed with ethyl acetate, acidified with hydrochloric acid and extracted with ethyl acetate. The organic phase is dried over sodium sulphate, filtered and evaporated in vacuo. The residue is chromatographed on silica gel with toluene containing 10% of acetone and gives 3-benzylthio-7β-phenoxyacetylamino-3-cephem-4-carboxylic acid; $[\alpha]_D^{20} = +19° \pm 1°$ (c=0.8; chloroform); IR spectrum (methylene chloride): characteristic bands at 5.61 and 5.90μ.

The starting material can be obtained as follows:

(b) A solution of 1 g (2 mmols) of 3-methoxy-7β-phenoxyacetylamino-4-carboxylic acid p-nitrobenzyl ester in 100 ml of tetrahydrofurane is cooled, under nitrogen, to −78° C., treated successively with 0.3 ml (2.56 mmols) of benzylmercaptan and 0.5 ml of a 20% strength solution of n-butyl-lithium in hexane and the mixture is stirred for 90 minutes at the same temperature. After the dropwise addition of 2 ml of a 50% strength solution of acetic acid in tetrahydrofurane, the solution is warmed to room temperature and the major part of the tetrahydrofurane is distilled off in vacuo and replaced by ethyl acetate. The organic phase is washed successively with water, aqueous sodium bicarbonate solution and saturated aqueous sodium chloride solution, dried over sodium sulphate and evaporated in vacuo. The residue is chromatographed on silica gel, excess benzylmercaptan first being eluted with toluene and a mixture consisting of 3β-methoxy-3α-benzylthio-7β-phenoxyacetylamino-4β-carboxylic acid p-nitrobenzyl ester and 3β-methoxy-3α-benzylthio-7β-phenoxyacetylamino-4α-carboxylic acid p-nitrobenzyl ester, which is epimeric thereto, being eluted in a ratio of about 8:2 with toluene/ethyl acetate, 7:3. This mixture of epimers is sufficiently pure for further processing. Pure 3β-methoxy-3α-benzylthio-7β-phenoxyacetylamino-4β-carboxylic acid p-nitrobenzyl ester of melting point 113°–115° C. can be obtained therefrom by recrystallisation from benzene; $[\alpha]_D^{20} = +217 \pm 1°$ (c=0.778; chloroform); UV spectrum (ethanol): $\lambda_{max}$=264 mμ (ε=11,300) and 267 mμ (ε=11400); IR spectrum (methylene chloride): characteristic bands at 2.95; 5.65; 5.74 and 5.95μ.

EXAMPLE 18

2.04 g (10 mmols) of 85 percent strength m-chloroperbenzoic acid are added to a suspension of 6.62 g (10 mmols) of 7β-(D(−)-α-tert.butoxycarbonylamino-α-phenyl-acetylamino)-3-methylthio-4-carboxylic acid diphenylmethyl ester 1-oxide in 200 ml of methylene chloride and the mixture is stirred for 1 hour at room temperature. The reaction mixture is washed with saturated aqueous sodium chloride solution, dried over sodium sulphate and evaporated in vacuo. The crude product is chromatographed on 150 g of silica gel. Ethyl acetate elutes 7β-(D(−)-α-tert.butoxycarbonylamino-α-phenyl-acetylamino)-3-methylsulphinyl-3-cephem-4-carboxylic acid diphenylmethyl ester 1-oxide, which is crystallised from methylene chloride/petroleum ether. Melting point 160°–161° C.: $[\alpha]_D = -156 \pm 1°$ (c=0.885; CHCl$_3$), UV spectrum (ethanol): $\lambda_{max}=282$ mμ (ε=6900); IR spectrum (nujol): characteristic bands at 2.96; 3.04; 5.55; 5.82; 5.91; 6.02; 6.22; 6.58 and 6.67μ.

Analogously to Example 4(a), the resulting compound can be converted into 7β-(D-α-tert.butoxycarbonylamino-α-phenylacetylamino)-3-methylthio-3-cephem-4-carboxylic acid diphenylmethyl ester using twice the amount of phosphorus trichloride.

EXAMPLE 19

A suspension of 1.70 g of 7β-[D(−)-α-aminophenylacetamido]-3-methylthio-ceph-3-em-4-carboxylic acid in a mixture of 20 ml of tetrahydrofurane and 20 ml of methylene chloride is cooled to 0° C. and 1.90 ml of triethylamine are added whilst stirring and excluding atmospheric humidity, a clear solution being formed. This mixture is then cooled to −10° C. and a solution of 0.80 g of 3,5-dioxo-2,3,4,5-tetrahydro-1,2,4-triazine-6-carboxylic acid chloride in a mixture of 6 ml of N,N-dimethylformamide and 6 ml of tetrahydrofurane is added dropwise at −10° C. in the course of 20 minutes, whilst stirring and cooling. The suspension is then diluted with 10 ml of N,N-dimethylformamide and stirred for 30 minutes at 0° C. and for 1 hour at room temperature. The low-boiling solvent is then removed in a rotary evaporator at 40° C. and the product is precipitated from the residual N,N-dimethylformamide solution by adding ether, filtered off and washed with ether. The material on the filter is dissolved in a phosphate buffer solution of pH 7.5 and the solution is extracted twice with ethyl acetate. The aqueous phase is separated off, covered with ethyl acetate, acidified (pH 2.5) at 10° C., whilst stirring and cooling in an ice bath, by adding 20% strength phosphoric acid and extracted three times with ethyl acetate. The ethyl acetate extracts are combined, washed twice with sodium chloride solution, dried over sodium sulphate and freed from solvent at 45° C. in a rotary evaporator. The residual product is purified by crystallisation from ethyl acetate. 7β-[D(−)-α-(3,5-dioxo-2,3,4,5-tetrahydro-1,2,4-triazine-6-carboxamido)-phenylacetamido]-3-methylthio-ceph-3-em-4-carboxylic acid melts at 208°–212° C. with decomposition. Thin layer chromatogram on silica gel: Rf (butanol/acetic acid/water, 67:10:23)=0.32; Rf (butanol/pyridine/acetic acid/water: 38:24:8:30)=0.50; Rf (butanol/pyridine/acetic acid/water, 42:24:4:30)=0.41; $[\alpha]_D^{20} = +79° \pm 1°$ (c=1.065; in dimethylsulphoxide).

EXAMPLE 20

An excess of methyl iodide and N-ethyl-N,N-diisopropylamine is added to a solution of 60 mg of 7β-phenoxyacetylamino-3-mercapto-3-cephem-4-carboxylic acid p-nitrobenzyl ester in 1 ml of tetrahydrofurane and the mixture is stirred for 10 minutes and evaporated in vacuo. The residue is chromatographed on silica gel with toluene and increasing amounts of ethyl acetate and gives a mixture consisting of 7β-phenoxyacetylamino-3-methylthio-3-cephem-4-carboxylic acid p-nitrobenzyl ester and the corresponding 2-cephem derivative. Thin layer chromatogram: double spot at Rf=0.6 (silica gel; toluene/ethyl acetate, 1:1); IR spectrum (methylene chloride): characteristic bands at 2.95; 5.60; 5.70; 5.90; 6.25; 6.58; 6.70; 6.97; 7.43; 8.20; 8.60; 9.00; 9.75 and 9.95μ.

The starting material can be prepared as follows:

(a) 300 mg of sodium bisulphide, 50 mg of benzyltrimethylammonium chloride and 40 mg of 1,5-diazabicyclo[5.4.0]undec-5-ene are added to a solution of 52 mg of a mixture consisting of 7β-phenoxyacetylamino-3-methoxy-3-cephem-4-carboxylic acid p-nitrobenzyl ester and 7β-phenoxyacetylamino-3-methoxy-2-cephem-4-carboxylic acid p-nitrobenzyl ester in 5 ml of dimethylformamide at −5° C. and the mixture is stirred for 5 minutes. The reaction mixture is diluted with ethyl acetate, washed with aqueous citric acid solution, water and saturated aqueous sodium chloride solution, dried over sodium sulphate and evaporated in vacuo. The residue is purified by preparative silica gel layer chromatography using toluene/ethyl acetate as the running agent and gives 7β-phenoxyacetylamino-3-mercapto-3-cephem-4-carboxylic acid p-nitrobenzyl ester; thin layer chromatogram: Rf=0.08 (silica gel; toluene/ethyl acetate, 1:1).

EXAMPLE 21

The following end products can be prepared analogously to the above examples, starting from corresponding and suitable 3-p-toluenesulphonylthio- or 3-methoxy-cephem-4-carboxylic acid esters: 7β-cyanoacetylamino-3-methylthio-3-cephem-4-carboxylic acid; 7β-[D-α-(p-hydroxyphenyl)-glycylamino]-3-methylthio-3-cephem-4-carboxylic acid, 7β-(2-thienylacetylamino)-3-methylthio-3-cephem-4-carboxylic acid; 7β-[2-(5-aminomethyl-thien-2-yl)-acetylamino]-3-methylthio-3-cephem-4-carboxylic acid; 7β-(tetrazol-1-ylacetylamino)-3-methylthio-3-cephem-4-carboxylic acid; 7β-[D-α-(1,4-cyclohexadienyl)-glycylamino]-3-methylthio-3-cephem-4-carboxylic acid and 7β-[D-α-(1-cyclohexenyl)-glycylamino)-3-methylthio-3-cephem-4-carboxylic acid.

EXAMPLE 22

The following end products can be prepared analogously to the above examples, starting from corresponding and suitable 3-p-toluenesulphonylthio- or 3-methoxy-cephem-4-carboxylic acid esters: 7β-[2-(2-furyl)-2-syn-methoxyiminoacetylamino]-3-methylthio-3-cephem-4-carboxylic acid; 7β-(D-α-hydroxyphenylacetylamino)-3-(2-carbomethoxymethylthio)-3-cephem-4-carboxylic acid; 7β-[2-(5-aminomethylthien-2-yl)-acetylamino]-3-(2-carbomethoxymethylthio)-3-cephem-4-carboxylic acid; 7β-cyanoacetylamino-3-(1-methyltetrazol-5-ylthio)-3-cephem-4-carboxylic acid; 7β-[2-(5-aminomethylthien-2-yl)-acetylamino]-3-(1-methyltetrazol-5-ylthio)-3-cephem-4-carboxylic acid;

7β-[2-(2-furyl)-2-syn-methoxyimino-acetylamino]-3-(1-methyltetrazol-5-ylthio)-3-cephem-4-carboxylic acid.

EXAMPLE 23

Dry ampoules or phials containing 0.5 g of the sodium salt of 7β-phenylacetylamino-3-phenylthio-3-cephem-4-carboxylic acid are manufactured as follows:

Composition (for 1 ampoule or phial)

Sodium salt of 7β-phenylacetylamino-3-phenylthio-3-cephem-4-carboxylic acid: 0.5 g
Mannitol: 0.05 g A sterile aqueous solution of the sodium salt of 7β-phenylacetylamino-3-phenylthio-3-cephem-4-carboxylic acid and mannitol is subjected to freeze-drying under aseptic conditions in 5 ml ampoules or 5 ml phials and the ampoules or phials are sealed and tested.

EXAMPLE 24

Dry ampoules or phials containing 0.5 g of the sodium salt of 7β-(D-mandeloylamino)-3-methylthio-3-cephem-4-carboxylic acid are manufactured as follows:

Composition (for 1 ampoule or phial)

Sodium salt of 7β-(D-mandeloylamino)-3-methylthio-3-cephem-4-carboxylic acid: 0.5 g
Mannitol: 0.05 g A sterile aqueous solution of the sodium salt of 7β-(D-mandeloylamino)-3-methylthio-3-cephem-4-carboxylic acid and mannitol is subjected to freeze-drying under aseptic conditions in 5 ml ampoules or 5 ml phials and the ampoules or phials are sealed and tested.

EXAMPLE 25

Capsules containing 0.25 g of the inner salt of 7β-(D-α-phenyl-glycylamino)-3-methylthio-3-cephem-4-carboxylic acid are manufactured as follows:

Composition (for 4000 capsules):

Inner salt of 7β-(D-α-phenyl-glycylamino)-3-methylthio-3-cephem-4-carboxylic acid: 250,000 g
Maize starch: 50,000 g
Polyvinylpyrrolidone: 15,000 g
Magnesium stearate: 5,000 g
Ethanol: q.s.

The inner salt of 7β-(D-α-phenyl-glycylamino)-3-methylthio-3-cephem-4-carboxylic acid and maize starch are mixed and moistened with a solution of polyvinylpyrrolidone in 50 g of ethanol. The moist composition is pressed through a sieve with a mesh width of 3 mm and dried at 45° C. The dry granules are forced through a sieve with a mesh width of 1 mm and are mixed with 5 g of magnesium stearate. The mixture is filled, in portions of 0.320 g, into size 0 push-fit capsules.

We claim:
1. A compound of the formula

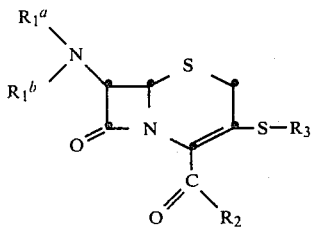

(IA)

wherein $R_1{}^a$ denotes hydrogen, cyanoacetyl, or an acyl group of the formula

(B), wherein X denotes oxygen or sulfur and, if m represents zero or 1, $R_a$ denotes phenyl, hydroxyphenyl, hydroxyphenyl protected by tert.-butoxycarbonyl or 2,2,2-trichloroethoxycarbonyl, hydroxy-chlorophenyl, hydroxy-chlorophenyl protected by tert.-butoxycarbonyl or 2,2,2-trichloroethoxycarbonyl, thienyl, 5-aminomethyl-2-thienyl, pyridyl, amino pyridinium, furyl, isothiazolyl, tetrazolyl, 1-cyclohexenyl, or 1,4-cyclohexadienyl, and $R_b$ and $R_c$ each represents hydrogen, or, if m represents zero, $R_a$ denotes phenyl, hydroxyphenyl, hydroxyphenyl protected by tert.-butoxycarbonyl or 2,2,2-trichloroethoxycarbonyl, hydroxychlorophenyl, hydroxy-chlorophenyl protected by tert.-butoxycarbonyl or 2,2,2-trichloroethoxycarbonyl, thienyl, 5-aminoethyl-2-thienyl, pyridyl, aminopyridinium, furyl, isothiazolyl, tetrazolyl, 1-cyclohexenyl or 1,4-cyclohexadienyl, $R_b$ denotes amino, tert.-butoxycarbonylamino, 2-halogeno-lower-alkoxycarbonylamino, lower alkoxyphenyl-lower alkoxycarbonylamino, phenyl-lower alkoxycarbonylamino, dihydroxy-triazinylcarbonylamino, 3-guanylureido, sulfoamino, tritylamino, 2-nitrophenylthioamino, 4-methylphenylsulfonylamino, 1-lower alkoxycarbonyl-2-propylideneamino, carboxyl, phenyl-lower alkoxycarbonyl, sulfo, hydroxyl, tert.-butoxycarbonyloxy, 2-halogen-lower alkoxycarbonyloxy, formyloxy, o-lower alkylphosphono, o,o'-di-lower alkylphosphono, 5-amino-5-carboxy-valeryl, 5-amino-5-carboxy-valeryl, wherein 5-amino is protected by lower alkanoyl, halogeno-lower alkanoyl, benzoyl or phthaloyl and 5-carboxy is protected by phenyl-lower alkoxycarbonyl, or 5-amino-5-carboxy-valeryl, wherein 5-carboxy is protected by phenyl-lower alkoxy and $R_c$ denotes hydrogen, or, if m represents zero, $R_a$ denotes phenyl, 2-thienyl, or 2-furyl and $R_b$ and $R_c$ conjointly denote lower alkoxyimino, cycloalkoxyimino or phenylalkoxyimino in the synconfiguration $R_1{}^b$ denotes hydrogen, $R_2$ represents hydroxyl, lower alkoxy, tert.-butoxy, 2-halogeno-lower alkoxy, diphenylmethoxy, lower alkoxy-diphenylmethoxy, or tri-lower alkylsilyloxy, and $R_3$ represents lower alkyl, amino lower alkyl, tert.-amino-lower alkyl, wherein the tert.-amino group is separated from the sulfur atom by at least two carbon atoms, etherified hydroxy-lower alkyl, wherein etherified hydroxy is lower alkoxy and separated from the sulfur atom by at least two carbon atoms, carbo-lower alkoxy-lower alkyl, or lower alkenyl or halogen-methyl, the 1-oxide of such 3-cephem compound of the formula IA, the corresponding 2-cephem compound of the formula IB,

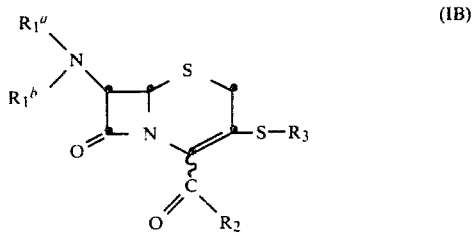

wherein $R_1{}^a$, $R_1{}^b$, $R_2$ and $R_3$ have the meanings indicated under formula IA, a 3-S-oxide thereof or a pharmaceutically acceptable salt of such compound.

2. A 7β-(α-$R_a$-acetylamino)-3-$R_3$-thio-3-cephem-4-carboxylic acid according to claim 1, wherein $R_a$ represents cyano, phenyl, phenoxy, 4-hydrophenyl, 2-thienyl, 5-aminomethyl-2-thienyl, 2furyl, 1-tetrazolyl, 1,4-cyclohexadienyl or 1-cyclohexenyl and $R_3$ represents methyl, 2-aminoethyl, carbomethoxymethyl, allyl, or trityl, or a pharmaceutically acceptable salt thereof.

3. A 7β-(α-$R_a$-α-hydroxyacetylamino)-3-$R_3$-thio-3-cephem-4-carboxylic acid according to claim 1, wherein $R_a$ represents phenyl, 2-thienyl or 2-furyl and $R_3$ represents methyl, 2-aminoethyl, carbomethoxymethyl, allyl, or trityl or a pharmaceutically acceptable salt thereof.

4. A 7β-(α-$R_a$-α-syn-lower alkoxyimino-acetylamino)-3-$R_3$-thio-3-cephem-4-carboxylic acid according to claim 1, wherein $R_a$ denotes phenyl, 2-thienyl or 2 furyl, and $R_3$ represents methyl, 2-aminoethyl, carbomethoxymethyl, allyl, or trityl or a pharmaceutically acceptable salt thereof.

5. A compound according to claim 1 which is 7β-phenylacetylamino-3-phenylthio-3-cephem-4-carboxylic acid or a pharmaceutically acceptable salt thereof.

6. A compound according to claim 1 which is 7β-(D(−)-α-phenylglycylamino)-3-phenylthio-3-cephem-4-carboxylic acid or a pharmaceutically acceptable salt thereof.

7. A compound according to claim 1 which is 7β-(D(−)-α-phenylglycylamino)-3-methylthio-3-cephem-4-carboxylic acid or a pharmaceutically acceptable salt thereof.

8. A compound according to claim 1 which is 3-methylthio-7β-phenoxyacetylamino-3-cephem-4-carboxylic acid or a pharmaceutically acceptable salt thereof.

9. A compound according to claim 1 which is 7β-(D(−)-α-phenylglycylamino)-3-allylthio-3-cephem-4-carboxylic acid or a pharmaceutically acceptable salt thereof.

10. A compound according to claim 1 which is 7β-(D(−)-α-phenylglycylamino)-3-(2-aminoethylthio)-3-cephem-4-carboxylic acid or a pharmaceutically acceptable salt thereof.

11. A compound according to claim 1 which is 7β-(D(−)-α-phenylglycylamino)-3-carbomethoxymethylthio-3-cephem-4-carboxylic acid or a pharmaceutically acceptable salt thereof.

12. A compound according to claim 1 which is 3-carbomethoxymethylthio-7β-phenylacetylamino-3-cephem-4-carboxylic acid or a pharmaceutically acceptable salt thereof.

13. A compound according to claim 1 which is 3-methylthio-7β-(D-mandeloylamino)-3-cephem-4-carboxylic acid or a pharmaceutically acceptable salt thereof.

14. A pharmaceutical preparation comprising an antibacterially effective amount of a compound of claim 1 and a pharmaceutically usable excipient.

15. A method for the treatment of bacterial infections which comprises administering an antibacterially effective amount of a compound of claim 1.

16. A compound of the formula

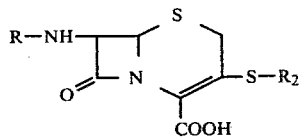

wherein R is selected from the group consisting of
phenylacetyl,
phenylthioacetyl,
phenoxyacetyl,
thienylacetyl
D-α-amino-phenylacetyl or
D-mandeloyl,
and $R_2$ is methyl.

17. A compound of the formula

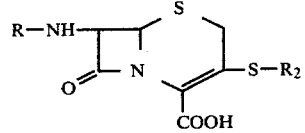

wherein R is selected from the group consisting of
phenylacetyl,
phenylthioacetyl,
phenoxyacetyl,
thienylacetyl,
D-α-aminophenylacetyl, or
D-mandeloyl; and
$R_2$ is phenyl or phenyl substituted by $C_1$–$C_4$ alkyl, halogen or $C_1$–$C_4$ alkoxy.

* * * * *

UNITED STATES PATENT AND TRADEMARK OFFICE
CERTIFICATE OF CORRECTION

PATENT NO. : 4,256,739
DATED : MARCH 17, 1981
INVENTOR(S) : R. B. WOODWARD ET AL

It is certified that error appears in the above—identified patent and that said Letters Patent is hereby corrected as shown below:

Claim 1,
column 73,
structure reads:

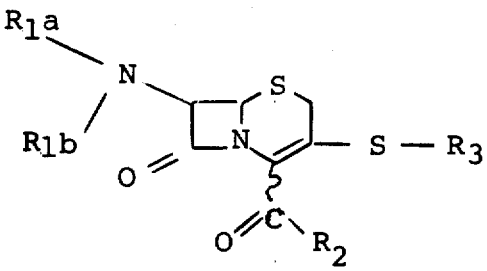

should read:

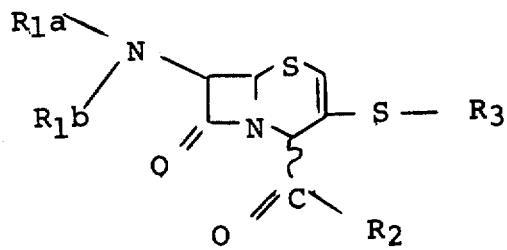

Signed and Sealed this

Eighth Day of September 1981

[SEAL]

Attest:

GERALD J. MOSSINGHOFF

Attesting Officer   Commissioner of Patents and Trademarks